United States Patent
Frater et al.

(10) Patent No.: US 11,071,839 B2
(45) Date of Patent: Jul. 27, 2021

(54) CUSHION FOR A RESPIRATORY MASK ASSEMBLY

(71) Applicant: ResMed Pty Ltd, Bella Vista (AU)

(72) Inventors: Robert Henry Frater, Sydney (AU); Joanne Elizabeth Drew, Sydney (AU); Philip Rodney Kwok, Sydney (AU); Patrick John McAuliffe, Sydney (AU); Aaron Samuel Davidson, Sydney (AU); Robin Garth Hitchcock, Sydney (AU); Michael Kassipillai Gunaratnam, Sydney (AU); Donald Darkin, Sydney (AU); Gary Christopher Robinson, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 16/878,189

(22) Filed: May 19, 2020

(65) Prior Publication Data

US 2021/0030988 A1 Feb. 4, 2021

Related U.S. Application Data

(63) Continuation of application No. 15/916,379, filed on Mar. 9, 2018, now Pat. No. 10,668,241, which is a
(Continued)

(51) Int. Cl.
*A61M 16/06* (2006.01)
*A61M 16/00* (2006.01)
*A61M 16/08* (2006.01)

(52) U.S. Cl.
CPC ...... *A61M 16/065* (2014.02); *A61M 16/0057* (2013.01); *A61M 16/06* (2013.01);
(Continued)

(58) Field of Classification Search
CPC ............ A61M 16/0683; A61M 16/065; A61M 16/0611; A61M 16/0616; A61M 16/0622;
(Continued)

(56) References Cited

U.S. PATENT DOCUMENTS

| 4,429 A | 3/1846 | Cooke et al. |
| 35,724 A | 6/1862 | Wilcox |

(Continued)

FOREIGN PATENT DOCUMENTS

| AU | 91/77110 | 11/1991 |
| AU | 94/64816 | 12/1994 |

(Continued)

OTHER PUBLICATIONS

Proceeding Correspondence dated Dec. 20, 2017 issued in New Zealand Application No. 700217, Proceeding No. 3466 (1 page).
(Continued)

*Primary Examiner* — Valerie L Woodward
(74) *Attorney, Agent, or Firm* — Nixon & Vanderhye P.C.

(57) ABSTRACT

A respiratory mask assembly for delivering breathable gas to a patient includes a frame and a cushion. The cushion has a non-face contacting portion structured to be connected to the frame, a face-contacting portion structured to engage the patient's face, and a central portion that interconnects the non-face contacting portion and the face contacting portion. The frame may be structured to allow a forehead support to assume multiple positions, to compensate for replacement cushions that may have a different profile, shape or size. The cushion is structured to compensate for variations in strap tension, treatment pressure and/or movement of the patient. Headgear may be provided with a strap assembly in which one or more straps is provided with selectively adjustable elasticity or extensibility that may be automatically changed in dependence of treatment pressure and/or treatment type.

13 Claims, 51 Drawing Sheets

Related U.S. Application Data continuation of application No. 15/141,339, filed on Apr. 28, 2016, now Pat. No. 10,039,893, which is a continuation of application No. 13/708,049, filed on Dec. 7, 2012, now Pat. No. 9,375,545, which is a continuation of application No. 13/064,349, filed on Mar. 21, 2011, now Pat. No. 8,353,294, which is a continuation of application No. 11/628,714, filed as application No. PCT/AU2005/000850 on Jun. 15, 2005, now Pat. No. 7,971,590.

(60) Provisional application No. 60/648,687, filed on Feb. 2, 2005, provisional application No. 60/634,272, filed on Dec. 9, 2004, provisional application No. 60/579,678, filed on Jun. 16, 2004.

(52) U.S. Cl.
CPC .... *A61M 16/0611* (2014.02); *A61M 16/0616* (2014.02); *A61M 16/0622* (2014.02); *A61M 16/0638* (2014.02); *A61M 16/0655* (2014.02); *A61M 16/0683* (2013.01); *A61M 16/0644* (2014.02); *A61M 16/0825* (2014.02)

(58) Field of Classification Search
CPC .......... A61M 16/0638; A61M 16/0655; A61M 16/0057; A61M 16/06; A61M 16/0644; A61M 16/0825
See application file for complete search history.

(56) References Cited

U.S. PATENT DOCUMENTS

| | | | |
|---|---|---|---|
| 463,351 A | 11/1891 | Elliott | |
| 715,611 A | 12/1902 | Schnenker et al. | |
| 716,530 A | 12/1902 | Giddens | |
| 781,516 A | 1/1905 | Guthrie | |
| 812,706 A | 2/1906 | Warbasse | |
| 1,070,986 A | 8/1913 | Richter | |
| 1,081,745 A | 12/1913 | Johnston et al. | |
| 1,176,886 A | 3/1916 | Ermold | |
| 1,192,186 A | 7/1916 | Greene | |
| 1,333,075 A | 3/1920 | Hill et al. | |
| 1,381,826 A | 6/1921 | Hansen | |
| 1,653,572 A | 12/1927 | Jackson | |
| 1,672,165 A | 6/1928 | Lewis | |
| 1,733,020 A | 10/1929 | Jones | |
| 1,926,027 A | 9/1933 | Biggs | |
| 2,029,129 A | 1/1936 | Schwartz | |
| 2,033,448 A | 3/1936 | James | |
| 2,123,353 A | 7/1938 | Catt | |
| 2,130,555 A | 9/1938 | Malcom | |
| 2,133,699 A | 10/1938 | Heidbrink | |
| 2,141,222 A | 12/1938 | Pioch | |
| 2,245,658 A | 6/1941 | Erickson | |
| 2,245,969 A | 6/1941 | Francisco et al. | |
| 2,248,477 A | 7/1941 | Lombard | |
| 2,254,854 A | 9/1941 | O'Connell | |
| 2,287,353 A | 6/1942 | Minnick | |
| 2,317,608 A | 4/1943 | Heidbrink | |
| 2,359,506 A | 10/1944 | Battley et al. | |
| 2,371,965 A | 3/1945 | Lehmberg | |
| 2,376,871 A | 5/1945 | Fink | |
| 2,382,364 A | 8/1945 | Yant | |
| 2,415,846 A | 2/1947 | Randall | |
| 2,428,451 A | 10/1947 | Emerson | |
| 2,438,058 A | 3/1948 | Kincheloe | |
| 2,454,103 A | 11/1948 | Swidersky | |
| 2,578,621 A | 12/1951 | Yant | |
| 2,590,006 A | 3/1952 | Gordon | |
| 2,617,751 A | 11/1952 | Bickett | |
| 2,625,155 A | 1/1953 | Engelder | |
| 2,638,161 A | 5/1953 | Jones | |
| 2,664,084 A | 12/1953 | Hammermann | |
| 2,706,983 A | 4/1955 | Matheson et al. | |
| 2,747,464 A | 5/1956 | Bowerman | |
| 2,823,671 A | 2/1958 | Garelick | |
| 2,832,015 A | 4/1958 | Ortega | |
| 2,893,387 A | 7/1959 | Gongoll et al. | |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,141,213 A | 7/1964 | Nicholas | |
| 3,182,659 A | 5/1965 | Blount et al. | |
| 3,189,027 A | 6/1965 | Bartlett | |
| 3,193,624 A | 7/1965 | Webb et al. | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,474,783 A | 10/1969 | Ulmann | |
| 3,494,072 A | 2/1970 | Olson | |
| 3,523,534 A | 8/1970 | Nolan | |
| 3,535,810 A | 10/1970 | Baehrle | |
| 3,555,752 A | 1/1971 | Bogaert | |
| 3,556,122 A | 1/1971 | Laerdal | |
| 3,580,051 A | 5/1971 | Blevins | |
| 3,688,314 A * | 9/1972 | Hill .................. | A62B 18/04 2/457 |
| 3,700,000 A | 10/1972 | Hesse et al. | |
| 3,720,235 A | 3/1973 | Schrock | |
| 3,726,275 A | 4/1973 | Jackson et al. | |
| 3,750,333 A | 8/1973 | Vance | |
| 3,752,157 A | 8/1973 | Malmin | |
| 3,792,702 A * | 2/1974 | Delest .................. | A62B 18/084 128/207.11 |
| 3,796,216 A | 3/1974 | Schwarz | |
| 3,799,164 A | 3/1974 | Rollins | |
| D231,803 S | 6/1974 | Huddy | |
| 3,824,999 A | 7/1974 | King | |
| 3,830,230 A | 8/1974 | Chester | |
| 4,034,426 A | 7/1977 | Hardwick et al. | |
| 4,049,357 A | 9/1977 | Hamisch, Jr. | |
| 4,062,357 A | 12/1977 | Laerdal | |
| 4,064,875 A | 12/1977 | Cramer et al. | |
| 4,069,516 A | 1/1978 | Watkins, Jr. | |
| 4,077,404 A | 3/1978 | Elam | |
| 4,111,197 A | 9/1978 | Warncke et al. | |
| D250,131 S | 10/1978 | Lewis et al. | |
| 4,120,302 A | 10/1978 | Ziegler | |
| 4,121,580 A | 10/1978 | Fabish | |
| 4,161,946 A | 7/1979 | Zuesse | |
| 4,164,942 A | 8/1979 | Beard et al. | |
| 4,167,185 A | 9/1979 | Lewis | |
| 4,222,122 A * | 9/1980 | Toms ................... | A63B 71/10 2/9 |
| 4,226,234 A | 10/1980 | Gunderson | |
| 4,245,632 A | 1/1981 | Houston | |
| 4,265,239 A | 5/1981 | Fischer, Jr. et al. | |
| 4,274,404 A | 6/1981 | Molzan et al. | |
| 4,275,908 A | 6/1981 | Elkins et al. | |
| D262,322 S | 12/1981 | Mizerak | |
| 4,304,229 A | 12/1981 | Curtin | |
| 4,328,797 A | 5/1982 | Rollins et al. | |
| 4,337,767 A | 7/1982 | Yahata | |
| 4,347,205 A | 8/1982 | Stewart | |
| 4,354,488 A | 10/1982 | Bartos | |
| 4,380,102 A | 4/1983 | Hansson | |
| 4,402,316 A | 9/1983 | Gadberry | |
| 4,412,537 A | 11/1983 | Tiger | |
| 4,458,679 A | 7/1984 | Ward | |
| 4,467,799 A | 8/1984 | Steinberg | |
| 4,494,538 A | 1/1985 | Ansite | |
| 4,506,665 A | 3/1985 | Andrews et al. | |
| 4,522,639 A | 6/1985 | Ansite et al. | |
| 4,549,334 A | 10/1985 | Miller | |
| 4,558,710 A | 12/1985 | Eichler | |
| 4,580,556 A | 4/1986 | Kondur | |
| 4,606,340 A | 8/1986 | Ansite | |
| D285,496 S | 9/1986 | Berman | |
| 4,616,647 A | 10/1986 | McCreadie | |

(56) References Cited

U.S. PATENT DOCUMENTS

| | | |
|---|---|---|
| 4,622,964 A | 11/1986 | Flynn |
| 4,633,972 A | 1/1987 | DeRocher |
| 4,655,213 A | 4/1987 | Rapoport et al. |
| 4,665,570 A | 5/1987 | Davis |
| 4,671,271 A | 6/1987 | Bishop et al. |
| 4,676,241 A | 6/1987 | Webb et al. |
| 4,677,975 A | 7/1987 | Edgar et al. |
| 4,677,977 A | 7/1987 | Wilcox |
| 4,713,844 A | 12/1987 | Westgate |
| H397 H | 1/1988 | Stark |
| D293,613 S | 1/1988 | Wingler |
| 4,732,147 A | 3/1988 | Fuller |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,783,029 A | 11/1988 | Geppert et al. |
| 4,799,477 A | 1/1989 | Lewis |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,835,820 A | 6/1989 | Robbins, III |
| 4,841,953 A | 6/1989 | Dodrill |
| 4,848,334 A | 7/1989 | Bellm |
| 4,848,366 A | 7/1989 | Aita et al. |
| 4,870,963 A | 10/1989 | Carter |
| 4,875,714 A | 10/1989 | Lee |
| 4,875,718 A | 10/1989 | Marken |
| 4,898,174 A | 2/1990 | Fangrow, Jr. |
| 4,899,614 A | 2/1990 | Kataumi |
| 4,905,686 A | 3/1990 | Adams |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,210 A | 7/1990 | Flock et al. |
| 4,944,310 A | 7/1990 | Sullivan |
| 4,946,202 A | 8/1990 | Perricone |
| D310,431 S | 9/1990 | Bellm |
| 4,971,051 A | 11/1990 | Toffolon |
| 4,974,586 A | 12/1990 | Wandel et al. |
| 4,974,921 A | 12/1990 | Miyata et al. |
| 4,986,269 A | 1/1991 | Hakkinen |
| 4,989,596 A | 2/1991 | Macris et al. |
| 4,989,599 A | 2/1991 | Carter |
| 4,997,217 A | 3/1991 | Kunze |
| 5,003,633 A | 4/1991 | Itoh |
| 5,005,568 A | 4/1991 | Loescher et al. |
| 5,005,571 A | 4/1991 | Dietz |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,054,482 A | 10/1991 | Bales |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,136,760 A | 8/1992 | Sano et al. |
| 5,140,980 A | 8/1992 | Haughey et al. |
| 5,140,982 A | 8/1992 | Bauman |
| 5,149,980 A | 9/1992 | Ertel et al. |
| 5,156,146 A | 10/1992 | Corces et al. |
| 5,159,938 A | 11/1992 | Laughlin |
| 5,178,138 A | 1/1993 | Walstrom et al. |
| D333,015 S | 2/1993 | Farmer |
| D334,633 S | 4/1993 | Rudolph |
| 5,215,336 A | 6/1993 | Worthing |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,253,641 A | 10/1993 | Choate |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A | 6/1994 | Walther |
| 5,343,878 A | 9/1994 | Scarberry et al. |
| 5,349,949 A | 9/1994 | Schegerin |
| 5,357,951 A | 10/1994 | Ratner |
| 5,372,130 A | 12/1994 | Stern et al. |
| 5,388,273 A | 2/1995 | Sydor et al. |
| 5,388,571 A | 2/1995 | Roberts et al. |
| 5,391,248 A | 2/1995 | Brain |
| 5,398,673 A | 3/1995 | Lambert |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A * | 4/1996 | Bertheau ............ A62B 18/084 |
| | | 128/201.22 |
| 5,509,404 A | 4/1996 | Lloyd et al. |
| 5,517,986 A | 5/1996 | Starr et al. |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,645,049 A | 7/1997 | Foley et al. |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,676,133 A | 10/1997 | Hickle et al. |
| 5,685,296 A | 11/1997 | Zdrojkowski et al. |
| 5,687,715 A | 11/1997 | Landis et al. |
| 5,704,345 A | 1/1998 | Berthon-Jones et al. |
| 5,709,204 A | 1/1998 | Lester |
| 5,715,814 A | 2/1998 | Ebers |
| 5,724,965 A | 3/1998 | Handke et al. |
| 5,743,414 A | 4/1998 | Baudino |
| 5,746,201 A | 5/1998 | Kidd |
| 5,794,617 A | 8/1998 | Brunell et al. |
| 5,813,423 A | 9/1998 | Kirchgeorg |
| 5,832,918 A | 11/1998 | Pantino |
| 5,839,436 A | 11/1998 | Fangrow et al. |
| D402,755 S | 12/1998 | Kwok |

(56) References Cited

U.S. PATENT DOCUMENTS

| | | |
|---|---|---|
| 5,860,677 A | 1/1999 | Martins et al. |
| 5,884,624 A | 3/1999 | Barnett et al. |
| 5,896,857 A | 4/1999 | Hely et al. |
| 5,906,199 A | 5/1999 | Budzinski |
| 5,909,732 A | 6/1999 | Diesel et al. |
| 5,921,239 A | 7/1999 | McCall et al. |
| 5,935,136 A | 8/1999 | Hulse et al. |
| 5,937,851 A | 8/1999 | Serowski et al. |
| 5,975,079 A | 11/1999 | Hellings et al. |
| 5,979,025 A | 11/1999 | Horng |
| 6,016,804 A | 1/2000 | Gleason et al. |
| 6,029,668 A | 2/2000 | Freed |
| 6,039,044 A | 3/2000 | Sullivan |
| D423,096 S | 4/2000 | Kwok |
| 6,044,844 A | 4/2000 | Kwok et al. |
| 6,062,148 A | 5/2000 | Hodge et al. |
| 6,082,360 A | 7/2000 | Rudolph et al. |
| D428,987 S | 8/2000 | Kwok |
| 6,098,205 A | 8/2000 | Schwartz et al. |
| 6,112,746 A | 9/2000 | Kwok et al. |
| 6,119,693 A | 9/2000 | Kwok et al. |
| 6,123,071 A | 9/2000 | Berthon-Jones et al. |
| 6,152,137 A | 11/2000 | Schwartz et al. |
| 6,189,532 B1 | 2/2001 | Hely et al. |
| 6,192,886 B1 | 2/2001 | Rudolph |
| D439,326 S | 3/2001 | Hecker et al. |
| 6,196,223 B1 | 3/2001 | Belfer et al. |
| 6,240,605 B1 | 6/2001 | Stevens et al. |
| 6,250,375 B1 | 6/2001 | Lee et al. |
| 6,256,846 B1 | 7/2001 | Lee |
| 6,257,237 B1 | 7/2001 | Suzuki |
| 6,272,722 B1 | 8/2001 | Lai |
| 6,321,421 B1 | 11/2001 | Lim |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,374,826 B1 | 4/2002 | Gunaratnam et al. |
| 6,381,813 B1 | 5/2002 | Lai |
| 6,388,640 B1 | 5/2002 | Chigira et al. |
| 6,397,847 B1 | 6/2002 | Scarberry et al. |
| 6,412,487 B1 | 7/2002 | Gunaratnam et al. |
| 6,418,928 B1 | 7/2002 | Bordewick et al. |
| 6,422,238 B1 | 7/2002 | Lithgow |
| 6,427,694 B1 | 8/2002 | Hecker |
| 6,431,172 B1 | 8/2002 | Bordewick |
| 6,435,181 B1 | 8/2002 | Jones, Jr. et al. |
| 6,449,817 B1 | 9/2002 | Hsu |
| 6,463,931 B1 | 10/2002 | Kwok et al. |
| 6,467,483 B1 | 10/2002 | Kopacko et al. |
| 6,491,034 B1 | 12/2002 | Gunaratnam et al. |
| 6,494,207 B1 | 12/2002 | Kwok |
| D468,823 S | 1/2003 | Smart |
| 6,513,206 B1 | 2/2003 | Banitt et al. |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Gunaratnam et al. |
| 6,536,435 B1 | 3/2003 | Fecteau et al. |
| 6,557,556 B2 | 5/2003 | Kwok et al. |
| 6,595,214 B1 | 7/2003 | Hecker |
| 6,615,832 B1 | 9/2003 | Chen |
| 6,615,834 B2 | 9/2003 | Gradon et al. |
| 6,626,177 B1 | 9/2003 | Ziaee |
| 6,631,718 B1 | 10/2003 | Lovell |
| D484,237 S | 12/2003 | Lang et al. |
| 6,679,260 B2 | 1/2004 | Her |
| 6,679,261 B2 | 1/2004 | Lithgow |
| 6,691,707 B1 | 2/2004 | Gunaratnam et al. |
| 6,691,708 B2 | 2/2004 | Kwok et al. |
| 6,701,927 B2 | 3/2004 | Kwok et al. |
| 6,705,647 B1 | 3/2004 | Palmer |
| 6,712,072 B1 | 3/2004 | Lang |
| 6,729,333 B2 | 5/2004 | Barnett et al. |
| D492,992 S | 7/2004 | Guney et al. |
| 6,789,543 B2 | 9/2004 | Cannon |
| 6,796,308 B2 | 9/2004 | Gunaratnam et al. |
| 6,823,869 B2 | 11/2004 | Raje |
| 6,832,615 B2 | 12/2004 | Hensel |
| D502,260 S | 2/2005 | Lang et al. |
| 6,851,425 B2 | 2/2005 | Jaffre |
| 6,851,428 B2 | 2/2005 | Dennis |
| 6,860,269 B2 | 3/2005 | Kwok et al. |
| 6,918,390 B2 | 7/2005 | Lithgow et al. |
| 6,926,004 B2 | 8/2005 | Schumacher |
| 6,973,929 B2 | 12/2005 | Gunaratnam |
| 6,986,352 B2 | 1/2006 | Frater et al. |
| D515,698 S | 2/2006 | Lang et al. |
| 6,997,188 B2 | 2/2006 | Kwok et al. |
| 7,000,614 B2 | 2/2006 | Lang et al. |
| 7,005,414 B2 | 2/2006 | Barnikol et al. |
| 7,011,090 B2 | 3/2006 | Drew et al. |
| 7,021,311 B2 | 4/2006 | Gunaratnam et al. |
| 7,036,508 B2 | 5/2006 | Kwok |
| 7,047,965 B1 | 5/2006 | Ball |
| 7,059,326 B2 | 6/2006 | Heidmann et al. |
| 7,066,379 B2 | 6/2006 | Eaton et al. |
| 7,069,932 B2 | 7/2006 | Eaton et al. |
| 7,089,939 B2 | 8/2006 | Walker et al. |
| 7,095,938 B2 | 8/2006 | Tolstikhin |
| 7,100,610 B2 | 9/2006 | Biener et al. |
| 7,107,989 B2 | 9/2006 | Frater et al. |
| 7,112,179 B2 | 9/2006 | Bonutti et al. |
| 7,185,652 B2 | 3/2007 | Gunaratnam et al. |
| 7,207,334 B2 | 4/2007 | Smart |
| 7,216,647 B2 | 5/2007 | Lang et al. |
| 7,219,670 B2 | 5/2007 | Jones et al. |
| 7,234,466 B2 | 6/2007 | Kwok et al. |
| 7,234,773 B2 | 6/2007 | Raftery et al. |
| 7,290,546 B2 | 11/2007 | Ho et al. |
| 7,296,574 B2 | 11/2007 | Sprinkle et al. |
| 7,318,439 B2 | 1/2008 | Raje et al. |
| 7,320,323 B2 | 1/2008 | Lang et al. |
| 7,353,827 B2 | 4/2008 | Geist |
| 7,406,965 B2 | 8/2008 | Kwok et al. |
| 7,472,704 B2 | 1/2009 | Gunaratnam |
| 7,503,327 B2 | 3/2009 | Gunaratnam |
| 7,610,916 B2 | 11/2009 | Kwok et al. |
| 7,614,400 B2 | 11/2009 | Lithgow et al. |
| 7,621,274 B2 | 11/2009 | Sprinkle et al. |
| 7,654,263 B2 | 2/2010 | Lang et al. |
| 7,665,464 B2 | 2/2010 | Kopacko et al. |
| 7,762,259 B2 | 7/2010 | Gunaratnam |
| 7,775,209 B2 | 8/2010 | Biener et al. |
| 7,779,832 B1 | 8/2010 | Ho |
| 7,814,911 B2 | 10/2010 | Bordewick et al. |
| 7,819,119 B2 | 10/2010 | Ho |
| 7,827,987 B2 | 11/2010 | Woodard et al. |
| 7,827,990 B1 | 11/2010 | Melidis |
| 7,856,698 B2 | 12/2010 | Lang et al. |
| 7,856,980 B2 | 12/2010 | Lang et al. |
| 7,861,715 B2 | 1/2011 | Jones et al. |
| 7,882,837 B2 | 2/2011 | Kwok et al. |
| 7,942,149 B2 | 5/2011 | Gunaratnam |
| 7,967,014 B2 | 6/2011 | Heidmann et al. |
| 7,971,590 B2 | 7/2011 | Frater et al. |
| 7,992,559 B2 | 8/2011 | Lang et al. |
| 8,091,553 B2 | 1/2012 | Bordewick et al. |
| 8,113,203 B2 | 2/2012 | Lithgow et al. |
| 8,186,348 B2 | 5/2012 | Kwok et al. |
| 8,210,180 B2 | 7/2012 | Gunaratnam |
| 8,230,855 B2 | 7/2012 | Raje et al. |
| 8,353,294 B2 | 1/2013 | Frater et al. |
| 9,375,545 B2 | 6/2016 | Darkin et al. |
| 10,668,241 B2 | 6/2020 | Frater et al. |
| 2002/0029780 A1 | 3/2002 | Frater |
| 2003/0019495 A1 | 1/2003 | Palkon et al. |
| 2003/0062048 A1 | 4/2003 | Gradon |
| 2003/0075180 A1 | 4/2003 | Raje et al. |
| 2003/0075182 A1 | 4/2003 | Heidmann |
| 2003/0084904 A1 | 5/2003 | Gunaratnam |
| 2003/0089372 A1 | 5/2003 | Frater et al. |
| 2003/0089373 A1 | 5/2003 | Gradon et al. |
| 2003/0196656 A1 | 10/2003 | Moore |
| 2003/0221691 A1 | 12/2003 | Biener |

(56) References Cited

U.S. PATENT DOCUMENTS

| | | |
|---|---|---|
| 2004/0045550 A1 | 3/2004 | Lang et al. |
| 2004/0045551 A1 | 3/2004 | Eaton |
| 2004/0112385 A1 | 6/2004 | Drew et al. |
| 2004/0112387 A1 | 6/2004 | Lang et al. |
| 2004/0118406 A1 | 6/2004 | Lithgow et al. |
| 2004/0133604 A1 | 7/2004 | Lordo |
| 2004/0177850 A1 | 9/2004 | Gradon |
| 2004/0211428 A1 | 10/2004 | Jones |
| 2004/0216747 A1 | 11/2004 | Jones et al. |
| 2004/0226566 A1 | 11/2004 | Gunaratnam et al. |
| 2005/0011521 A1 | 1/2005 | Sprinkle |
| 2005/0199239 A1 | 9/2005 | Lang et al. |
| 2005/0211252 A1 | 9/2005 | Lang et al. |
| 2006/0169286 A1 | 8/2006 | Eifler et al. |
| 2006/0201514 A1 | 9/2006 | Jones et al. |
| 2007/0044804 A1 | 3/2007 | Matula et al. |
| 2007/0137653 A1 | 6/2007 | Wood |
| 2008/0178885 A1 | 7/2008 | Raje et al. |
| 2008/0264421 A1 | 10/2008 | Kwok et al. |
| 2009/0139526 A1 | 6/2009 | Melidis et al. |
| 2009/0173343 A1 | 7/2009 | Omura et al. |
| 2010/0071700 A2 | 3/2010 | Hitchcock et al. |
| 2010/0089401 A1 | 4/2010 | Lang et al. |
| 2010/0282265 A1 | 11/2010 | Melidis et al. |
| 2010/0300447 A1 | 12/2010 | Biener et al. |
| 2011/0030692 A1 | 2/2011 | Jones et al. |
| 2011/0056498 A1 | 3/2011 | Lang et al. |
| 2011/0094516 A1 | 4/2011 | Chang |
| 2011/0174311 A1 | 7/2011 | Gunaratnam |
| 2011/0220110 A1 | 9/2011 | Fraier et al. |
| 2011/0226254 A1 | 9/2011 | Lang et al. |
| 2011/0259337 A1 | 10/2011 | Hitchcock et al. |
| 2012/0174928 A1 | 7/2012 | Raje et al. |
| 2013/0092169 A1 | 4/2013 | Fraier et al. |
| 2016/0235936 A1 | 8/2016 | Frater et al. |
| 2018/0193581 A1 | 7/2018 | Frater et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 97/41018 | 4/1998 |
| AU | 98/89312 | 1/1999 |
| AU | 200071882 | 6/2001 |
| CA | 1039144 | 9/1928 |
| CA | 88122 | 11/1999 |
| CN | 1326371 | 12/2001 |
| CN | 2464353 | 12/2001 |
| CN | 1408453 | 4/2003 |
| CN | 1589920 A | 3/2005 |
| DE | 284 800 | 11/1913 |
| DE | 459 104 | 4/1928 |
| DE | 701 690 | 1/1941 |
| DE | 923 500 | 2/1955 |
| DE | 159396 | 6/1981 |
| DE | 30 15 279 | 10/1981 |
| DE | 33 45 067 | 6/1984 |
| DE | 35 37 507 | 4/1987 |
| DE | 35 39 073 | 5/1987 |
| DE | 40 04 157 | 4/1991 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 21 766 | 3/1998 |
| DE | 297 23 101 | 7/1998 |
| DE | 298 10 846 U1 | 8/1998 |
| DE | 4 99 00 269.5 | 1/1999 |
| DE | 198 17 332 | 1/1999 |
| DE | 198 08 105 | 9/1999 |
| DE | 299 23 126 | 3/2000 |
| DE | 200 05 346 | 5/2000 |
| DE | 299 23 141 | 5/2000 |
| DE | 200 17 940 | 2/2001 |
| DE | 199 54 517 | 6/2001 |
| DE | 199 62 515 | 7/2001 |
| DE | 100 45 183 | 5/2002 |
| DE | 100 51 891 | 5/2002 |
| DE | 198 40 760 | 3/2003 |
| DE | 103 31 837 | 1/2005 |
| DE | 20 2004 018 108 | 2/2005 |
| DE | 103 38 169 | 3/2005 |
| EP | 0 054 154 | 10/1981 |
| EP | 0 252 052 | 1/1988 |
| EP | 0 264 772 | 4/1988 |
| EP | 0 334 555 | 9/1989 |
| EP | 0 386 605 | 2/1990 |
| EP | 0 427 474 | 5/1991 |
| EP | 0 462 701 | 12/1991 |
| EP | 0 303 090 B1 | 4/1992 |
| EP | 0 549 299 | 6/1993 |
| EP | 0 602 424 | 11/1993 |
| EP | 0 608 684 | 8/1994 |
| EP | 0 697 225 | 7/1995 |
| EP | 0 178 925 A2 | 4/1996 |
| EP | 0 747 078 | 12/1996 |
| EP | 0 821 978 | 2/1998 |
| EP | 0 853 962 | 7/1998 |
| EP | 0 958 841 | 11/1999 |
| EP | 1 027 905 | 8/2000 |
| EP | 1 057 494 | 12/2000 |
| EP | 1 099 452 | 5/2001 |
| EP | 1 116 492 A2 | 7/2001 |
| EP | 1 205 205 | 5/2002 |
| EP | 1 334 742 | 8/2003 |
| EP | 1 356 843 | 10/2003 |
| EP | 1 555 039 | 7/2005 |
| ES | 145309 | 1/2000 |
| FR | 2 574 657 | 6/1986 |
| FR | 2 658 725 | 8/1991 |
| FR | 2 691 906 | 12/1993 |
| FR | 2 749 176 | 12/1997 |
| FR | 99/16 | 8/1999 |
| GB | 649 689 | 1/1951 |
| GB | 823 887 | 11/1959 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 186 801 | 8/1987 |
| GB | 2 267 648 | 12/1993 |
| GB | 2080119 | 12/1998 |
| GB | 2080120 | 12/1998 |
| GB | 2080121 | 12/1998 |
| JP | S39-13991 | 7/1964 |
| JP | S48-55696 | 10/1971 |
| JP | S52-76695 | 6/1977 |
| JP | S52-164619 | 12/1977 |
| JP | S59-55535 | 4/1984 |
| JP | S61-67747 | 5/1986 |
| JP | H07-21058 | 4/1995 |
| JP | H07-308381 | 11/1995 |
| JP | H09-501084 | 2/1997 |
| JP | H09-216240 | 8/1997 |
| JP | H09-292588 | 11/1997 |
| JP | H11-000397 | 1/1999 |
| JP | 1105649 | 2/1999 |
| JP | 11-104256 | 4/1999 |
| JP | H11-381522 | 11/1999 |
| JP | 2000-135103 | 5/2000 |
| JP | 2000-279520 | 10/2000 |
| JP | 2000-515784 | 11/2000 |
| JP | 2003-502119 | 2/2003 |
| JP | 2003-175106 | 6/2003 |
| JP | 2003-190308 | 7/2003 |
| JP | 2004-329941 | 11/2004 |
| JP | 2005-506156 | 3/2005 |
| JP | 3686609 | 8/2005 |
| SE | 65 481 | 8/2000 |
| WO | WO 80/01044 | 5/1980 |

(56) References Cited

FOREIGN PATENT DOCUMENTS

| | | |
|---|---|---|
| WO | WO 80/01645 | 8/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 95/04566 | 2/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/30123 | 7/1998 |
| WO | WO 98/34665 | 8/1998 |
| WO | WO 98/48878 | 11/1998 |
| WO | WO 99/21618 | 5/1999 |
| WO | WO 99/30760 | 6/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/21600 | 4/2000 |
| WO | WO 00/38772 | 7/2000 |
| WO | WO 00/50121 | 8/2000 |
| WO | WO 00/57942 | 10/2000 |
| WO | WO 00/69521 | 11/2000 |
| WO | WO 00/78381 | 12/2000 |
| WO | WO 00/78384 | 12/2000 |
| WO | 2001/062326 | 8/2001 |
| WO | WO 01/97892 | 12/2001 |
| WO | WO 01/97893 | 12/2001 |
| WO | WO 02/07806 | 1/2002 |
| WO | WO 02/11804 | 2/2002 |
| WO | WO 02/32491 | 4/2002 |
| WO | WO 02/45784 | 6/2002 |
| WO | WO 02/47749 | 6/2002 |
| WO | WO 03/035156 | 5/2003 |
| WO | WO 03/059427 | 7/2003 |
| WO | WO 03/082406 | 10/2003 |
| WO | WO 03/105921 | 12/2003 |
| WO | WO 2004/012803 | 2/2004 |
| WO | WO 2004/021960 | 3/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | WO 2004/041342 | 5/2004 |
| WO | WO 2004/078228 | 9/2004 |
| WO | WO 2005/018523 | 3/2005 |
| WO | WO 2005/028010 | 3/2005 |
| WO | WO 2005/063326 | 7/2005 |
| WO | WO 2005/068002 | 7/2005 |
| WO | WO 2005/123166 | 12/2005 |

OTHER PUBLICATIONS

Opponent letter dated Dec. 13, 2017 in New Zealand Application No. 700217, Proceeding No. 3466 (3 pages).
Communication dated Dec. 13, 2017 issued in European Application No. 05 749 447.8 (7 pages).
Communication Regarding Deadline for Counterstatement dated Jul. 10, 2017 issued in New Zealand Application No. 700217 (2 pages).
Statement of Case dated Jun. 8, 2017, filed by Fisher & Paykel Healthcare Limited in New Zealand Application No. 700217 (17 pages).
Amended Notice of Opposition to Grant of Patent (Section 21), with no markups, dated Jun. 8, 2017, filed by Fisher & Paykel Healthcare Limited in New Zealand Application No. 700217 (2 pages).
Amended Notice of Opposition to Grant of Patent (Section 21), with markups, dated Jun. 8, 2017, filed by Fisher & Paykel Healthcare Limited in New Zealand Application No. 700217 (2 pages).
First Examination Report dated Mar. 20, 2017 issued in Australian Application No. 2016210611 (3 pages).
Communication dated Mar. 30, 2017 issued in New Zealand Application No. 700217 (1 page).
Notice of Opposition to Grant of Patent dated Mar. 27, 2017 filed by Fisher & Paykel Healthcare Limited in New Zealand Application No. 700217 (2 pages).
Application for Extension of Time dated Mar. 27, 2017 filed by Fisher & Paykel Healthcare Limited in New Zealand Application No. 700217 (1 page).
Office Action dated Feb. 15, 2017 issued in European Application No. 05749447.8 (6 pages).
Further Examination Report dated Nov. 7, 2016 issued in New Zealand Application No. 700217 (2 pages).
Further Examination Report issued in corresponding New Zealand Application No. 700217 dated Jul. 25, 2016.
Notification to Grant Patent Right for Invention issued in corresponding Chinese Application No. 201310024946.7 dated May 3, 2016, with partial English language translation thereof.
First Office Action dated Mar. 5, 2018 issued in Chinese Application No. 201610566485.X with English translation (13 pages).
Proceeding Correspondence dated Mar. 5, 2018 issued in New Zealand Application No. 700217 (3 pages).
Proceeding Correspondence dated Apr. 23, 2018 issued in New Zealand Application No. 700217 (4 pages).
Proceeding Correspondence dated May 3, 2018 issued in New Zealand Application No. 700217 (2 pages).
Proceeding Correspondence dated Jul. 4, 2018 issued in New Zealand Application No. 700217 (1 page).
Opponent's Comments on Amended Claims filed Jun. 14, 2018 in New Zealand Application No. 700217 (3 pages).
Letter filed Aug. 2, 2018 by AJPark in New Zealand Application No. 700217 (6 pages).
Proceeding Correspondence dated Aug. 16, 2018 issued in New Zealand Application No. 700217 (2 pages).
Letter dated Oct. 2, 2018 filed by AJ Park in New Zealand Application No. 700217 (2 pages).
Proceeding Correspondence dated Oct. 10, 2018 issued in New Zealand Application No. 700217 (1 page).
Proceeding Correspondence dated Nov. 8, 2018 issued in New Zealand Application No. 700217 (3 pages).
Extended European Search Report dated Jul. 30, 2019 in European Application No. 18248088.9, 11 pages.
Frater et al., U.S. Appl. No. 15/916,379, filed Mar. 9, 2018, for "Cushion for a Respiratory Mask Assembly," (parent application).
9 photographs of Weinmann mask, WM 23122, 1991.
4 additional photographs of "Weinmann Mask", before applicant's filing date.
Photograph of Weinmann Mask, acquired prior to 1998.
Australian Appln. No. 2010201443—Examiner's First Report, dated Jun. 22, 2011.
Australian Appln. No. 2006206044—Examiner's First Report, dated Dec. 1, 2010.
Australian Appln. No. 2005256167—Examiner's First Report, dated Apr. 29, 2010.
Australian Appln. No. 2005253641—Examiner's First Report, dated Apr. 20, 2010.
Australian Appln. No. 2005253641—Examiner's Report, dated Aug. 18, 2011.
Chinese Appln. No. 201010620187.7—Office Action (w/English translation), dated Jul. 10, 2012.

(56) References Cited

OTHER PUBLICATIONS

Chinese Appln. No. 201010620187.7—Office Action (w/English translation), dated Oct. 26, 2011.
Chinese Appln. No. 201010508994.X—Office Action (w/ English translation), dated Jun. 15, 2011.
Chinese Appln. No. 200580021230.5—Office Action (w/English translation), dated Jul. 3, 2009.
Chinese Appln. No. 2004800402201—Office Action (w/English translation), acquired Jan. 2009.
Chinese Appln. No. 200410038106.7—Office Action (w/English translation), dated Jun. 15, 2007.
Chinese Appln. No. 200580020203.6—Office Action, dated Jun. 1, 2010.
Chinese Appln. No. 200580020203.6—Office Action (w/English translation), dated Jul. 6, 2011.
Chinese Appln. No. 200580020203.6—Office Action (w/English translation), dated Apr. 18, 2012.
Chinese Appln. No. 200580020203.6—Third Office Action (w/English translation), dated Dec. 23, 2011.
DeVilbiss Serenity Mask—Instruction Guide 9352 Series, before applicant's filing date.
DeVilbiss Serenity Mask—Mask Accessories, before applicant's filing date.
European Appln. No. EP 10185073.3—Search Report, dated Dec. 6, 2010.
European Appln. No. EP 10185072.5—Search Report, dated Dec. 6, 2010.
European Appln. No. EP 10185071.7—Search Report, dated Dec. 6, 2010.
European Appln. No. EP 10182015.7—Search Report, dated Jun. 15, 2012.
European Appln. No. EP 10181516.5—Search Report, dated Jun. 13, 2012.
European Appln. No. EP 10166255.9—Search Report, dated Oct. 25, 2010.
European Appln. No. EP 09178736.6—Search Report, dated Apr. 19, 2010.
European Appln. No. EP 09003544.5—Search Report, dated Jun. 2, 2009.
European Appln. No. EP 08161868.8—Search Report, dated Sep. 23, 2008.
European Appln. No. EP 06704773.8—Supplementary Search Report, dated Mar. 29, 2011.
European Appln. No. EP 05753870.4—Office Action, dated Jul. 19, 2010.
European Appln. No. EP 05753870.4—Supplementary Search Report, dated Dec. 15, 1999.
European Appln. No. EP 04730413.4—Supplementary Search Report, dated Sep. 29, 2009.
European Appln. No. EP 03793491.6—Supplementary Search Report, dated Jun. 15, 2010.
European Appln. No. EP 02714190.2—Search Report, dated Jul. 11, 2006.
European Appln. No. EP 02445110.6—Search Report, dated Nov. 6, 2003.
European Appln. No. EP 05749447—Supplementary Search Report, dated Dec. 2, 2009.
German Patent No. 101 51 984—Decision from Opposition hearing by Weinmann (w/English translation), dated Dec. 6, 2007.
Japanese Appln. No. 2008-318985—Office Action (w/English translation), dated Jun. 14, 2011.
Japanese Appln. No. 2007-550640—Office Action (w/English translation), dated Mar. 27, 2012.
Japanese Appln. No. 2007-550640—Office Action (w/English translation), dated Mar. 29, 2011.
Japanese Appln. No. 2007-516895—Office Action (w/English translation), dated Aug. 24, 2010.
Japanese Appln. No. 2005-004072—Office Action (w/English translation), dated Sep. 24, 2009.
Japanese Appln. No. 2004-569777—Office Action (w/English translation), dated Mar. 3, 2009.
Japanese Appln. No. 2004-137431—Office Action (w/English translation), dated Dec. 8, 2009.
Japanese Appln. No. 2003-537718—Office Action (w/English translation), dated Oct. 7, 2008.
Japanese Appln. No. 2001-504444—Office Action (w/English translation), dated Oct. 26, 2004.
Japanese Appln. No. 2000-029094—Office Action (w/English translation), dated 2004.
Japanese Appln. No. 2007-515732—Office Action, dated Aug. 24, 2010.
Japanese Appln. No. 2007-515732—Office Action (w/English translation), dated Jun. 12, 2012.
Japanese Appln. No. 2007-515732—Office Action (w/English translation), dated Aug. 16, 2011.
Mask 1 Photographs, Respironics Inc., Resuable Full Mask (small) Part #452033 Lot #951108, before applicant's filing date.
Mask 2 Photographs, Puritan—Bennett, Adam Curcuit, Shell Part #231700, Swivel Part #616329-00, Pillows (medium) Part #616324, before applicant's filing date.
Mask 3 Photographs DeVilbiss Healthcare Inc., Devilbiss Seal-Ring and CPAP Mask Kit (medium), Part #73510-669, before applicant's filing date.
Mask 4 Photographs, Respironics Inc., Monarch Mini Mask with Pressure Port, Part #572004, Monarch Headgear, Part #572011, before applicant's filing date.
Mask 5 Photographs, Healthdyne Technologies, Nasal CPAP Mask (medium narrow), Part #702510, before applicant's filing date.
Mask 6 Photographs, Healthdyne Technologies, Soft Series Nasal CPAP Mask, Part #702020, before applicant's filing date.
Mask 7 Photographs, DeVilbiss Healthcare Inc., Small Mask and Seal Rings, Part #73510-668, before applicant's filing date.
Mask 8 Photographs, Respironics Inc., Reusable Contour Mask (medium), Part #302180, before applicant's filing date.
Mask 9 Photographs, Healthdyne Technologies, Healthdyne Large Headgear, before applicant's filing date.
Mask 10 Photographs, Respironics Inc., Soft Cap (medium), Part #302142, before applicant's filing date.
Mask 11 Photographs, Weinmann. Hamburg, Nasalmaskensystem mit Schalldämpfer (medium), Part #WN 23105, before applicant's filing date.
Mask 12 Photographs, Life Care, before applicant's filing date.
Mask 13 Photographs, Healthdyne Technologies, before applicant's filing date.
Mark 14 Photographs, King System, before applicant's filing date.
Mask 15 Photographs, Respironics Inc., Pediatric Mask, before applicant's filing date.
Mask 16 Photographs, Hans Rudolph Inc., Hans Rudolph Silicone Rubber Face Mask/8900, before applicant's filing date.
New Zealand Appln. No. 592219—Examination Report, dated Apr. 18, 2011.
New Zealand Appln. No. 556041—Examination Report, dated May 6, 2011.
New Zealand Appln. No. 587820—Examination Report, dated Sep. 13, 2010.
PCT/AU2006/000037—International Search Report, dated Mar. 17, 2006.
PCT/AU2005/000931—International Preliminary Report on Patentability, dated Dec. 28, 2006.
PCT/AU2005/000931—International Search Report, dated Jul. 19, 2005.
PCT/AU2004/000563—International Search Report, dated Jul. 23, 2004.
PCT/EP2004/012811—International Search Report, dated Apr. 12, 2005.
PCT/AU03/01160—International Search Report, dated Oct. 8, 2003.
PCT/AU2005/000850—International Search Report, dated Aug. 12, 2005.
PCT/AU2005/000850—International Preliminary Report on Patentability, dated Dec. 20, 2006.
Product Brochure for ResMed "Sullivan® Mirage™—The Mirage is Real. A Perfect Fit-First Time," ©1997 ResMed Limited, 4 pages.

(56) References Cited

OTHER PUBLICATIONS

Product Brochure for ResMed "Sullivan® Mirage™—The Mirage is Real. A Perfect Fit-First Time," ©1998 ResMed Limited, 4 pages.
ResCare Limited, "Sullivan™ Nasal CPAP System, Nose Mask Clip—User Instructions" 5/90, 1 page, before applicant's filing date.
ResMed, Mask Systems Product Brochure, Sep. 1992, 2 pages.
ResMed Ltd., "Improving patient compliance with The ResMed Range of Mask Systems The Ultimate Interface for CPAP treatment," 4 pages, before applicant's filing date.
The ResMed Range of Mask Systems, product brochure, Nov. 1995, 4 pages.
Respironics, Inc., "Nasal Mask System Silicone Contour Mask," Product Instructions, Jun. 1997, 2 pages.
"Somnomask" brochure, 1999.
Somnotron CPAP-Great WM 2300 Instruction Manual, Weinmann Hamburg, 1991, 11 pages.
U.S. Appl. No. 60/227,472, filed Aug. 24, 2000 (expired).
U.S. Appl. No. 60/424,696, filed Nov. 2002 (expired).
U.S. Appl. No. 60/467,572, filed May 5, 2003 (expired).
U.S. Appl. No. 60/643,121, filed Jan. 12, 2005 (expired).
Patent Examination Report No. 1 issued in corresponding Australian Appln. No. 2012201085 dated Sep. 2, 2013.
Office Action issued in corresponding Chinese Appln. No. 201310024946.7 dated Nov. 2, 2014 with English language translation thereof.
Second Office Action issued in corresponding Chinese Appln. No. 201310024946.7 dated May 5, 2015, with English language translation thereof.

\* cited by examiner

Tailored Contact Force to keep within the zone for constant gusset extension

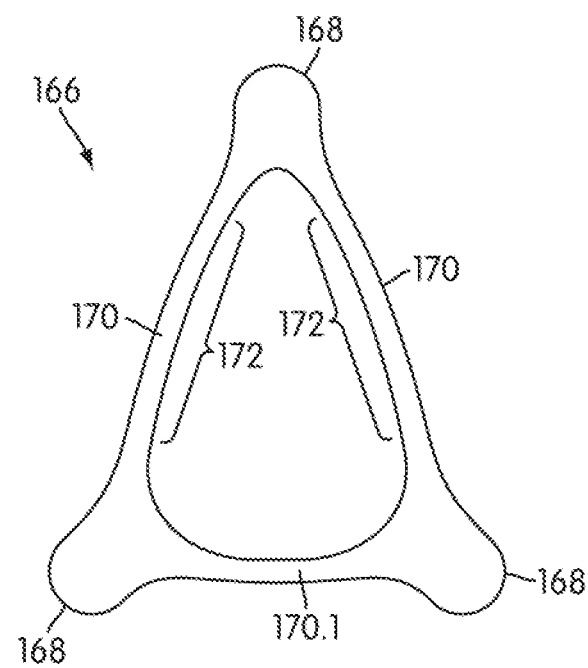
Fig. 12
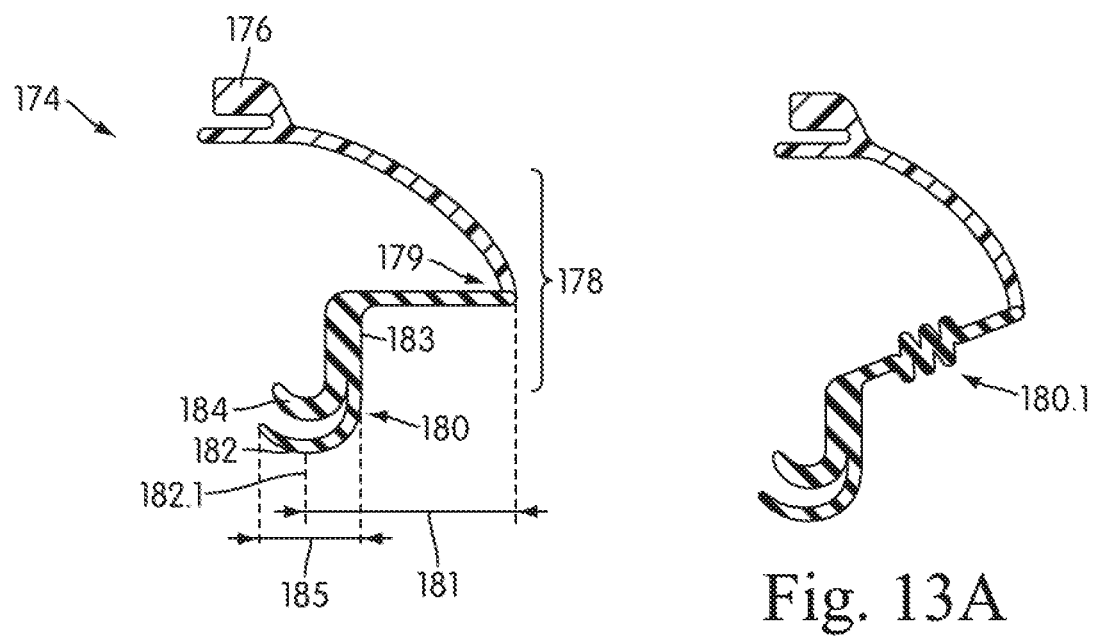
Fig. 13
Fig. 13A

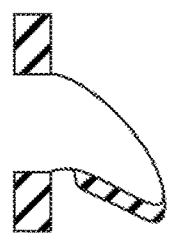 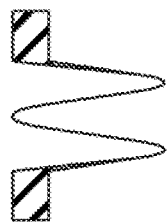 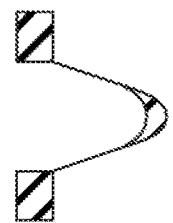
Fig. 24K  Fig. 24L  Fig. 24M
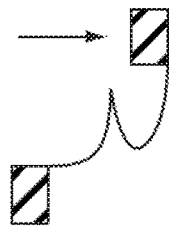 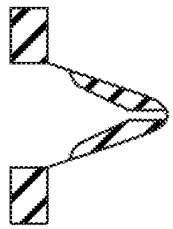 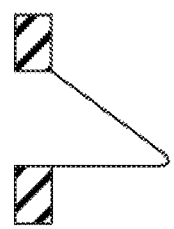
Fig. 24N  Fig. 24O  Fig. 24P
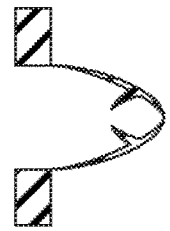 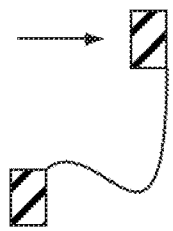 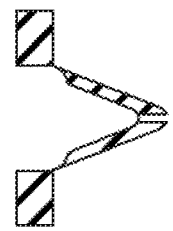
Fig. 24Q  Fig. 24R  Fig. 24S
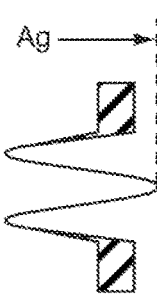 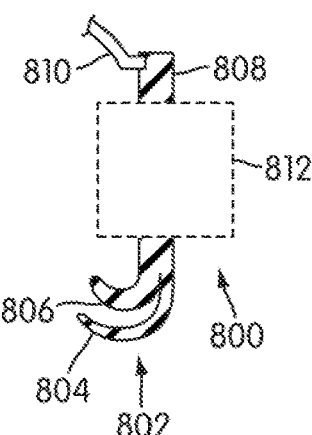
Fig. 24T  Fig. 24U

CUSHION FOR A RESPIRATORY MASK ASSEMBLY

CROSS REFERENCE TO RELATED APPLICATIONS

This application is a continuation of U.S. application Ser. No. 15/916,379, filed Mar. 9, 2018, now U.S. Pat. No. 10,668,241, which is a continuation of U.S. application Ser. No. 15/141,339, filed Apr. 28, 2016, now U.S. Pat. No. 10,039,893, which is a continuation of U.S. application Ser. No. 13/708,049, filed Dec. 7, 2012, now U.S. Pat. No. 9,375,545, which is a continuation of U.S. application Ser. No. 13/064,349, filed Mar. 21, 2011, now U.S. Pat. No. 8,353,294, which is a continuation of U.S. application Ser. No. 11/628,714, filed Dec. 7, 2006, now U.S. Pat. No. 7,971,590, which is the U.S. National Phase of International Application No. PCT/AU2005/000850, filed Jun. 15, 2005, which designated the U.S. and claims the benefit of U.S. Provisional Application No. 60/648,687, filed Feb. 2, 2005, U.S. Provisional Application No. 60/634,272, filed Dec. 9, 2004, and U.S. Provisional Application No. 60/579,678, filed Jun. 16, 2004, each of which is incorporated herein by reference in its entirety. Also U.S. Non-Provisional application Ser. No. 09/885,445 filed Jun. 21, 2001, now U.S. Pat. No. 6,986,352, and U.S. Non-Provisional patent application Ser. No. 10/655,622 filed Sep. 5, 2003, now U.S. Pat. No. 7,523,754, are incorporated by reference in their entireties.

FIELD OF THE INVENTION

The present invention relates to a cushion for a respiratory mask assembly used for providing ventilatory support, e.g., for treatment of Sleep Disordered Breathing (SDB) with Non-invasive Positive Pressure Ventilation (NPPV).

BACKGROUND OF THE INVENTION

The use of NPPV for treatment of SDB such as Obstructive Sleep Apnea (OSA) was pioneered by Sullivan (see U.S. Pat. No. 4,944,310). Apparatus for the treatment of SDB involves a blower which delivers a supply of air at positive pressure to a patient interface via a conduit. The patient interface may take several forms, such as a nasal mask assembly and a nasal and mouth mask assembly. Patients typically wear a mask assembly while sleeping to receive the NPPV therapy.

Mask assemblies typically comprise a rigid shell or frame and a soft face-contacting cushion. The cushion spaces the frame away from the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

U.S. Pat. No. 5,243,971 (Sullivan and Bruderer) describes a nasal mask assembly for Continuous Positive Airway Pressure (CPAP) having a ballooning/molding seal that conforms with the patient's nose and facial contours. The mask assembly has a face-contacting portion mounted to a shell which is sized and shaped to overfit the nose region of the patient. The face-contacting portion is in the form of a distendable membrane which is molded from an elastic plastics material. The distendable membrane and the shell together define a chamber. Pressurized gas admitted to the chamber causes the membrane to distend outwardly from the patient's face. The contents of this patent are hereby incorporated by reference.

U.S. Pat. No. 6,112,746 (Kwok et al.) describes a nasal mask assembly and a mask cushion therefor. The cushion comprises a substantially triangularly shaped frame from which extends a membrane. The frame has a scalloped edge by which the cushion is affixed to a mask body. The membrane has an aperture into which the patient's nose is received. The membrane is spaced away from the rim of the frame, and its outer surface is of substantially the same shape as the rim. U.S. Pat. No. 6,513,526 (Kwok et al.) describes such a cushion for use with a full face mask. The entire contents of these patents are hereby incorporated by reference.

In a traditional mask assembly including a cushion, a seal is formed between the cushion and the face of a patient as the result of a contact force which acts along a contact line of the cushion. The contact force typically is a function of tension in the headgear straps which acts through the frame of the mask assembly, the walls of the cushion and the seal-forming portion of the cushion. In a traditional mask assembly, the frame defines a cavity or volute adapted to receive at least a portion of the nose, with the cushion forming a perimeter of the cavity. Thus, in use, the portion of the patient's face within the cavity is exposed to air or breathable gas at positive pressure and hence receives a force as the result of that positive pressure.

U.S. Pat. No. 5,074,297 (Venegas) describes a respiratory mask assembly for use with intermittent positive pressure breathing treatment which is said to facilitate the formation and automatic adjustment of the seal between a patient's face and a facial unit of the respiratory mask. The respirator mask assembly comprises a facial unit, an expandable piston adjacent the facial unit and a rigid support structure attached to one end of the piston, and an attachment mechanism for securing the mask assembly to a patient. During the inspiration portion of the ventilation cycle a positive pressure is developed within the mask assembly, causing the piston to expand. Because the attachment mechanism and the support cooperate to resist significant expansion of the piston, a force is generated which presses the facial unit against the patient's face and maintains an air tight seal. When pressure within the mask unit decreases, the contact force on the facial unit is likewise decreased and the seal is eliminated.

A common problem with prior art mask assemblies, such as the mask assemblies taught by U.S. Pat. Nos. 5,074,297, 5,243,971 and 6,112,746, is patient comfort. Patients can develop sores and red marks on their faces after several hours use of a mask assembly. The nasal bridge area of the patient's face has been identified as being particularly sensitive.

Moreover, the face contacting portion may apply excessive pressure to the wearer's face resulting in discomfort and possibly skin irritation. This can occur when the face contacting portion is distorted beyond its normal range of elasticity to conform to certain facial contours, thus requiring the application of excessive forces to obtain a seal. In some cases, these excessive pressures and forces may cause the wearer's face to distort to conform with the face contacting portion, which increases wearer discomfort, facial soreness and ulceration.

Another common problem with prior art mask assemblies is buildup of $CO_2$ in the mask cavity. Mask assemblies typically include a vent which allows the continuous washout of exhaled gasses from the cavity. One factor affecting the washout of exhaled gases is the dead space within the mask cavity.

Another common problem with these masks is a broken or ineffective seal. For example, the mask may become dislodged if the wearer rolls over when sleeping, thereby creating a drag force on the gas supply line which is transmitted to the mask and breaking the seal between the mask and wearer. If a mask is used for the administration of Continuous Positive Airway Pressure (CPAP) treatment for the condition obstructive sleep apnea, such a leak can result in a pressure supplied to the entrance of the wearer's airway that is below the therapeutic value. Thus, treatment becomes ineffective.

Another problem with existing full face (oro-nasal) masks occurs when wearers move their jaws during treatment, which often happens. As a result, air leaks are created below the mouth from the mid-region extending to the region at the sides or corners of the mouth.

To address these and other problems, the masks described in U.S. Non-Provisional application Ser. No. 09/885,455 filed Jun. 21, 2001, and U.S. Non-Provisional patent application Ser. No. 10/655,622, have been developed. One aspect common to these applications includes the concept of a gusset section. However, there is perhaps at least a perception that the gusset section is large in terms of its visual appearance, despite the benefits derived from the gusset section.

There are a number of mask systems on the market today which do not have one or more of the benefits of the masks described in these applications. Rather than completely reconfigure the currently existing designs, it may be economically more desirable to merely redesign only a portion the mask system, or component thereof, to take advantage of one or more of the teachings and benefits offered by applicants' prior solutions.

SUMMARY OF THE INVENTION

One aspect of the invention is directed towards a mask assembly having a cushion that provides more comfort to the patient.

Another aspect of the invention is directed towards a mask assembly having a cushion that controllably distributes facial contact pressure around the patient's face.

A further aspect is directed to a forehead support that can be moved to accommodate facial cushions having different depths and/or profiles.

Another aspect of the invention is directed towards a mask assembly having a cushion that controllably distributes facial contact forces around a contact line on the patient's face. In one example, a gusset portion may be provided that is tailored to have variable or varying widths. The gusset portion may be formed, profiled and sized with varying widths. Alternatively, the profile or effective width can be changed using one or more clamps provided along any portion of the cushion perimeter.

Another aspect of the invention is directed towards a mask assembly which has minimal impingement of a patient's vision.

Another aspect of the invention is directed towards a mask assembly having a cushion which has a low profile.

Another aspect of the invention is directed towards a mask assembly which seals at a low pressure and which is comfortable at high pressures.

Another aspect of the invention is directed towards a mask assembly having a cushion which provides reinforcement structure to regulate pressure distribution.

Another aspect of the invention is directed towards a mask assembly providing additional footprint area and/or a spring section with a spring constant constructed so that the forces on the face from the cushion are a function of the mask pressure and the additional footprint area, and/or the spring constant of the spring section.

A further aspect of embodiments of the invention provides a full face mask with a cushion that forms a stable and reliable seal with a wearer's face.

An additional aspect of embodiments of the invention provides a full face mask that effectively seals the region directly below and/or to the sides of the lower lip.

A further aspect of embodiments of the invention provides a full face mask that offers effective and comfortable sealing at relatively high pressures.

In one example, a respiratory mask assembly for delivering breathable gas to a patient includes a frame to support one of at least first and second compliant patient interfaces; and a forehead support adjustably mounted to the frame, wherein the forehead support is structured and configured to be moved between a first position for use with the first patient interface and a second position relative to the frame for use with a second patient interface, whereby the forehead support maintains a horizontal offset distance with the first and second patient interfaces which is substantially constant.

In another example, a cushion for a respiratory mask to deliver breathable gas in a range of operating pressures to a patient includes a non-face contacting portion connected to a frame; a face-contacting portion structured to form a contact seal with the patient's face in use; and a central portion that interconnects the non-face contacting portion and the face-contacting portion, the central portion being structured to automatically adjust a component of force applied to the patient's face through the face-contacting portion in accordance with operating pressure, while maintaining the contact seal throughout the range of operating pressures.

Principles of these examples may be applied to any type of cushion for use on a respiratory mask, including but not limited to silicone elastomer, gel, foam or any combination thereof.

Principles of these examples may be applied to any type of respiratory mask, including CPAP systems or non-positive ventilation masks, such as respirators.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 12 is a schematic top or rear view according to still another embodiment of the present invention;

FIG. 13 is a partial schematic view of another embodiment of the present invention;

FIG. 13A is a partial schematic view of yet another embodiment of the present invention;

DETAILED DESCRIPTION OF ILLUSTRATED EMBODIMENTS

Upgradable Cushion/Forehead Connector System

Figure 1:
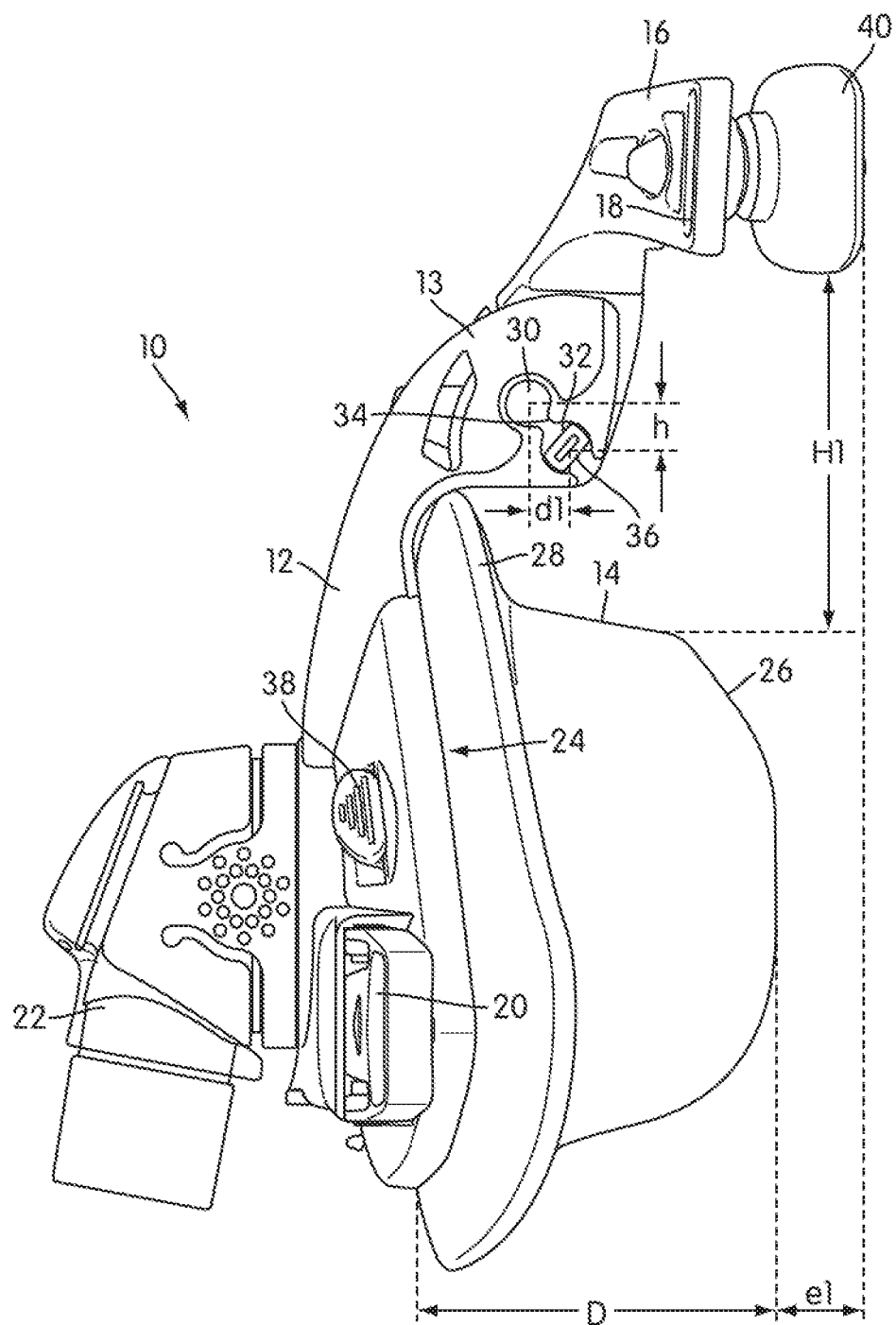
FIG. 1 is a side view of a mask assembly illustrating a first embodiment of the invention in a first position.

FIG. 1 shows a respiratory mask assembly 10 that includes a frame 12 and a cushion 14 that may be permanently or removably connected to the frame 12. A forehead support 16 is movably mounted to an upper portion 13 of the frame 12. A headgear assembly (not shown) can be removably attached to the frame 12 and/or forehead support 16 to maintain the frame 12 and cushion 14 in a desired adjusted position on the patient's face. For example, the headgear assembly may include a pair of upper and lower straps with the upper straps removably connected to slotted connector structures 18 provided on the forehead support 16 and the lower straps removably connected to slotted clip structures 20 provided on the frame 12. The slotted connector structures 18 may be replaced with slotted clip structures. The headgear assembly and frame 12 may be removably attached to one another in any suitable manner.

In the illustrated embodiment, the mask assembly 10 is a nasal mask structured to deliver breathable gas to a patient's nose. However, the mask assembly 10 may be a mouth (oro) mask or the mask assembly may be a full-face (oro-nasal) mask. In another alternative, the cushion could be replaced with a nozzle assembly, as taught in ResMed Limited's. U.S. Non-provisional patent application Ser. No. 10/781,929, filed Feb. 20, 2004, incorporated herein by reference in its entirety.

A swivel elbow assembly 22 is removably attached to a front portion of the frame 12. The elbow assembly 22 is structured to be connected to a conduit that is connected to a pressurized supply. The pressurized supply supplies pressurized breathable gas through the conduit and elbow assembly 22 and into the cushion 14 for breathing by the patient.

As compared to the aforementioned U.S. Non-Provisional patent application Ser. No. 10/655,622, the mask assembly includes one main difference, which relates to the upper portion 13 of the frame 12. All other aspects and components are similar to or exactly as described in U.S. Non-Provisional patent application Ser. No. 10/655,622.

The mask assembly 10 may be provided with the ability to allow two or more cushions 14 for use with frame 12. In particular, the upper portion 13 of the frame 12 includes first and second slots 30, 32 connected by a keyway 34. In FIG. 1, a pivot shaft 36, which is provided in this example on each side of the forehead support 16, is positioned in the second slot 32. This position is desirable for use with the cushion 14, which includes a gusset portion 28, as the presence of the gusset portion 28 may increase a distance D measured from the frame 12 (where it interfaces with non-face contacting portion 24 of the cushion 14) to face-contacting portion 26 of the cushion 14.

Figure 2:
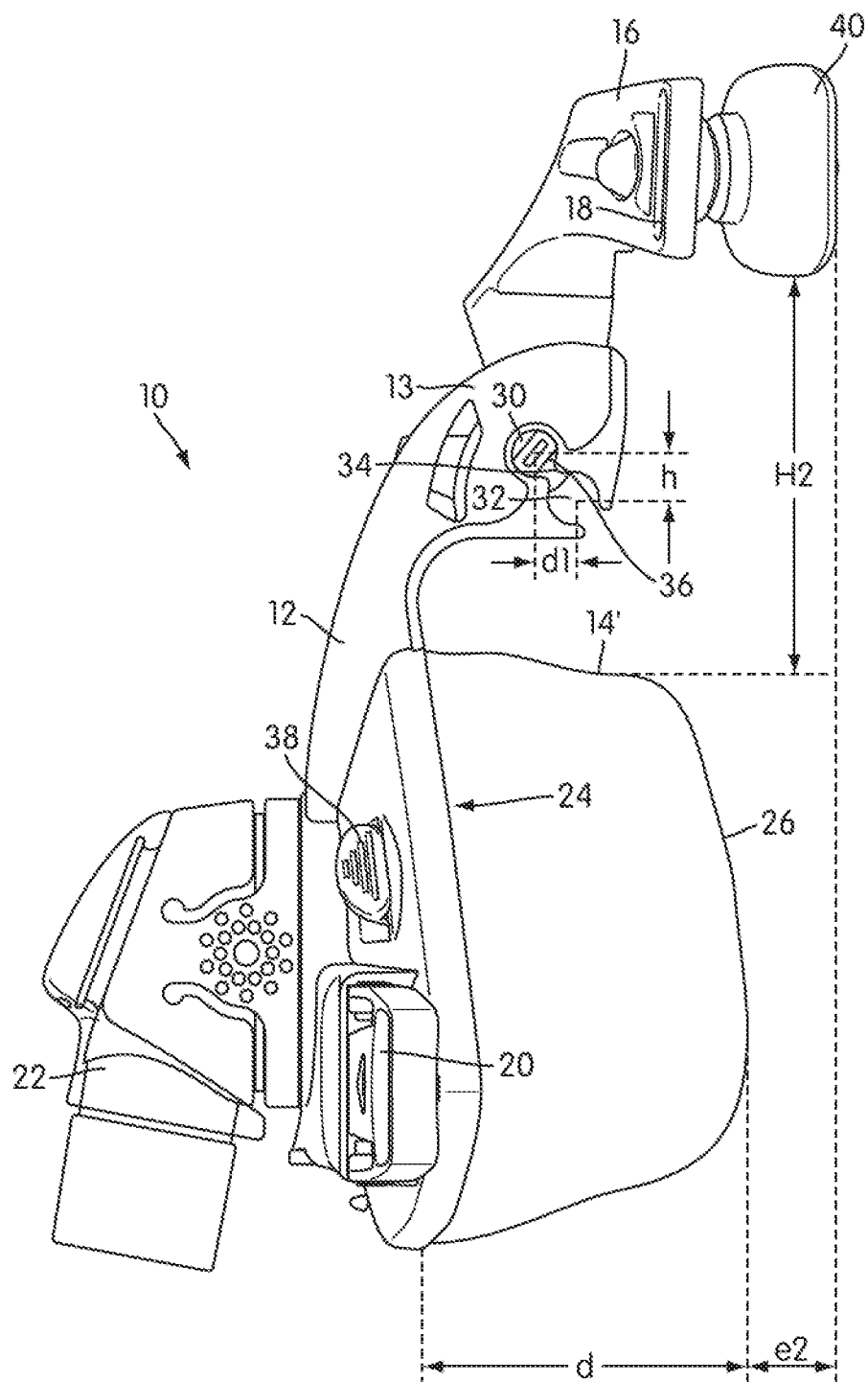
FIG. 2 is a similar side view thereof in a second position.

In one form of the embodiment shown in FIGS. 1 and 2, the mask assembly is provided with two individual forehead supports 16, one for each of the two positions shown therein. With the first forehead support, the shaft 36 is positioned further away from the adjustment mechanism, e.g., a tongue and groove or ratchet mechanism, as shown in FIG. 1. With the second forehead support, as shown in FIG. 2, the shaft 36 is positioned closer to the adjustment mechanism. In another form, the shaft 36 may be adjustably mounted with respect to the adjustment mechanism (ratchet assembly). For example, shaft 36 could be movably attached (e.g., via pivoting, sliding or the like) to a lower leg portion of the "T" shaped forehead support 16, so as to allow movement of the shaft 36 relative to the ratchet mechanism, for selective seating within one of the two slots 30 or 32. Alternatively, a different retaining mechanism could be employed, such as a friction fit or screw thread, etc.

Figure 2A:
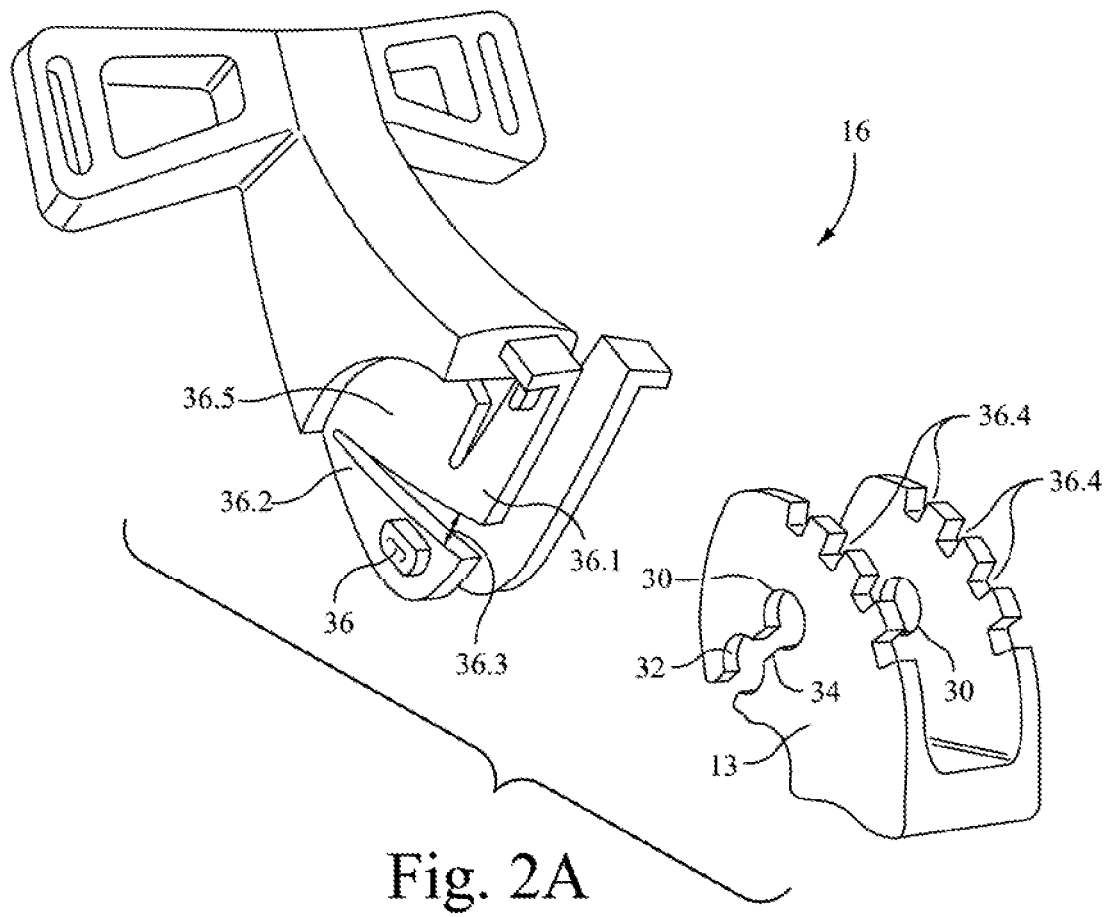
FIG. 2A is a partial exploded view of a forehead support assembly according to yet another embodiment of the present invention.

As shown in FIG. 2A, forehead support 16 includes an adjustment mechanism similar to that described in U.S. Pat. No. 6,532,961, incorporated herein by reference in its entirety. The adjustment mechanism in FIG. 2A is slightly different than that used in FIGS. 1 and 2. However, one would recognize that the following teachings are equally applicable to either adjustment mechanism. The forehead support includes structure allowing movement between shaft 36 and main arm portion 36.1. In this embodiment shaft 36 is mounted on a movable arm portion 36.2, e.g., in a living hinge, joint, pivot, etc. Movable arm portion 36.2 can move toward and away from main arm portion 36.1, depending on whether shaft 36 is to be seated within slot 30 or 32. In this way, proper engagement between teeth/recesses 36.4 and positioning pin 36.5 can be maintained. A spring 36.3 or other resilient member may be provided to bias arm portion 36.2 towards or away from main arm portion 36.1.

Referring back to the embodiment of FIGS. 1 and 2, the position of the shaft 36 can be changed from the second slot 32 to the first slot 30. For example, the forehead support 16, along with each shaft 36, may be rotated in a clockwise direction (as seen in FIG. 1) until the narrower dimension of each shaft 36 aligns with keyway 34. Upon alignment, the forehead support 16 and shafts 36 can be moved, e.g., slid, in the direction towards the first slot 30, until the full extent of the shaft 36 is located in the first slot 30. Thereafter, the forehead support 16 along with each shaft 36 are rotated in a counterclockwise sense until the forehead support 16 is in a position facing the patient's forehead, in which position the wider side of each shaft 36 prevents its release from the first slot as the key way 34 is more narrow than the wider side of each shaft 36.

FIG. 2 shows shaft 36 in position within the first slot 30. In addition, it can be seen that the cushion 14 from FIG. 1 has been replaced with another cushion 14', which is identical in all ways except the cushion 14' does not include a gusset. Instead, the cushion 14' may be a standard Mirage® cushion available from ResMed, Ltd., modified to include a non-face contacting side which will interface with frame 12 and cushion clips 38.

Without a gusset, cushion 14' has a dimension d which is less than dimension D in FIG. 1. As such, the position of forehead support 16 relative to the upper portion 13 of the frame 12 is changed, due to movement of the forehead support 16 and shaft 36 to the first slot 30. Therefore, the relative distance e1 and e2 between the cushion 40 of forehead support 16 and the face-contacting portion 26 of the cushion 14, 14', respectively, remains substantially constant. In other words, e1 and e2 (the horizontal offset between the forehead support and the cushion) are substantially the same, even though the forehead support 16 has been moved. Moreover, the forehead support 16 can be moved a distance d1, which is approximately the same thickness of the gusset portion 28, or the difference between D and d. Accordingly, the forehead cushion 40 and face-contacting portion 26 in each of FIGS. 1 and 2 will contact the patient in approximately the same location, such that the positioning, fit and/or feel of the mask 10 with either of cushions 14, 14' is substantially the same.

In this example, the two slots 30, 32 are arranged somewhat diagonally, which in practice may also have the effect of changing the height h of the forehead support 16 relative to the cushion 14, 14'. In particular, the height H1 between the forehead cushion 40 and the cushion 14 in FIG. 1 may be less than the height H2 between the forehead cushion 40 and the cushion 14' in FIG. 2. However, the heights H1 and H2 can be dimensioned to be the same, in which case, for example, the slots may be located horizontally side-by-side, or the height H2 can be less than height H1, if desired, depending on application.

Moreover, the forehead support 16 can be moved between the slots 30, 32 for the purpose of changing the contact profile between the cushion 40 and the patient's forehead, while keeping the same cushion, e.g., cushion 14 or cushion 14'. In other words, it is not necessary to change the cushion and to make use of the added adjustability. To this end, there are numerous arrangements which can allow the position of the forehead support 16 to be altered with respect to the upper portion 13 of the frame 12. Also, the number of slots can be changed in accordance with the number of different positions which are necessary to accommodate cushions having various depths D or d, or d to D. There may be a predetermined number of fixed positions, e.g., three to five, or more, or there may be an infinite number of positions made possible by a sliding arrangement, for example.

In one embodiment, the frame 12 may be sold with a Mirage®-type cushion 14', in which case the cushion frame 16 would be positioned as shown in FIG. 2. If preferred, the patient can upgrade to a gusseted cushion 14 as shown in FIG. 1, in which case the shafts 36 would be repositioned from the second slots 32 into the first slots 30, as shown in FIG. 1.

Figure 3:
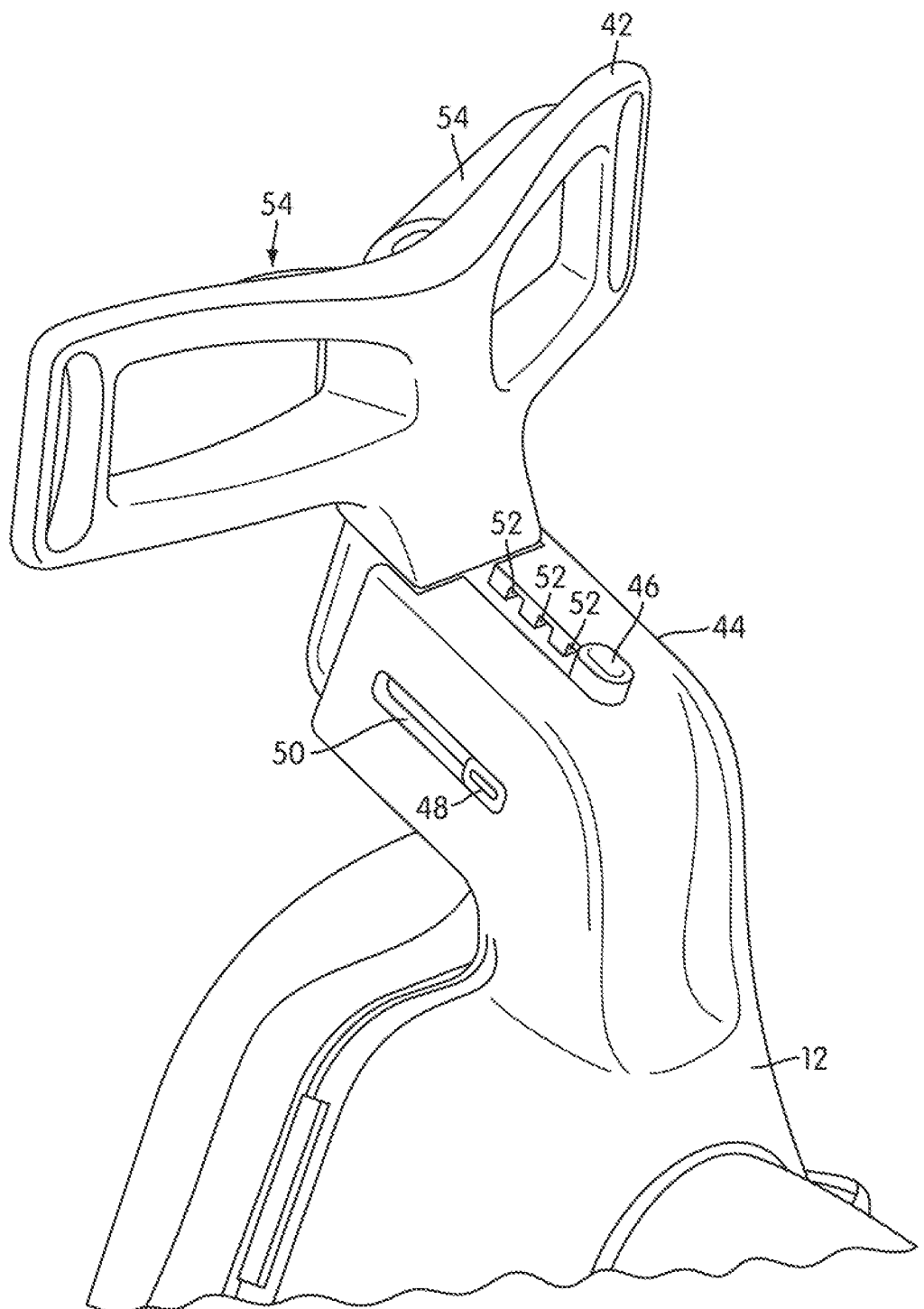
FIG. 3 is a partial perspective view of a mask assembly illustrating an alternative embodiment of the present invention.

FIG. 3 shows a sample of a forehead support 42 which is slidable with respect to an upper part 44 of a frame 12. In this example, the forehead support 42 is not pivotable, rotatable or otherwise movable to change the angular attitude of the upper part 44 relative to the patient's forehead, although provision could be made for this as well. The forehead support 42 is provided with a finger-operated push button 46, e.g., only a single finger-operated push button, which is resiliently urged or locked in a first position in which the forehead support 42 is prevented from moving relative to the upper part 44 of frame 12. When the button 46 is depressed, the forehead support 42 is free to move, or it can be spring biased to move towards and/or away from the patient's forehead, to effect a relative change in position due to the different facial geometries among patients, or to simply compensate for the change between a cushion with a gusset and a cushion without a gusset or a cushion having a greater profile depth. The forehead support 42 may be supported and guided by a pair of pins or extensions 48 which are positioned within slots 50 provided on the upper part 44 of frame 12. The push button 46 may be associated with one or more tabs which can be selectively positioned in one of a plurality of slots 52, in this case four slots. However, the cushion frame 16 and the upper part 44 can be structured to be fixed relative to one another via friction, such that an infinite number of relative positions can be achieved. The forehead support 16 may be provided with one or more cushions 54.

Figure 4:
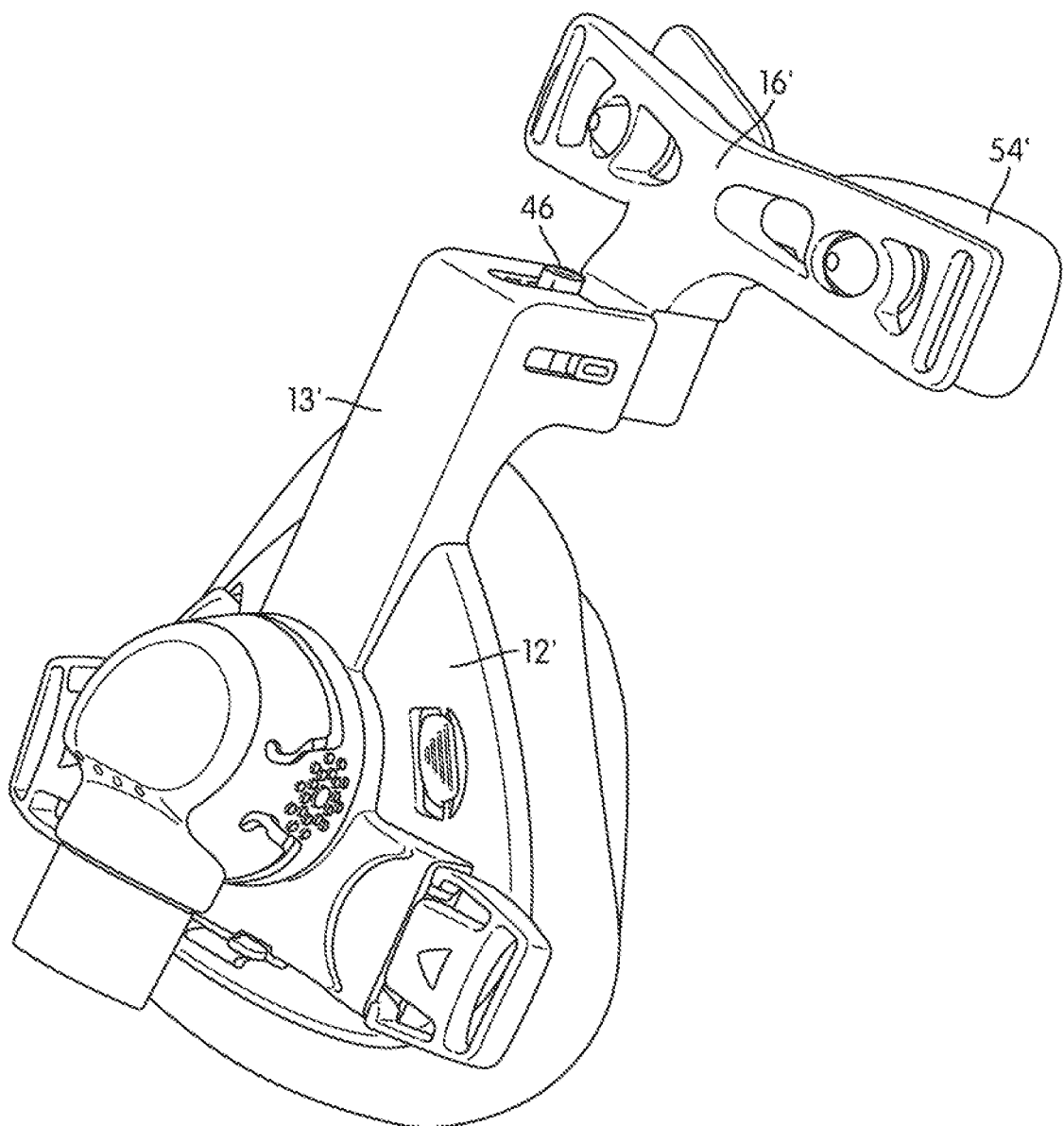
FIG. 4 is a perspective view of a mask assembly illustrating a further embodiment of the present invention.

FIG. 4 illustrates yet another embodiment of a mask, like that shown in FIG. 1, but which includes a push button arrangement to allow for horizontal movement of the forehead support 16' relative to the patient's forehead, to accommodate for different cushion depths or for patient's having differing facial geometries. Like elements have been used to denote like parts.

Cushion Alternatives

Figure 5:
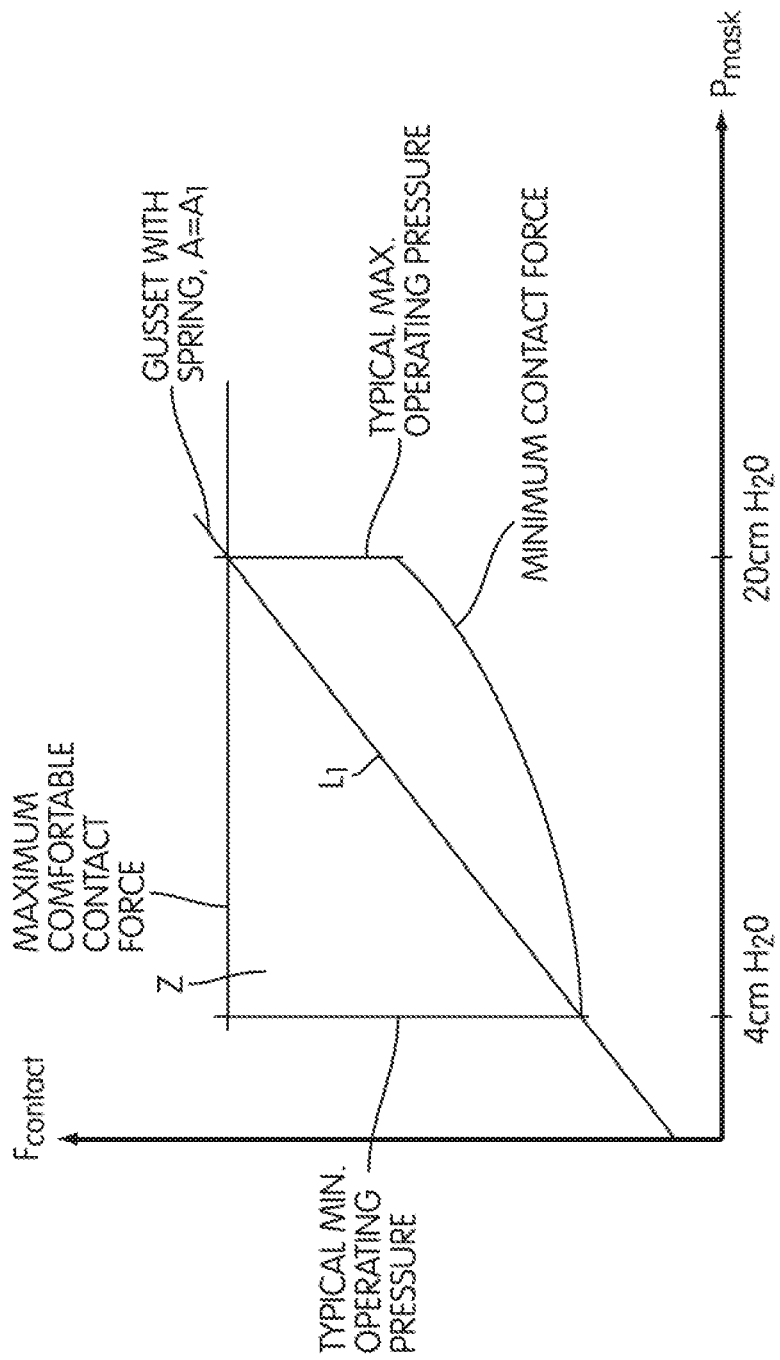
FIG. 5 is a graph that illustrates the relation between mask pressure and contact force on the patient's face for a mask with a gusset and/or spring portion.

FIG. 5 plots mask pressure (Pmask) versus contact force of the mask cushion against the patient's face (Fcontact). A mask designer ideally wants to create a mask which falls within a zone Z of comfort and seal. The zone Z is bounded on four sides. The upper and lower sides represent maximum comfortable contact force and minimum contact force, respectively. Below the minimum contact force, a proper seal will not be maintained, while forces above the maximum comfortable contact force will be undesirable from the patient's perspective. The left and right side borders of the zone Z represent the typical minimum and maximum operating pressures of the mask, respectively. For example, the mask may operate with pressures in the range of about 4-20 cm $H_2O$, although other pressures are contemplated.

Line L1 is the performance curve for one example of a mask described in U.S. application Ser. No. 09/885,455 or Ser. No. 10/655,622. The mask includes a cushion with a gusset having an increased projected area A1, compared with the contact area A of the cushion on the patient's face.

The cushion, e.g., the gusset, may include a spring portion to help maintain the performance curve within the zone Z. The effect of the spring portion is to provide an additional contact force at low mask pressures when the effect of the gusset portion is insufficient to provide the minimum sealing force. As a result, the cushion maintains a seal through the range of operating pressures. Moreover, the cushion represented by line L1 falls within the zone of comfort and seal Z throughout the range of operating pressures.

Thus, for example, by combining a gusset portion with a spring structure in a cushion, a designer can tailor the contact force of the cushion such that it falls within the zone of comfort and seal Z throughout the working range of pressure. The same principles may be applied for different pressure ranges.

Further, the size of the zone Z may change (e.g., by changing the maximum comfortable contact force) depending on a particular region of the patient's face. For example, the maximum comfortable contact force may be reduced for a nasal bridge region of the face. As a result, the cushion can be tailored for that particular region such that it falls within the zone of comfort and seal Z throughout the range of operating pressures.

Another example is that the upper side of the zone Z is in fact a straight line as this is the maximum force that the face can take without damage to the skin occurring. However, the maximum force for which the user is comfortable may be below this line. Indeed the upper side of the zone may be a sloping line, indicating a low maximum comfortable force at low pressure leading up to a higher maximum comfortable force at high pressures.

Although the cushion 14' in FIG. 2 does not include a gusset portion, it can nonetheless be provided with structure and/or a configuration allowing it to incorporate one or more features or advantages associated with a cushion having a gusset portion. In particular, there are a number of masks currently on the market today which can be modified, sometimes in minor ways, to achieve at least one or more of the benefits of a mask with a gusset and/or spring portion. For example, currently existing mask systems can be modified to keep the contact force within zone Z for a given pressure range and/or a specific portion of the patient's face. In some cases, these modifications may not include the use of a gusset and/or spring portion.

Figure 6:
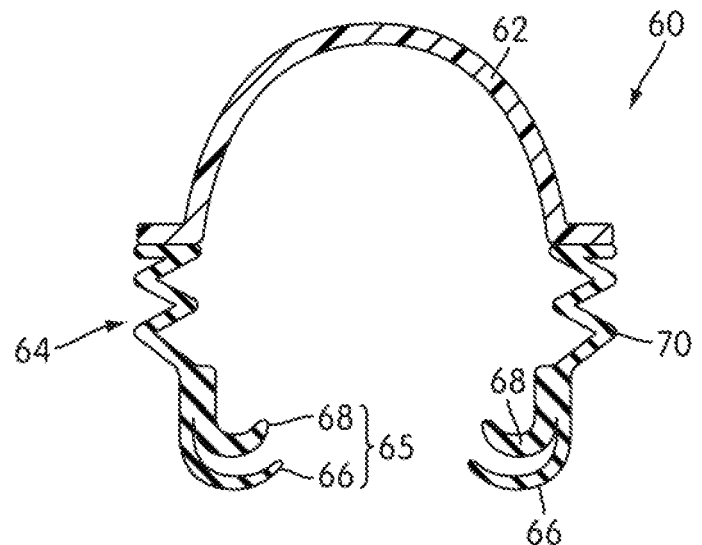
FIG. 6 is a schematic view of a mask according to an embodiment of the present invention.

FIG. 6 illustrates a schematic view of a first cushion embodiment of the present invention. A mask assembly 60 includes a frame 62 and a cushion 64. The cushion may include a face contacting portion 65 that is adapted to contact with a portion of the patient's face, or at least interact with the patient. Moreover, face contacting portion, as used herein, does not require any contact with the patient's face so long as a sealed interface is established with the patient's airways. Portion 65 includes a membrane 66 spaced above an underlying rim 68. The face contacting portion 65 may be mounted on a concertina-type connecting structure 70 that is configured or structured to provide a spring-like effect. Connecting structure 70 forms a bridge or transition between the contacting portion 65 and frame 62. For example, the connecting structure 70 may include a wire insert. Alternatively, or in addition, the connecting structure 70 may comprise an elastomeric and/or a plastic spring.

Figure 7:
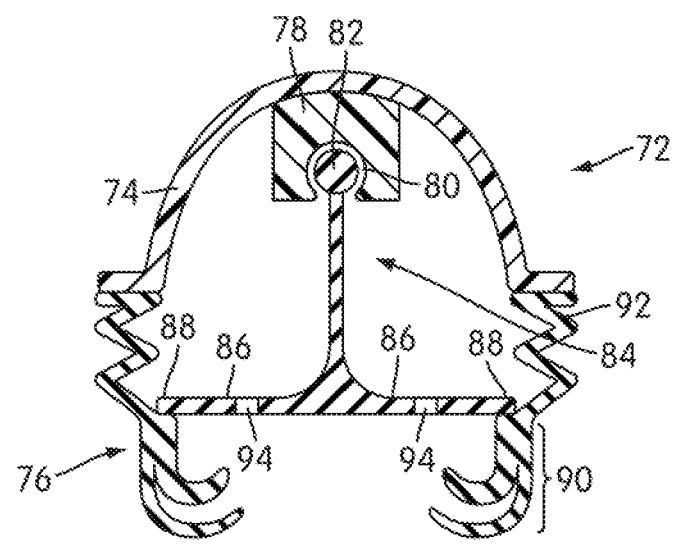
FIG. 7 is a schematic view of a mask according to a further embodiment of the present invention.

FIG. 7 shows a schematic view of another embodiment of a mask assembly 72 which includes a frame 74, and a cushion 76. The frame 74 includes a mount 78 provided or fixed to an inside surface of the frame 74. The mount 78 includes a receiving aperture 80 to receive an end 82 of a spring 84, e.g., an elastomer spring. The end 82 may be in the form of a ball joint which is received in aperture 80, which may be at least part sphere shaped. End 82 is structured to pivot to allow face contacting portion 90 to move sideways relative to frame 74, thereby increasing performance in the event the frame is "bumped." Spring 84 may have a generally T-shape, with arms 86 extending laterally and having an end 88 provided or connected to each side of face contacting portion 90. In this case, connecting structure 92 may be structured without a spring like effect, in which case the spring effect is supplied solely by the springiness of spring 84. In an alternative, the connecting structure 92 may include a spring wire or be made of a plastic or elastomeric spring, as described above. The spring constants of the connecting structure 92 and the spring 84 should be coordinated to provide the most optimum spring and dampening characteristics. Spring 84, e.g., arms 86, may include one or more apertures 94 which allow for the passage of gas.

Figure 7A:
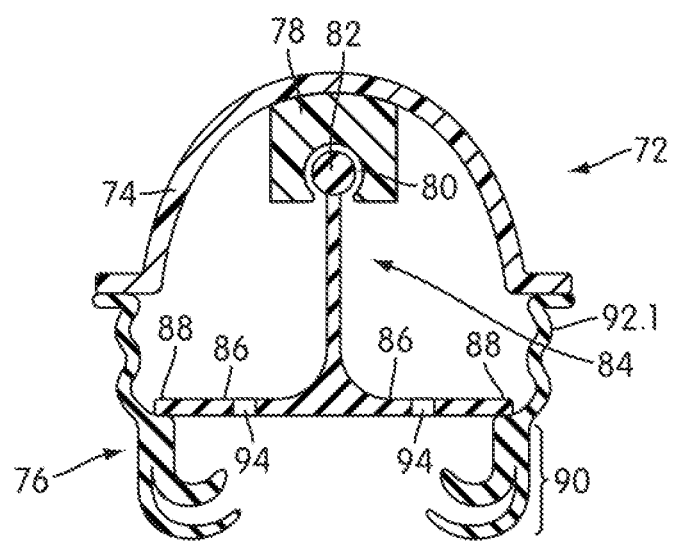
FIG. 7A is a schematic view of a mask according to another embodiment of the present invention.

As shown in FIG. 7, connecting structure has generally fully developed pleats or folds in connecting portion 92. However, the cushion need not be fully pleated. For example, as shown in FIG. 7A, the connecting structure 92.1 includes gradual pleats that can include indents that cause the cushion to fold under deformation force.

Figure 8:
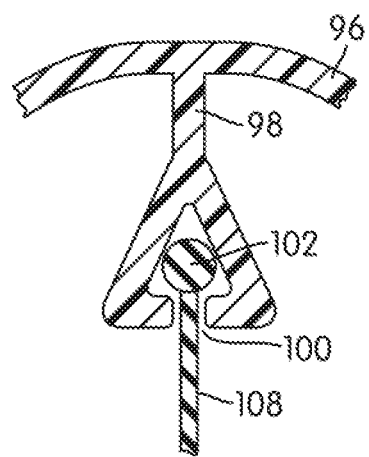
FIG. 8 is a partial schematic view illustrating an alternative embodiment of the present invention.

FIG. 8 shows a partial schematic view of an alternative embodiment. In this embodiment, frame 96 includes a mount 98 having an aperture 100 to receive an end 102 of a spring member 108, like that described above.

Figure 9:
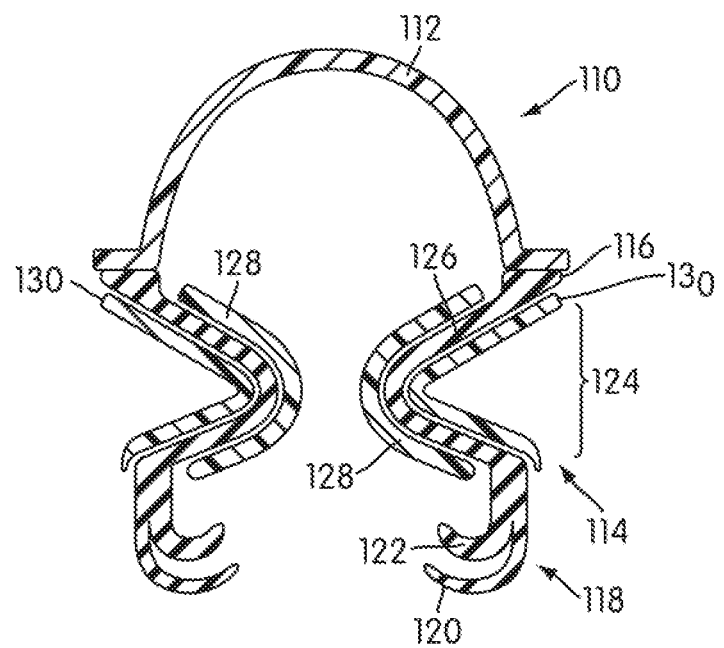
FIG. 9 is a schematic view of yet another embodiment according to the present invention.

FIG. 9 illustrates a schematic view of a mask assembly 110 including a frame 112 and a cushion 114 provided to the frame 112. The cushion 114 includes a non-face contacting portion 116 oriented towards the frame 112, and a face contacting portion 118 having a membrane 120 and an underlying rim 122. The cushion 114 includes a central portion 124 located between the non-face contacting and face contacting portions 116, 118 of the cushion 114. The central portion 124 in this example includes an inverted portion 126 that extends inwardly towards the nose receiving cavity. Inverted portion 126 provides for a similar level of flexibility and travel as an external gusset but covers less area on the face, e.g., it has a smaller footprint or projected area, which is perceived as less obtrusive by the patient. The inverted portion 126 may be provided with a wire spring embedded within the wall thickness, or the inverted portion 126 may be made of a plastic or elastomeric material having a spring constant that can be selected based on the desired operating characteristics. Moreover, spring may have a fixed or variable spring rate.

The inverted portion 126 may include an internal spring member 128, and/or an external spring member 130. The spring members can be made of plastic or metal. The internal spring member 128 may be a compression spring, while the external spring 130 may be leaf or tension spring. Springs 128, 130 can be manufactured with a predetermined generally V-shape or U-shape.

Spring member 128 can be assembled with cushion by sliding the spring member 128 on the inside of the cushion, until it reaches the inverted portion 126. The spring member 130 can be assembled with cushion by sliding the spring member 130 on the outside of the cushion, until it reaches the inverted portion 126. Alternatively the spring members can be split and connected as they are assembled onto the cushion. The ease of assembly allows different springs to be used by different users. Therefore the allowed travel, flexibility and spring stiffness can be tailored to patient preference, seal requirements or a particular pressure range. When in position, the spring members 128, 130 can be maintained in position by friction, and/or an adhesive. If one or both of spring members 128, 130 are used, then it is not necessary that the inverted portion 126 have spring resiliency. In this case, the system simply bottoms out (at low pressures) if at least one of the springs 128, 130 is not used. In another embodiment, a plurality of spring members, shaped like spring members 128, 130, can be provided with various spring rates.

Figure 9A:
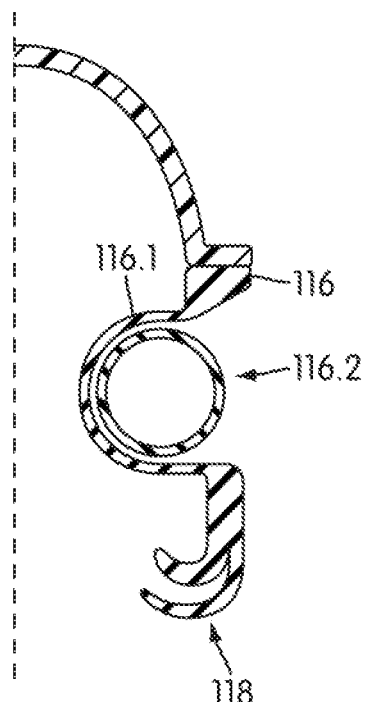
FIG. 9A is a partial schematic view of a cushion according to yet another embodiment of the present invention.

FIG. 9A shows a further embodiment. Provided to the non-face contacting portion 116 is a thin arcuate or circular section membrane 116.1 which in turn attaches to face contacting portion 118. This thin membrane 116.1 acts as a receiving channel for an inflatable tube 116.2. This tube acts as a spring and may be inflated or deflated by means of a valve to vary the spring stiffness.

Figure 9B:
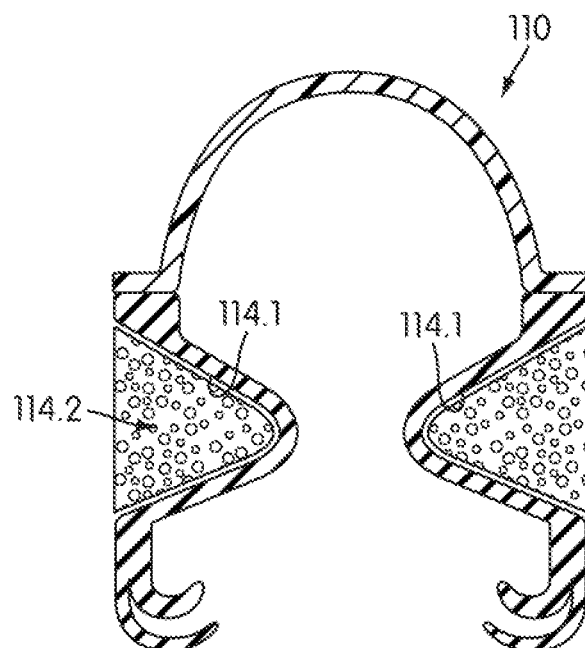
FIGS. 9B and 9C are schematic views of another embodiment of the present invention.
Figure 9C:
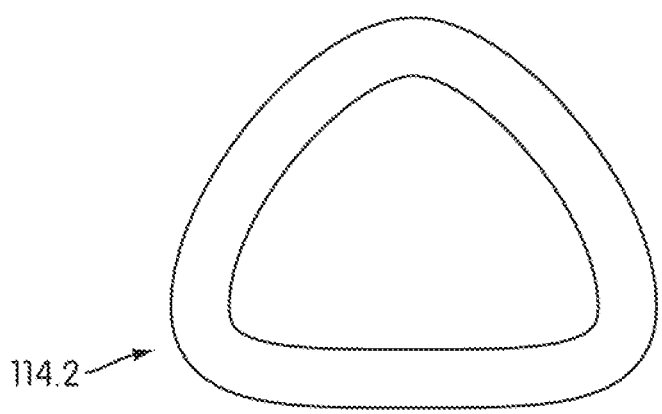

FIG. 9B illustrates an embodiment like that shown in FIG. 9, but does not include spring members 128, 130. Instead, mask assembly 110 has a cushion 114 that includes a groove 114.1 structured to accommodate an insert 114.2. Insert may be an open or closed cell foam, or it may be a spring foam, i.e., one molded in a spring shape. In an alternative, the insert 114.2 could be a gel filled member. The insert in isolation is shown in FIG. 9C. Insert 114.2 is structured to provide a spring effect to cushion 114. Insert 114.2 is not provided in the air path to the patient, but rather is positioned within a groove on the outside of the cushion.

Figure 10:
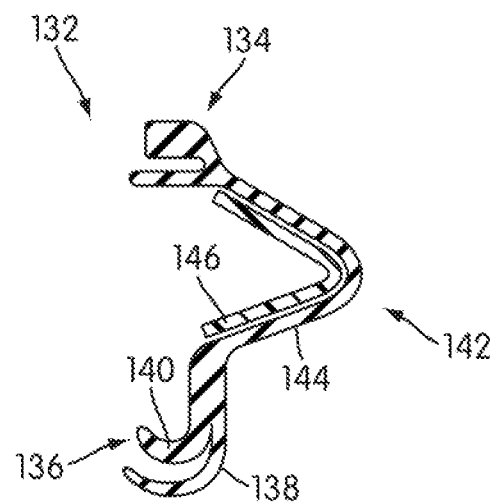
FIG. 10 is a partial schematic view of still another embodiment according to the present invention.

FIG. 10 is a partial schematic view of another embodiment, shown without a frame. Cushion 132 includes a non-face contacting portion 134 structured to be attached to or otherwise provided to a frame. A face contacting portion 136 includes a membrane 138 and an underlying rim 140, similar to that previously described. A central portion 142 provided between the non-face contacting and face contacting portions 134, 136 includes a gusset portion 144. An internal spring 146, e.g., a leaf spring, an elastomer, a plastic and/or a composite spring, is provided on the inside of the cushion 132. The internal spring 146 can be inserted inside the cushion until it reaches the gusset portion 142, at which point the spring 146 is maintained in place via friction, glue, and/or other appropriate fastener mechanisms. In the alternative, spring 146 can be formed with central portion 142 in an over-molding process.

In the embodiment of FIG. 10, the cushion can be a standard Mirage®-type cushion, which does not include a gusset portion 144. However, the spring 146 can be arranged such that it pushes out the side wall of the cushion between the portions 134, 136, thereby creating or forming the gusset portion 144. Similarly, the springs 128, 130 in the embodiment of FIG. 9 can be used to create the inverted portion 126, in the event the side walls of the cushion are relatively straight before the insertion of a spring member.

In yet another alternative, the cushion 110 may be provided with the inverted portion 126, and a spring insert like spring member 146 can be inserted inside the cushion, to evert the inverted portion 126 until it assumes an external gusset like configuration, like that shown in FIG. 10. Conversely, the cushion may start out in the everted state, as shown in FIG. 10, and a spring member like spring member 130 in FIG. 9 can be provided on the outside of the cushion, to convert the gusset portion 144 into an inverted portion as shown in FIG. 9.

In the event the cushion is to include a central portion which is to change shape, e.g., everting or inverting, the cushion should be structured such that the inverted and everted positions are stable. Such can be accomplished by allowing one or both ends of the central portion of the cushion to bend, flex and or pivot relative to the other portions of the cushion. The apex of the inverted or everted portion should be structured and/or its materials selected such that it can allow for inversion or eversion. Initially, the central portion will resist such movement, but beyond a certain limit, the central portion will flip from the inverted position to the everted position, or vice versa. In this way, the cushion is stable in the inverted and everted positions, generally resisting large movement, but at the same time can be everted or inverted upon the application of sufficient force not normally encountered during use of the mask system. The use of a spring member will help to resist inadvertent flipping, especially for preventing inverting movement, although a spring is not necessary to prevent either inverting or everting of the cushion.

Figure 11:
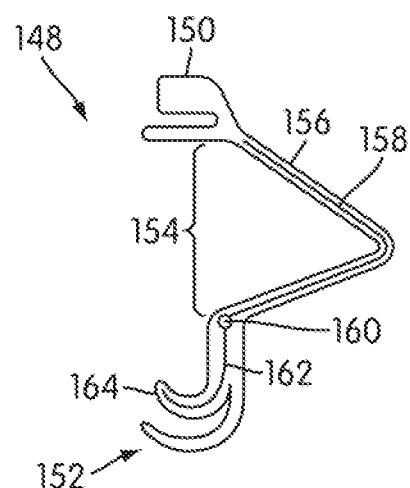
FIG. 11 is a partial schematic view of a further embodiment according to the present invention.

FIG. 11 is a partial schematic view (without cross-hatching for clarity) of a cushion 148 according to another embodiment. Cushion 148 includes a non-face contacting portion 150, a face contacting portion 152, and a central portion 154 between the portions 150 and 152. Central portion 154 includes a protruding gusset portion 156. A skeleton, e.g., a spring member 158, may be provided within the wall thickness of at least a portion of the gusset portion 156. A skeleton may include a malleable wire rim or bead 160 provided around at least a portion of the circumference of the cushion. A prong rim, or lip 162 may be provided within underlying rim 164, to help maintain its shape.

FIG. 12 is a partial top schematic view showing a cushion 166 including gusset portions 168 located at one and preferably all three apices of the cushion 166. Flexible folds or a spring 170 are provided along at least the cheek regions 172 of the cushion. These folds allow a similar level of flexibility and travel (away from the face) as the gusset portions 168 but do not incorporate the increased area. It can be seen that the total area of the gusset around the mask has been reduced, thus helping to increase visibility. The sealing force of the cushion may be provided entirely from the gusset portions 168 or may also include some spring force from portions 170. Moreover, portions 170 and 170.1 may be in the form of relatively rigid beams. The gusset portions 168 may also incorporate some spring force.

FIG. 13 illustrates a partial schematic view of yet another embodiment of a cushion 174 according to the present invention. Cushion 174 includes a non-face contacting portion 176 adapted to be connected to or otherwise provided to the frame (not shown in FIG. 13). Portion 176 is preferably made of a material having a spring effect, such as polypropylene, or another semi-rigid material such as polyurethane—one that will resiliently maintain its general shape, but which will provide some degree of spring effect upon the application of pressurized gas under variable pressure to the mask, tightening of the head straps, etc. Portion 176 extends outwardly away from the end where it is connected to frame, to an intermediate portion that includes a transition region 179 which is where the relatively more rigid and elastic materials are joined. Portion 180 may include a membrane 182 and an underlying rim 184, which share a common side wall 183, as described above. A projected area 181 is defined between the end of the transition region 179 and a mid-point 182.1 of membrane 182. As shown, the projected area 181 extends outside the area of contact 185 between membrane 182 and the patient. Pressure acts on this additional area leading to the application of a force to the membrane 182 and underlying rim 184. Portion 180 is preferably made of a material that is softer than the semi-rigid material of the non-face contacting portion 176. Transition 178 may include a rigid connection between the semi-rigid and compliant materials of portions 176, 180, respectively. Alternatively, the transition region 178 may include a hinge, e.g., a living hinge (e.g., polypropylene) or an axle hinge, or the parts may otherwise be co-molded and allowed to move relative to one another by flexing or bending relative to one another.

FIG. 13A shows another embodiment which is similar to the embodiment of FIG. 13, but which add a spring portion 180.1.

Figure 14:
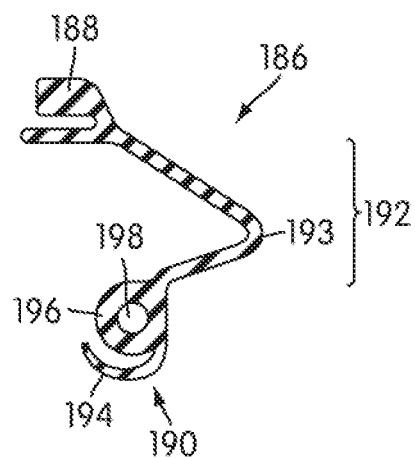
FIG. 14 is a partial schematic view of still another embodiment of the present invention.

FIG. 14 illustrates a partial schematic view of still another embodiment according to the present invention. A cushion 186 includes a non-face contacting portion 188, a face contacting portion 190 and a central portion 192 located generally between the portions 188, 190. Central portion 192 includes a gusset portion 193, like that described above. Face contacting portion 190 includes a membrane 194 and an inflatable chamber 196 provided below the membrane 194. Inflatable chamber 196 forms an underlying rim and includes a channel 198 that is filled with air or another suitable fluid, such as gel and/or soft durameter elastomer. The stiffness of chamber 196 can be changed depending on the pressure of the medium contained therein, or the pressure can be fixed at a predetermined range or level. The stiffener also depends on the material make-up of chamber 196.

Figure 15:
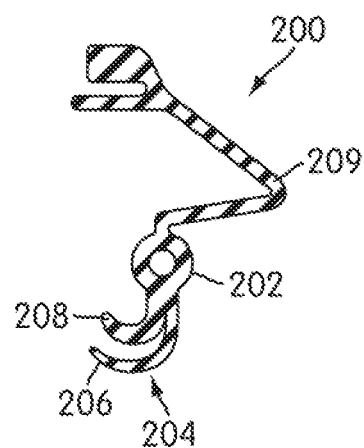
FIG. 15 is a partial schematic view of another embodiment of the present invention.

FIG. 15 discloses another embodiment of a cushion 200 having an elastic cuff 202. The elastic cuff is provided between face contacting portion 204, including membrane 206 and rim 208. Advantages of the elastic cuff are described in U.S. Non-Provisional patent application Ser. No. 10/655,622 filed Sep. 5, 2003. In FIG. 15, the elastic cuff 202 can be used in conjunction with a gusset portion 209.

The chamber 196 (FIG. 14) or elastic cuff 202 (FIG. 15) provides a spring or spring-like effect. The spring should be of comparative stiffness to that provided as the gusset is compressed at a pressure. Thus, the chamber/cuff plus gusset provides additional force when the gusset is compressed. This force is provided without increasing the area of the gusset, which is less obtrusive to the patient. This helps provide a force at low pressures such as 4 cm $H_2O$ to allow the performance to fit within the zone Z (FIG. 5). Because this force does not increase proportionally with pressure (as does the force provided by gusset area), the increase is not as significant at high pressures as it would have been if the gusset area had been increased to try and fit within zone Z. Compare, e.g., FIG. 43 of U.S. Non-Provisional patent application Ser. No. 10/655,622.

Figure 16A:
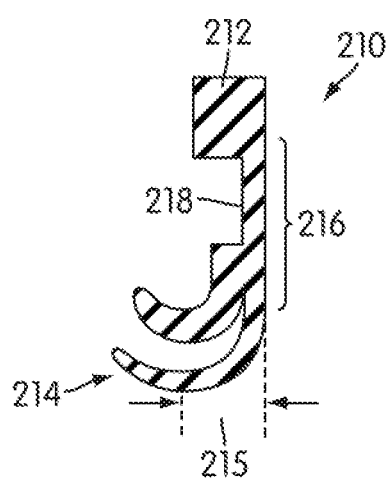
FIGS. 16A and 16B are partial schematic views illustrating a further embodiment of the present invention.

FIG. 16A illustrates a partial schematic view of a cushion 210 according to yet another embodiment of the present invention. Cushion 210 has a non-face contacting portion 212 adapted to be connected to or otherwise provided to a frame (not shown in this view). Face-contacting portion 214 is provided at the other end of cushion. A central portion 216 is provided between the portions 212 and 214. Central portion 216 includes a side wall portion, e.g., a thin walled section 218, which may take the form of one or more cut-outs, grooves or areas of predetermined weakness, e.g., one or more portions subject to deformation and resilient restoration of their shape. The side wall or thin walled section 218 may resiliently deform, buckle or flex upon donning of the mask and/or with changes in air delivery pressure and/or strap tension, in which case the cushion would form an improvised gusset portion. The thus formed gusset portion in the side wall can be converted back into a substantially straight wall section when the force and/or pressure is removed.

Figure 16B:
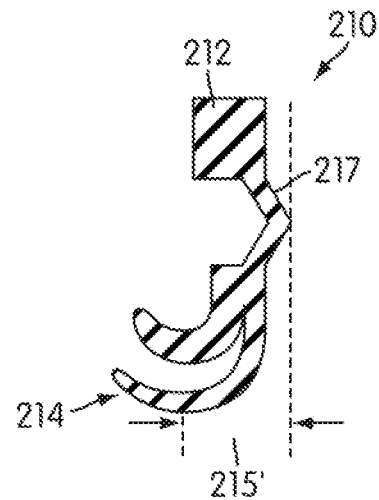

In the position shown in FIG. 16A, a projected area 215 extends from the center point of membrane 214 to the outer surface of side wall. If sufficient force is provided to the central portion, the side wall of the central portion 216 will extend or buckle outwardly, as shown in FIG. 16B to form an increased projected area 215'. In the position shown in FIG. 16B, projected area 215' of the improvised gusset portion 217 extends outward and defines a projected area that is greater than projected area 215. Pressure acts upon this additional area effectively increasing the sealing force. This is more likely to occur at low pressures when the force on the mask due to pressure is low and thus the strap tension can deform the cushion. At high pressures, the increased force on the mask due to pressure is more likely to cause the headgear straps to move or extend and thus the side wall will assume the general posture shown in FIG. 16A, in which case there is little or no projected area or stored spring force, meaning that sealing force is maintained by strap tension that opposes the gas delivery pressure tending to move or lift the mask away from the face.

This design acts as a spring under relatively light load and has gusset-like effect at higher pressure, thereby providing a variable effect. The spring becomes weaker when bent, which helps form a gusset which increases sealing force.

Figure 16C:
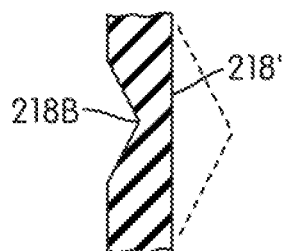
FIGS. 16C and 16D are additional embodiments of the present invention.
Figure 16D:
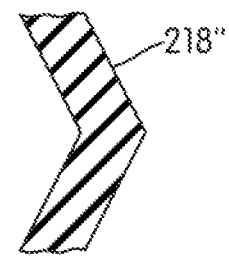

FIG. 16C illustrates yet another embodiment in which wall 218' has a variable thickness, e.g., created using a notch 218B. This will cause wall 218' to collapse at the weakest point, to add predictability. FIG. 16D is yet another embodiment in which side wall 218" is pre-formed at an angle, to encourage buckling outward or inwards, as desired.

Figure 17:
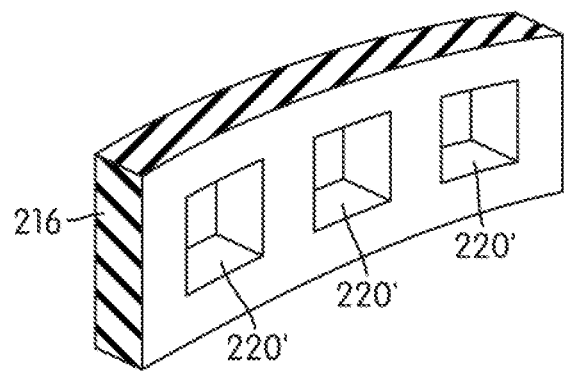
FIG. 17 illustrates a partial cross-sectional view of a cushion wall section according to the present invention.

FIG. 17 shows a partial, schematic perspective view according to a variation of the embodiment in FIGS. 16A and 16B. Central portion 216 is provided with a plurality of cut-outs 220' to provide predetermined areas of weakness which may flex or buckle to provide one or more of the advantages described. Central portion 216 could be in the form of an adapter that is provided to the non-face contacting portion of a standard or conventional cushion. Cut-outs 220' are preferably not in the form of thru-holes, but rather are in the form of blind-bore apertures.

The contact force applied to the patient's face can be tailored by adjusting a wall thickness of central portion 216. The central portion acts as a spring structure to provide a component of the contact force on the patient's face through the membrane 214. Central portion 216 may have a uniform wall thickness with a thin cross-section. The central portion may have a thicker cross-section, with the thinner wall providing a smaller component of force than the thicker wall. The cross-section of the wall may vary around the perimeter of the gusset portion 217. For example, a gusset portion may have a thin wall in the patient's nasal bridge region, but a thicker wall in the patient's cheek region. Moreover, the wall of central portion may be varied in conjunction with the desired maximum projected area 215, for example, by increasing the thickness of the wall to result in a reduced projected area 215.

Figure 18A:
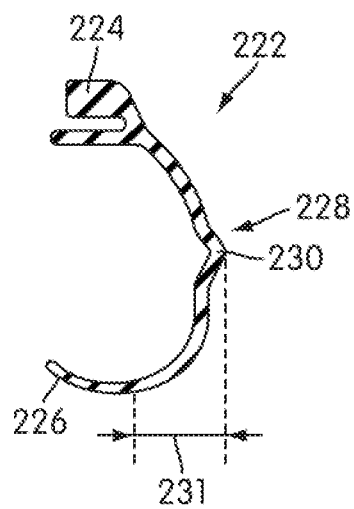
FIGS. 18A and 18B are partial schematic views illustrating a further embodiment in accordance with the present invention.
Figure 18B:
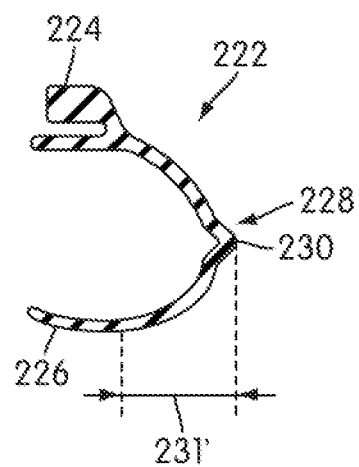

FIG. 18A is yet another schematic drawing depicting a cushion 222 according to a different embodiment. Cushion 222 includes a non-face contacting portion 224 structured to be attached or otherwise provided to a cushion frame (not shown in this figure). A face contacting portion 226, in this example having only a single membrane, can be provided opposite the non-face contacting portion 224. A central portion 228 between the portions 224, 226 may include a buckle region 230. Depending on the pressure inside the mask and the strap tension, buckle region will allow the central portion 228 to flex, bow or move outwardly, to thereby effect a change in the projected area of the cushion on the face. This in turn changes the force applied to the face contacting portion 226. FIG. 18B shows the cushion in such a position, including an increased projected area 231'.

Figure 19A:
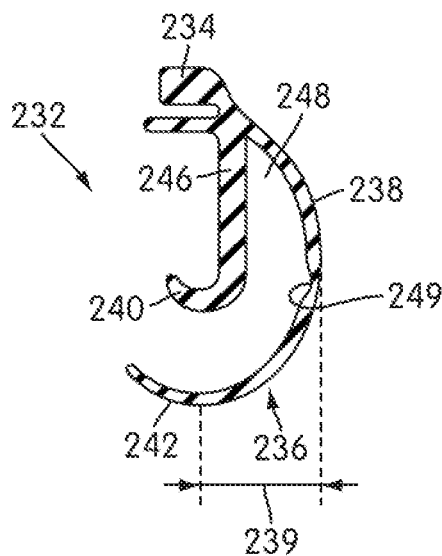
FIGS. 19A and 19B illustrate partial schematic views of still another embodiment according to the present invention.
Figure 19B:
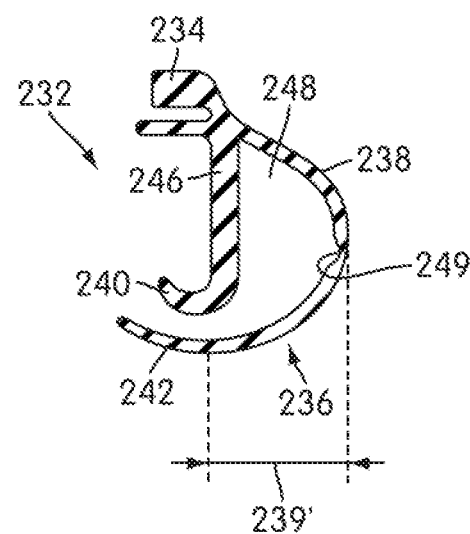

FIG. 19A is a partial schematic view of a cushion 232 according to still another embodiment of the invention. Cushion 232 includes a non-face contacting portion 234, a face contacting portion 236 and a central portion 238. A rim 240 may be positioned below a membrane 242 of portion 236, although it is not necessary. The membrane 236 branches away from rim support 246, and has a relatively rounded outer wall profile. A space 248 is created between the outer side of the rim support 246 and the inner side of the membrane. With this structure, the membrane 242 and central portion 238 may more easily flex, bow or pivot outwardly to enable a change from projected area 239 (FIG. 19A) to increased projected area 239', as shown in FIG. 19B. As shown in FIG. 19A, outward movement of the membrane/central portion can be facilitated by scoring or cutting a small notch 249 in the wall of the membrane or central portion. This embodiment provides the advantages of a gusset portion. However, if a seal cannot be formed, the straps can be tightened so that the membrane 242 rests against the rim 240.

Figure 20A:
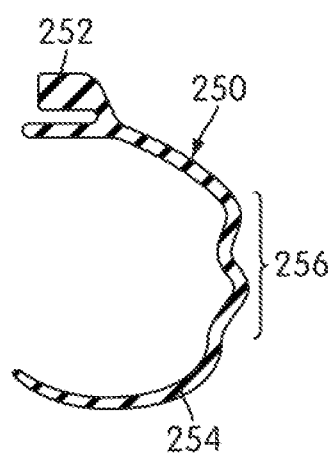
FIGS. 20A and 20B are a partial schematic views of still a further embodiment of the present invention.
Figure 20B:
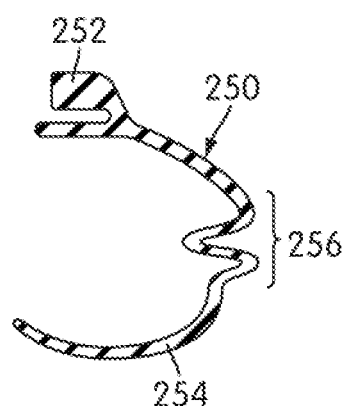

FIG. 20A is a partial schematic view of a cushion 250 according to yet another embodiment of the invention. Cushion 250 includes a non-face contacting portion 252, a face contacting portion 254 and a central portion 256 between the portions 252 and 254. Central portion includes thin walled sections that can kink, like a drinking straw, when the air delivery pressure changes. The kinking sections may be formed of a relatively rigid or semi-rigid plastic that is formed to allow it to flex, e.g., via a thin-walled section. For example, the plastic is like that of a drinking straw, which is generally rigid but can deform or flex as desired compared to the cushions that are made of silicone. In this embodiment, the projected area may not necessarily change, although provision could be made to do so. However, thin wall sections, e.g., about 0.2-1.0 mm, in central portion 256 have a spring effect which helps maintain the seal in place and a sufficient sealing force, especially during low pressure periods or during changes of gas delivery pressure. FIG. 20B shows cushion in a crushed state, in which central portion 256 has been plastically deformed to assume this configuration. The cushion maintains this shape, even without force, because it is plastically (v. elastically) deformed. In this position, central portion offers little or no spring effect.

Figure 21:
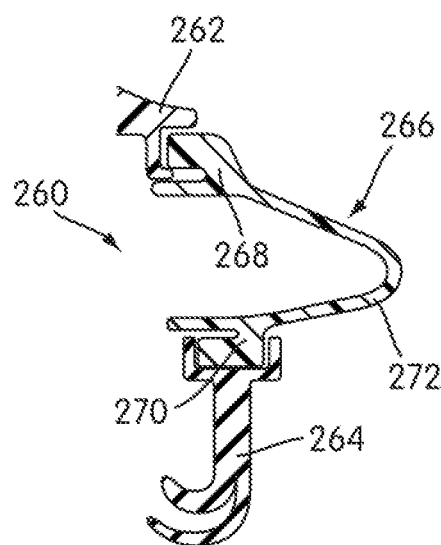
FIG. 21 is a partial schematic view illustrating still another embodiment of the present invention.

FIG. 21 is a partial schematic view of a mask assembly 260 according to another embodiment of the present invention. Assembly 260 includes a frame 262 and a cushion 264, e.g., a ResMed Mirage® cushion, both of which are commercially available. Assembly 260 includes a segmented design having an intermediate adapter portion 266 with a first end 268 that interfaces with the frame 262 and a second end 270 that interfaces with the cushion 264. Intermediate adapter portion 266 can be made of a relatively rigid or semi-rigid material, such as polypropylene formed in a thin wall to allow for flexing, and it may include a gusset portion 272. This allows for customization of the gusset portion to suit the flexibility or force range that is required. Alternatively, intermediate adapter portion 266 may include any of the alternatives described herein for providing more flexibility of the mask or for allowing a change in the applied sealing force with a change in pressure, e.g., via the use of a variable projected area and/or a variable spring force provided by a spring member or other resilient force. In this way, any mask can be retrofit to include an intermediate adapter member 266 according to this embodiment. Moreover, various ones of the embodiments described herein can be provided on an intermediate adapter portion so that the existing mask components need not be modified. Frame 262 may be integrally formed with gusset portion 272, with cushion 264 detachably provided thereto.

Figure 22:
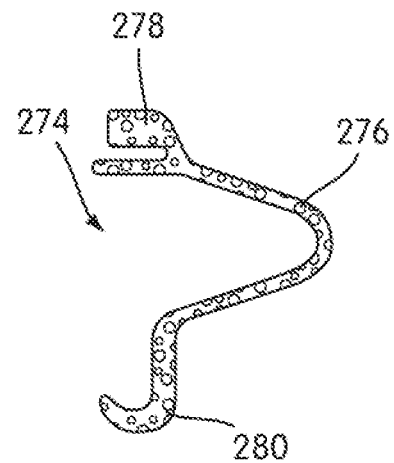
FIG. 22 is a partial schematic view of a further embodiment according to the present invention.
Figure 23:
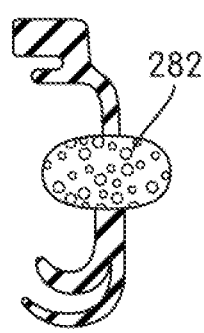
FIG. 23 is a partial schematic view according to another embodiment of the present invention.

FIG. 22 illustrates a partial view of a cushion 274 having a gusset portion 276 positioned between non-face contacting and face contacting portions 278, 280 of the cushion. Cushion 274 is substantially entirely gel-filled. Gel may include a soft flexible liquid, semi-liquid and/or visco-elastic polymer. Such gel material may be disposed and displaced within a skinned body. The skin may be stiff (non-stretchable), or it may be elastic or subject to elongation. FIG. 23 illustrates an alternative in which only a portion 282 is filled with gel. In FIG. 23, the gel portion 282 acts as a spring to provide the advantages of adding a spring previously discussed.

Figure 24:
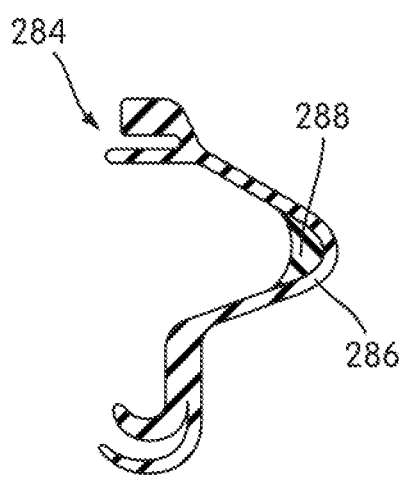
FIG. 24 is a partial schematic view according to another embodiment of the present invention.

FIG. 24 is a partial schematic view of a cushion 284 having a gusset portion 286. The contact force applied to the patient's face can be tailored by providing one or more reinforcement structures. The size, shape and geometry of these reinforcement structures can be arranged to vary stiffness in different sections of the gusset portion 286. For example, less stiff sections at nasal bridge region, stiffer sections at cheek region, to provide the required comfort and seal level. In this example, an inside portion of the gusset portion 286 includes a reinforcement member 288, e.g., an elastic flap or a gel filled pocket. Gel may act as a shock absorber and/or provide additional cushioning if and when the cushion bottoms out. An alternative to gel is gel foam, e.g., gel with bubbles or other filler with various compressible qualities. The added resiliency of member 288 has the advantage of preventing overstretching or undesirable deformation of the gusset portion 286 at high pressure or relative movement between frame and cushion, e.g., by bumping at night.

Member 288 should have a spring stiffness similar to that of the gusset under pressure and thus will provide additional force as the gusset closes. As previously discussed (for cuffs and springs) this force is not pressure related. Thus it increases the force at low pressure allowing the performance of the mask to fit within the zone Z, see FIG. 5.

Figure 24A:
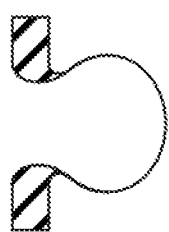
FIGS. 24A-24U are partial schematic views according to further cushion embodiments of the present invention.

FIGS. 24A-24U illustrate further embodiments according to the present invention. FIG. 24U schematically illustrates a partial section of a mask assembly 800 having a cushion including a face contacting/interacting portion 802 that may include a membrane 804 with an optional underlying rim 806. Cushion includes a non-face contacting portion 808 that is supported by a frame 810. A central portion 812, in the form of a black box, is provided between portions 806 and 808.

FIGS. 24A-24T illustrate various central portions that can be used for control portion 812 in FIG. 24U. In the case of FIGS. 24N and 24R, face-contacting interacting portion 808 and/or frame 810 (FIG. 24U) would be adjusted, e.g., widened, to accommodate for illustrated offset. Various features of FIGS. 24A-24T are tabulated below in Table 1.

TABLE 1

Figure 24B:
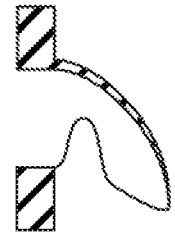
Figure 24C:
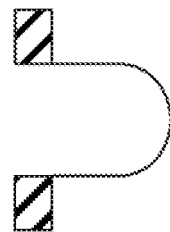
Figure 24D:
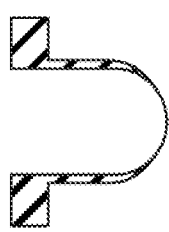
Figure 24E:
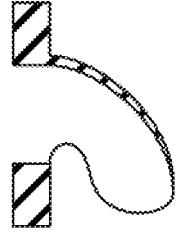
Figure 24F:
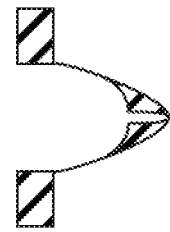
Figure 24G:
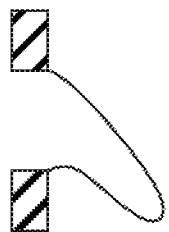
Figure 24H:
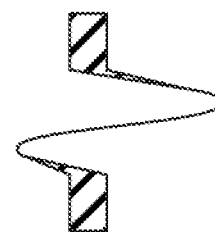
Figure 24I:
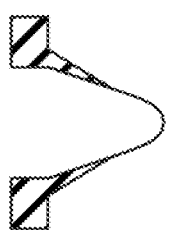
Figure 24J:
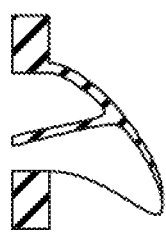
Figure 25:
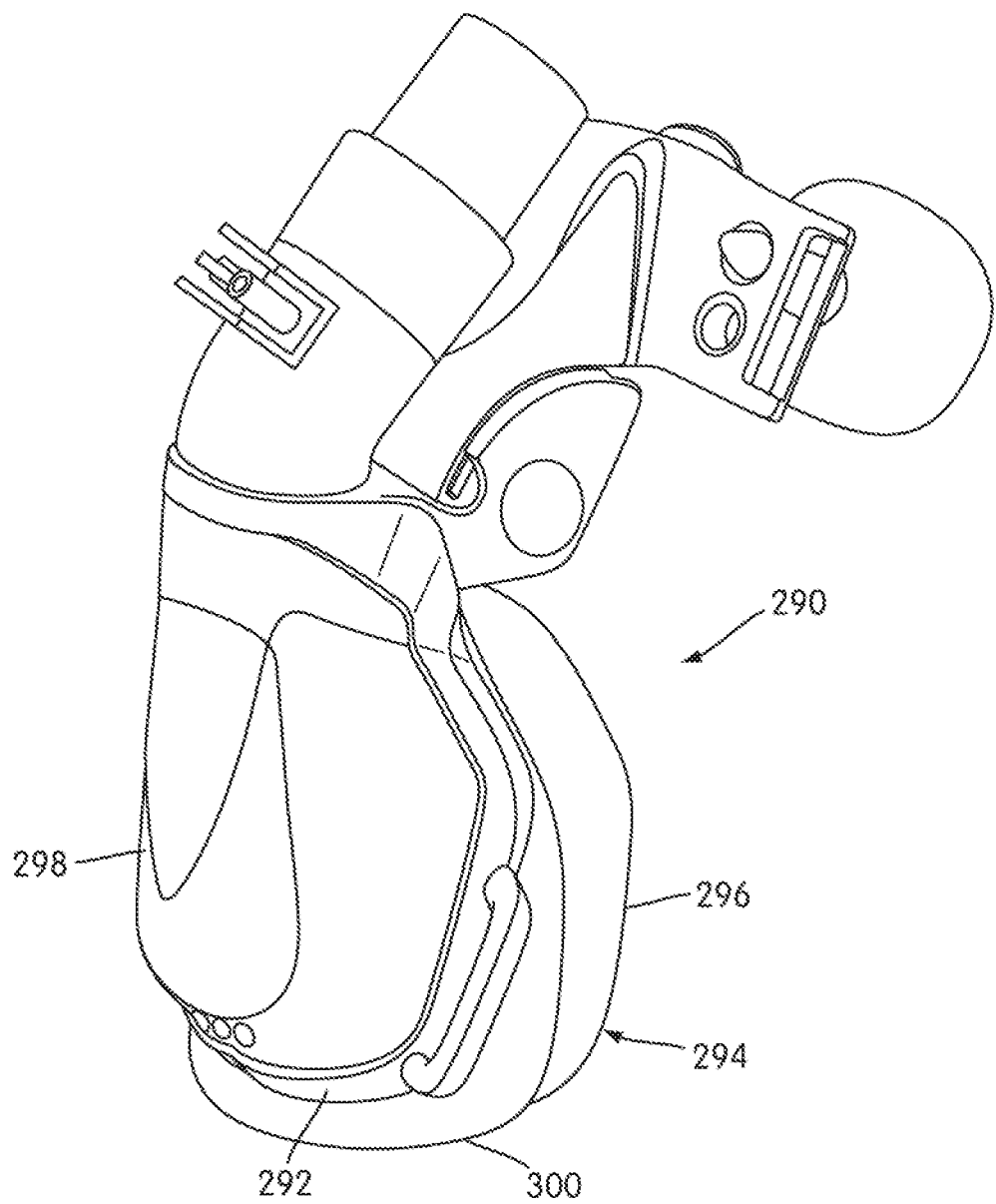
FIG. 25-27C illustrate a further embodiment according to the present invention.

| Drawings | Comment |
|---|---|
| FIG. 24A | Circular cross-section. Provides more travel for the same outer area. The circular shape will deform less when pressurized, therefore outer area remains constant. |
| FIG. 24B | Underside notch has dual purpose. On extension provides more travel (longer path length), on compression acts as spring. Upperside is tapered wall section. |
| FIG. 24C | Circular cross-section at end of straight gusset. Provides more travel for the same outer area. The circular shape will deform less when pressurized, therefore outer area remains constant. |
| FIG. 24D | Like FIG. 24C, but with tapered or thickened wall section. When pressurized, the thickened wall section tends to keep the form. |
| FIG. 24E | Underside notch provides more travel on extension. This is assisted by the thickened upper wall which tends to keep the form. This also allows for a constant outer area ($A_g$). |
| FIG. 24F | In compression, a spring constant is added. In extension, no spring effect (one-sided spring). This has the advantage of having a spring at low pressures but not necessarily at high pressures. |
| FIG. 24G | Angled gusset provides more travel for the same outer area. |
| FIG. 24H | Internal gusset provides more travel for the same outer area. |
| FIG. 24I | Thickened section deforms only under higher pressures. At lower pressures, thickened section will touch when gusset is compressed and act as spring. This has the advantage of having a spring at low pressures but not necessarily at high pressures. |
| FIG. 24J | Thickened section deforms only under higher pressures. This moves the spring tab away from the lower section (i.e., no spring). At lower pressures, spring tab will touch when gusset is compressed and act at spring. This has the advantage of having a spring at low pressures but not necessarily at high pressures. |
| FIG. 24K | Thickened section will not deform under pressure, maximizes outer area with respect to FIG. 24G. Angled gusset also provides for more travel for the same area. |
| FIG. 24L | Double gusset provides more travel for the same outer area. |
| FIG. 24M | Spring element added. |
| FIG. 24N | Attachment point moved outwards. Outer area maintained fixed. Underside notch provides more travel (longer path length). |
| FIG. 24O | In compression, a spring constant is added. In extension, no spring effect (one-sided spring). Note: Similar to but more spring and less expansion of the gusset at high pressures. |

TABLE 1-continued

| Drawings | Comment |
|---|---|
| FIG. 24P | Angled gusset provides more travel for the same outer area. |
| FIG. 24Q | In compression, a spring constant is added. In extension, no spring effect (one-sided spring). Similar to FIG. 24F, this has the advantage of having a spring at low pressures but not necessarily at high pressures. |
| FIG. 24R | Attachment point moved outwards. Outer area maintained fixed. Shape of gusset provides more travel (longer path length). |
| FIG. 24S | Spring effect in extension. No spring effect in compression. Thick walls provide more constant outer area under pressure. |
| FIG. 24T | Double internal gusset allows for outer area to be varied from large to none while still allowing significant travel. |

Notes:
1 Extension is taken to be movement of frame away from lower cushion
2 Compression is taken to be movement of frame towards lower cushion
3 Travel is taken to be amount of extension plus compression
4 Outer area is taken to be the outer area of the gusset FIGS. 25-27C are illustrations of a mask assembly 290 according to still another embodiment of the present invention. Mask assembly 290 includes a frame 292 which is provided with a cushion 294. Cushion 294 and breathing chamber forming portion 298 are formed in one piece, although they could be formed in separate pieces and/or portion 298 could be formed as part of frame 292. Cushion 294 has a resilient face contacting portion 296. Cushion is provided to frame 292 as shown and described in U.S. Design Pat. No. D484,237, U.S. non-Provisional patent application Ser. No. 10/221,572 and U.S. non-provisional patent application Ser. No. 10/221,574 each incorporated herein by reference in its entirety.

Figure 26:
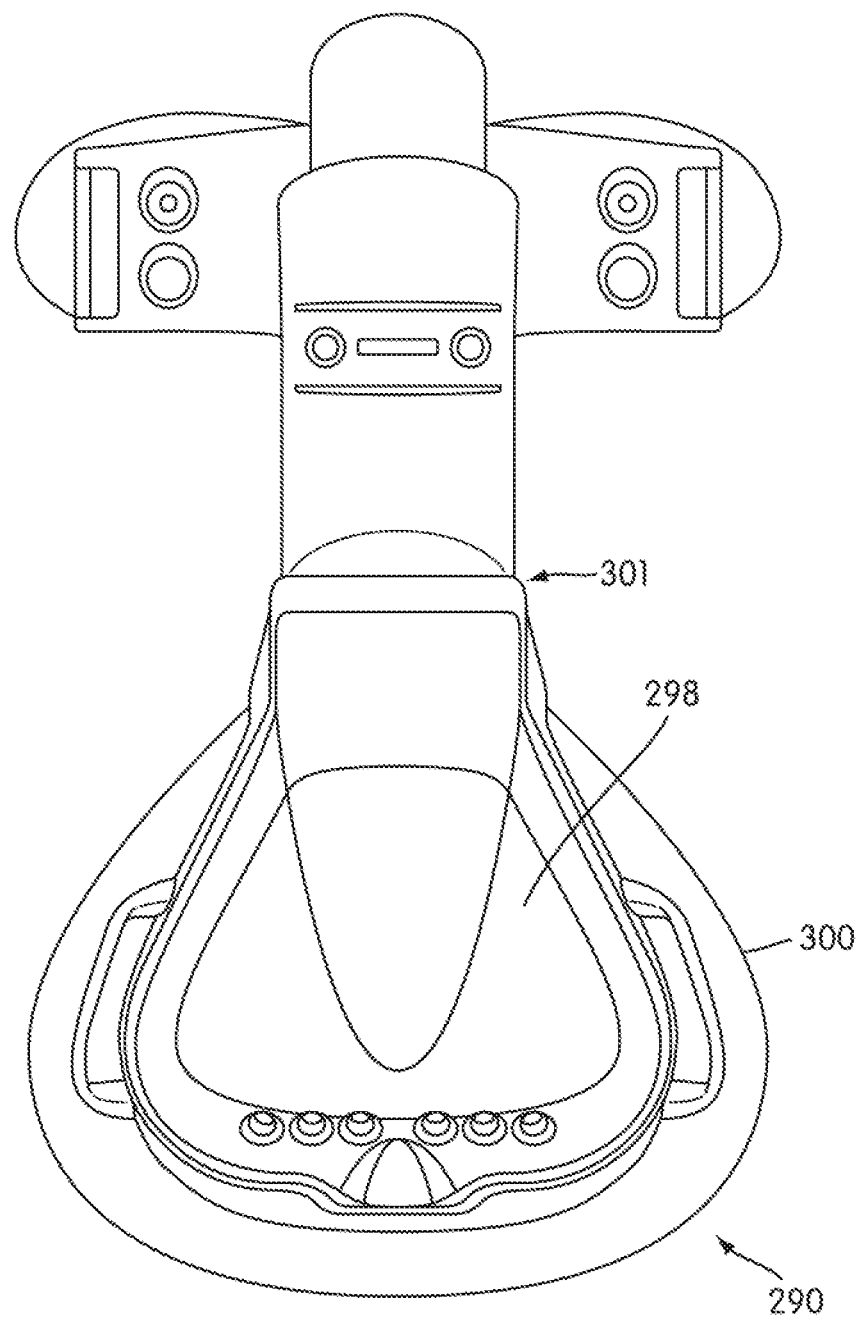
Figure 27A:
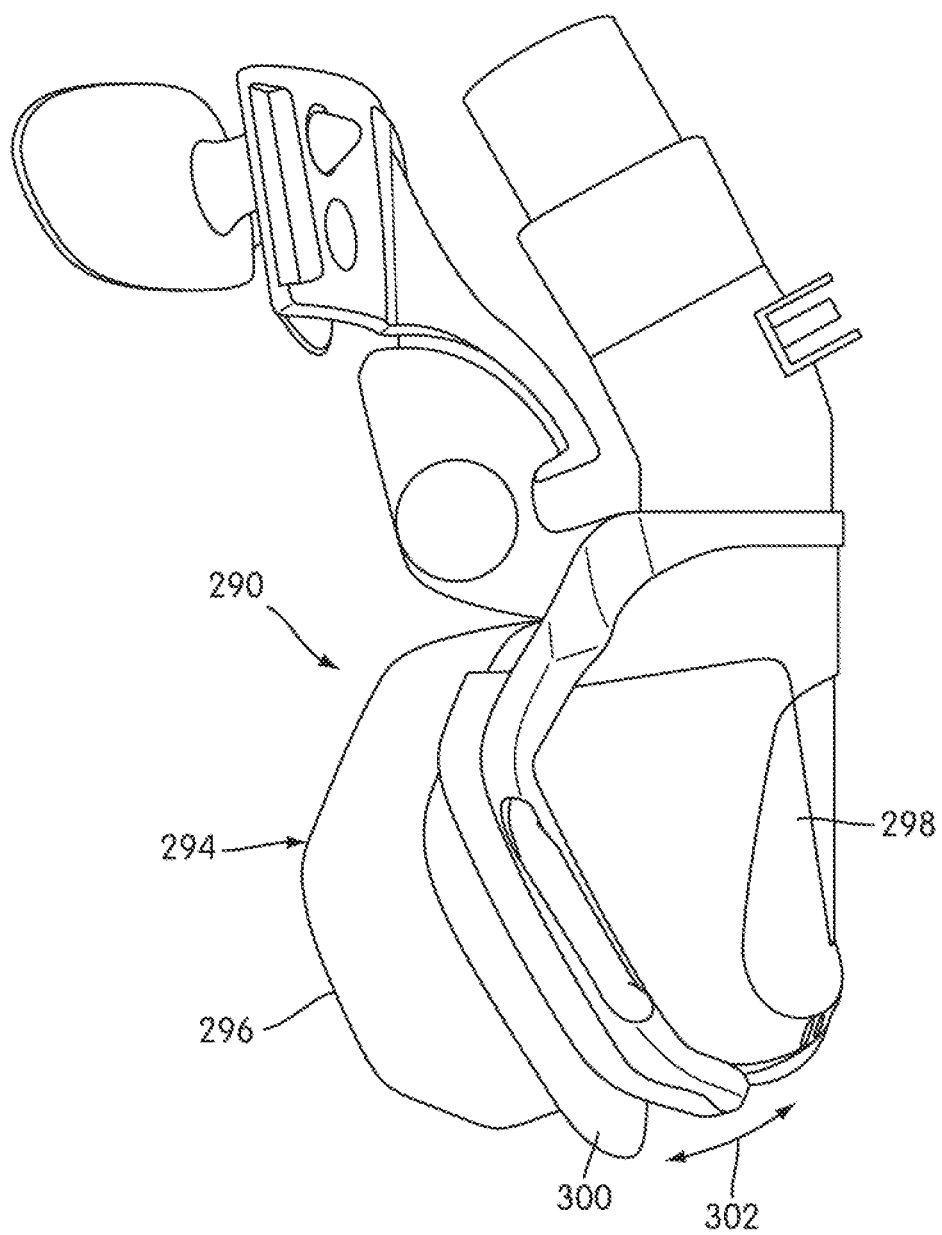
FIG. 27D illustrates a perspective view of a cushion arrangement according to another embodiment of the present invention.
FIG. 27E is a side view illustrating a cushion arrangement according to yet another embodiment of the present invention.
Figure 27B:
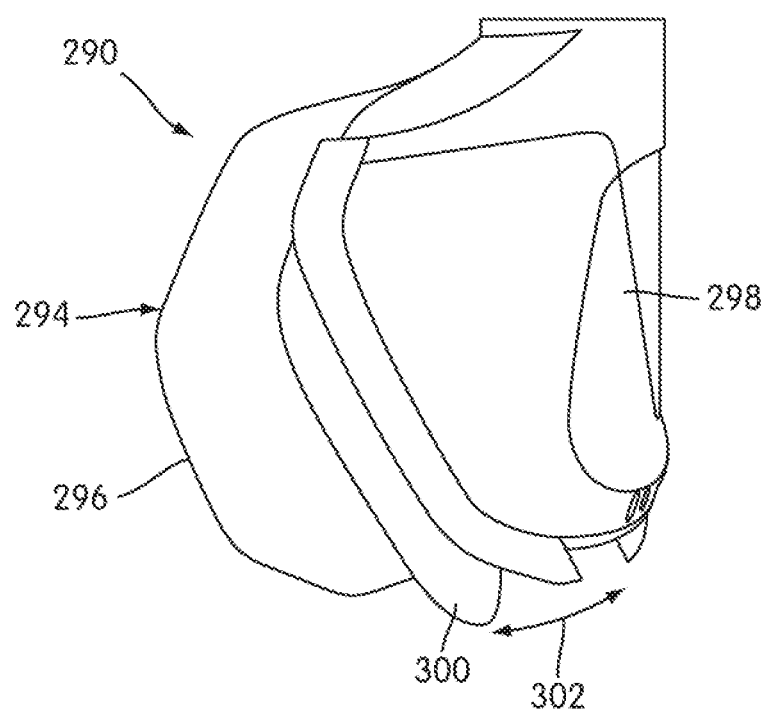
Figure 27C:
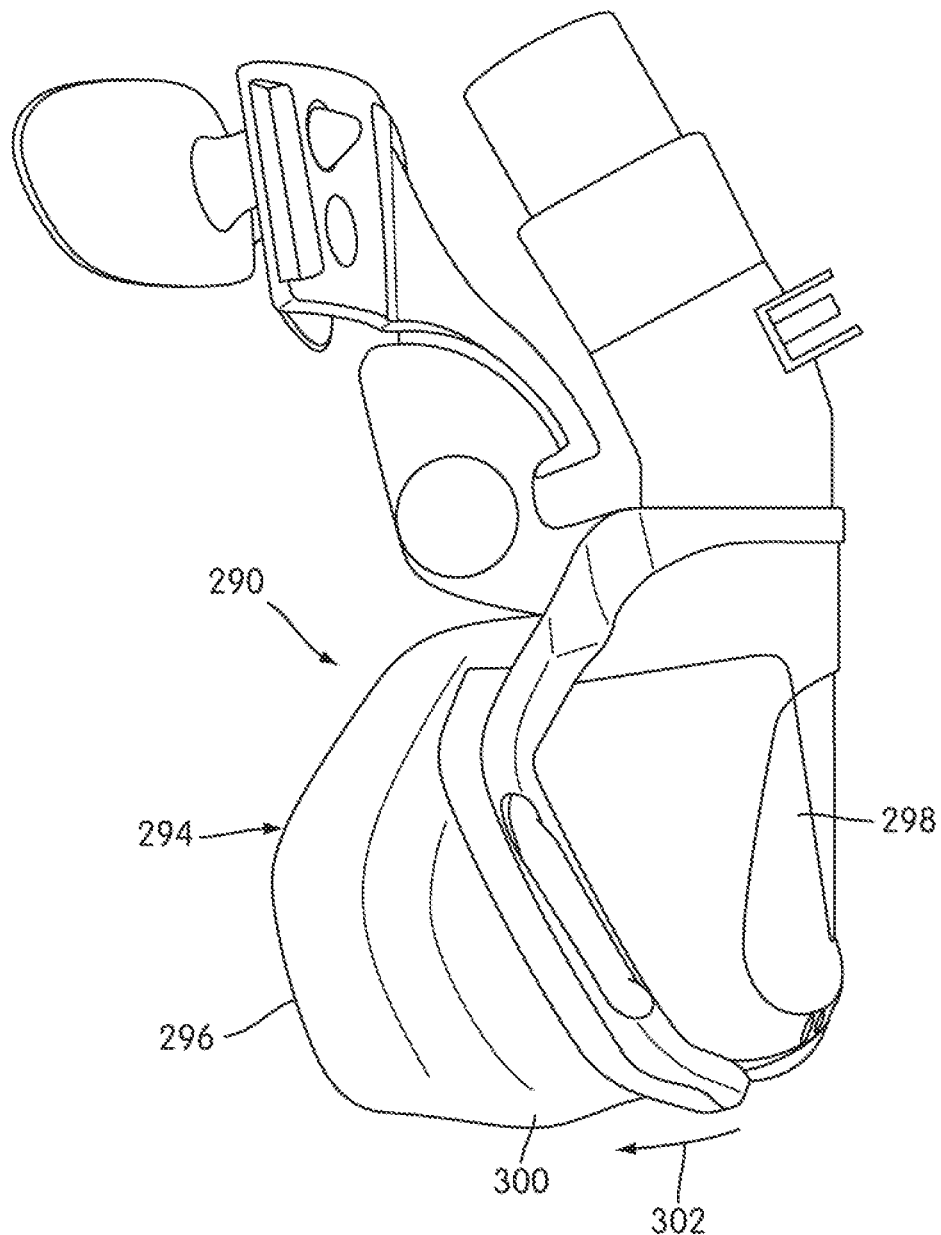

Cushion 294 is adapted to include a concertina-type gusset portion 300, including one or more folds. As seen in FIG. 26, the gusset portion 300 tapers as it approaches the apex 301 of the mask above the nose of the patient. As shown in FIG. 27A, it can be seen that gusset portion 300 also tapers in width as it approaches the apex. As such, the gusset portion 300 is at a minimum or nil at the apex, meaning that very little if any gusset type compensation is offered at the apex. The gusset portion 300 essentially allows the cushion 294 to move in an arcuate manner generally indicated by arrow 302 in FIG. 27A. This may be described as a "hinged-concertina" form of a gusset portion. FIG. 27B shows the cushion without the frame. FIG. 27C shows the gusset portion in a stretched or expanded position, as indicated by the area 302.

Figure 27D:
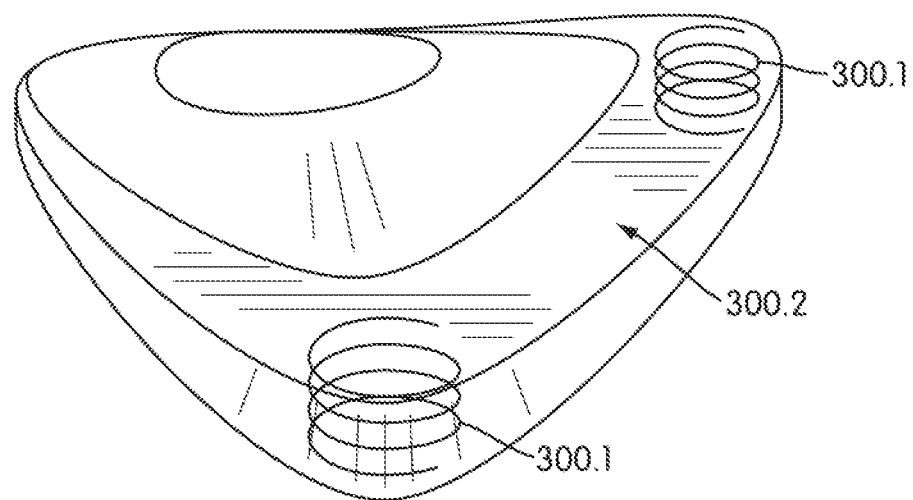

As a further design, as shown in FIG. 27D, the flexibility could be achieved through the addition of one or more small compression springs 300.1 on the bottom corners of the mask and the cushion may have a thin side wall that could collapse in any direction. A hinge point may be provided at the apex. A portion 300.2 could be formed with a rigid beam, as desired.

Figure 27E:
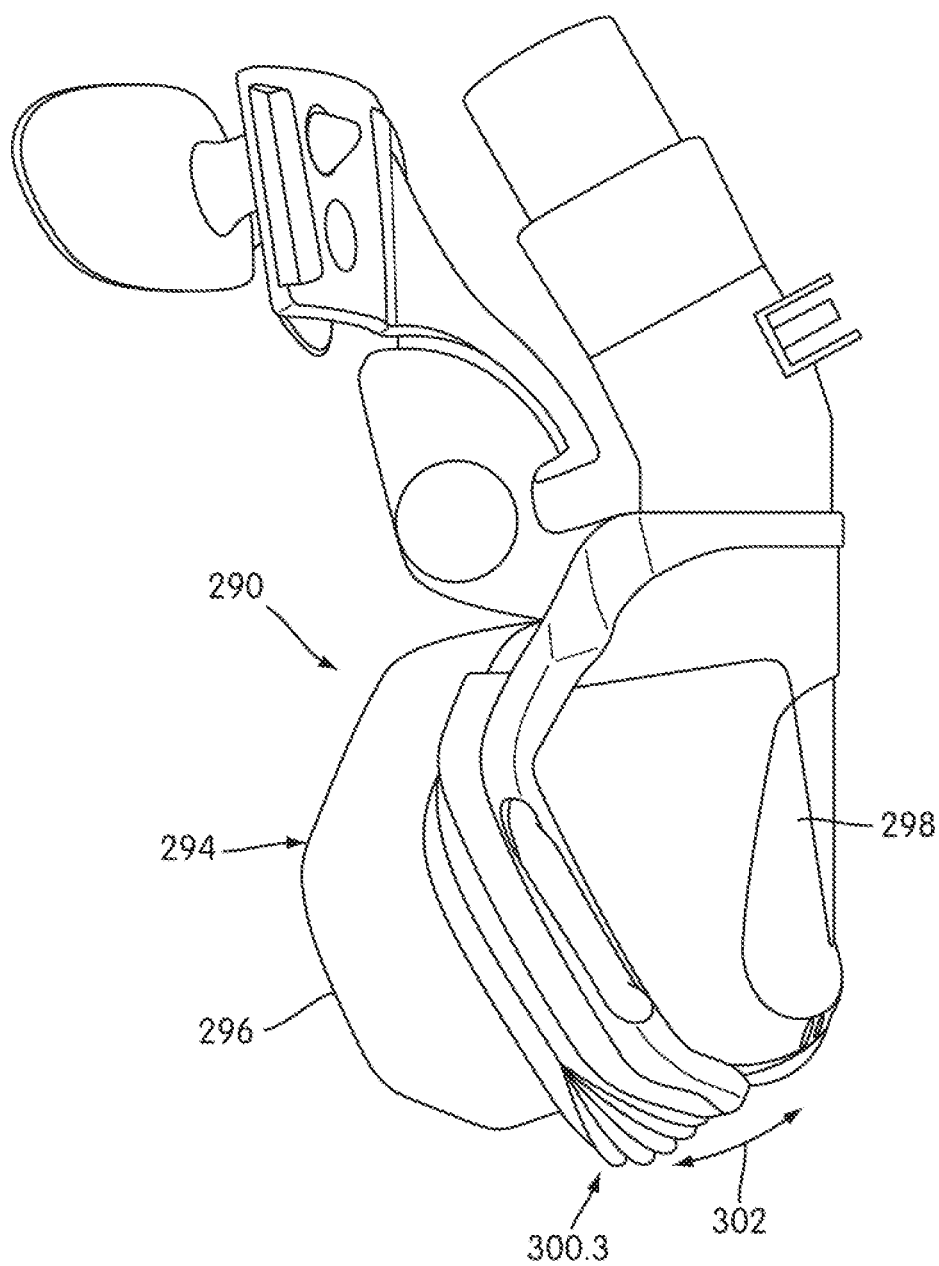

FIG. 27E shows a mask assembly 290 like that shown in FIG. 27A, but the bottom portion of the gusset is converted into one or more compression springs 300.3. Compression springs 300.3 may take the form of a single spring that is generally centered over the lip portion, or it may include a spring at each corner of the bottom portion of the cushion.

Figure 28:
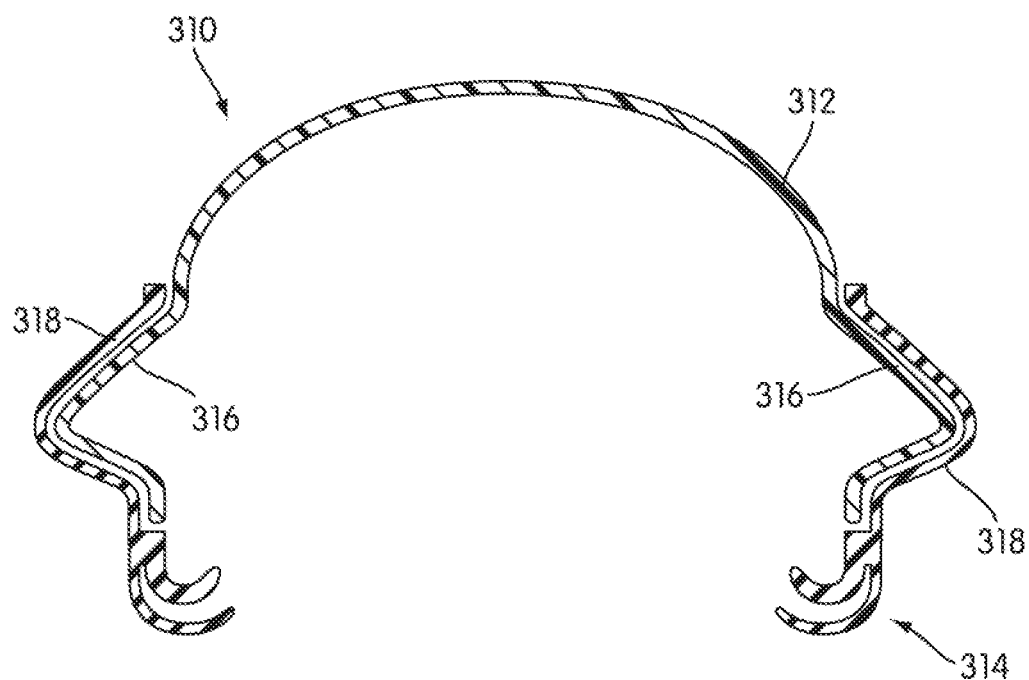
FIG. 28 is a schematic view illustrating another embodiment according to the present invention.

FIG. 28 is a schematic view of a mask assembly 310 having a frame 312 and a cushion 314. Frame 312 includes a bulbous flange portion 316 which simulates the shape of a gusset portion. Bulbous portion 316 may be solid, or it may simply be a skeleton with ribs which may help the bulbous flange portion 316 to act as a spring. Cushion 314 may include a thin membranous section 318 that is stretched to seal over bulbous portion 316. Section 318 may be made of silicone, gel and/or foam.

In use, the silicone may extend away from the bulbous flange portion due to either the weight of the cushion or the force of the pressurized gas acting on it. However, if the headgear straps are tightened and the gusset portion is compressed, the silicone will bottom out upon the spring which will provide an additional sealing force.

In another aspect, the gusset portion or the simulated versions or adaptations of the gusset portion have applications particularly suited to barriatrics. In particular, due to rapid weight loss following a barriatric operation, the flexible nature of the gusset helps to accommodate changes in the shape of the face, thereby maintaining a seal with the same cushion and forehead strap position throughout the treatment period. Standard cushions including silicone, gel and foam-based products may not have sufficient flexibility to achieve a seal though the treatment period, in particular require modifications to the strap lengths, and possibly changes in cushion sizing. With the cushions described herein, an automatic sealing system is provided, i.e., the cushion may move automatically to seal against the face. This automatic motion compensates for variations in pressure and variations in facial position.

An advantage of the systems described herein is that each can be customized through variation of the projected area of the gusset around the perimeter of the lower cushion to provide tailored forces at differing locations. One potential use of this technology relates to use for infant masks. For example, the mask can utilize gusset portions to provide force at set locations which are most comfortable for an infant. In another example, a system of different gussets for different nights or weeks could be implemented with each changing the pressure points and preventing continuous constant pressure from a mask deforming the face.

Figure 29:
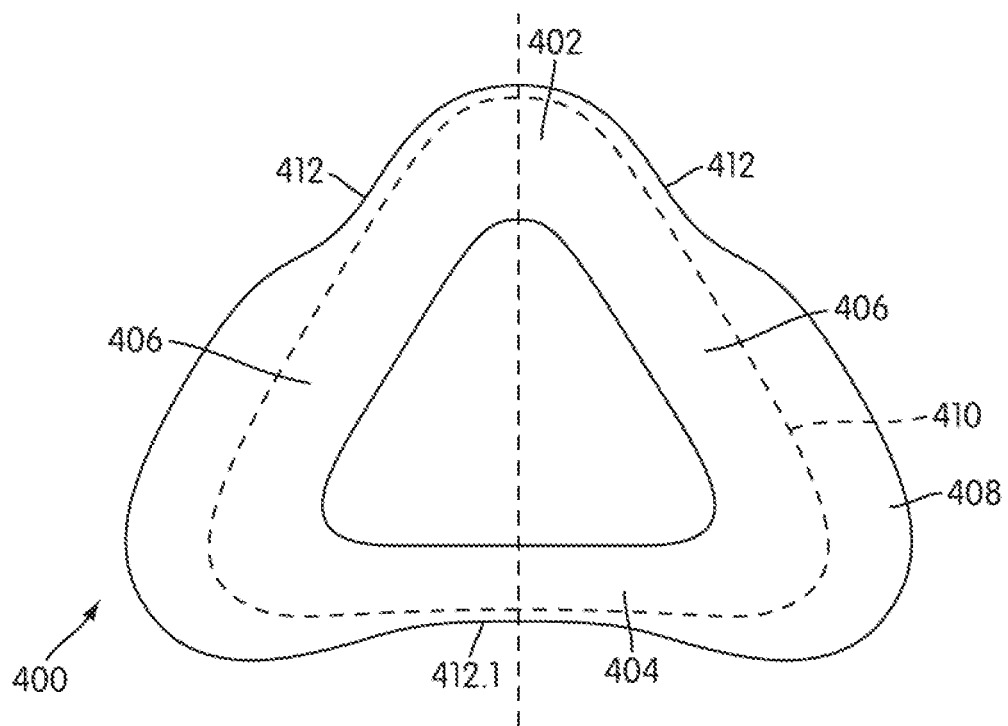
FIG. 29 is a schematic view of a cushion according to yet another embodiment of the invention.

FIG. 29 illustrates a schematic drawing of a cushion 400 according to still another embodiment of the present invention. Cushion 400 in this example, is a nasal cushion, although it could also be a full face (oro-nasal) cushion. Cushion 400 includes a nasal bridge region 402, an upper lip region 404 and cheek regions 406 therebetween. Cushion 400 includes a region 408, including a gusset and/or spring portion, as described above. Region 408 has variable dimensions along the perimeter of the cushion 400. For example, region 408 is defined between the perimeter edge 412 of the cushion 400 and a dotted line 410 shown in FIG. 29. As shown, region 408 is relatively small or nil in the nasal bridge and/or upper lip regions 402, 404, where relatively little force is required, which can help reduce the possibility of discomfort, while cheek regions 406 have a relatively wider profile for region 408. Further, region 408 has cut away portions 412 to allow for improved patient vision. Cut-out 412.1 is provided to reduce/eliminate contact with lip of patient. FIGS. 30-33 illustrate cushion 400 from various perspectives and views. Non-face contacting portion 414 and face contacting portion 416, including membrane 418, are shown, e.g., in FIG. 30.

Figure 33:
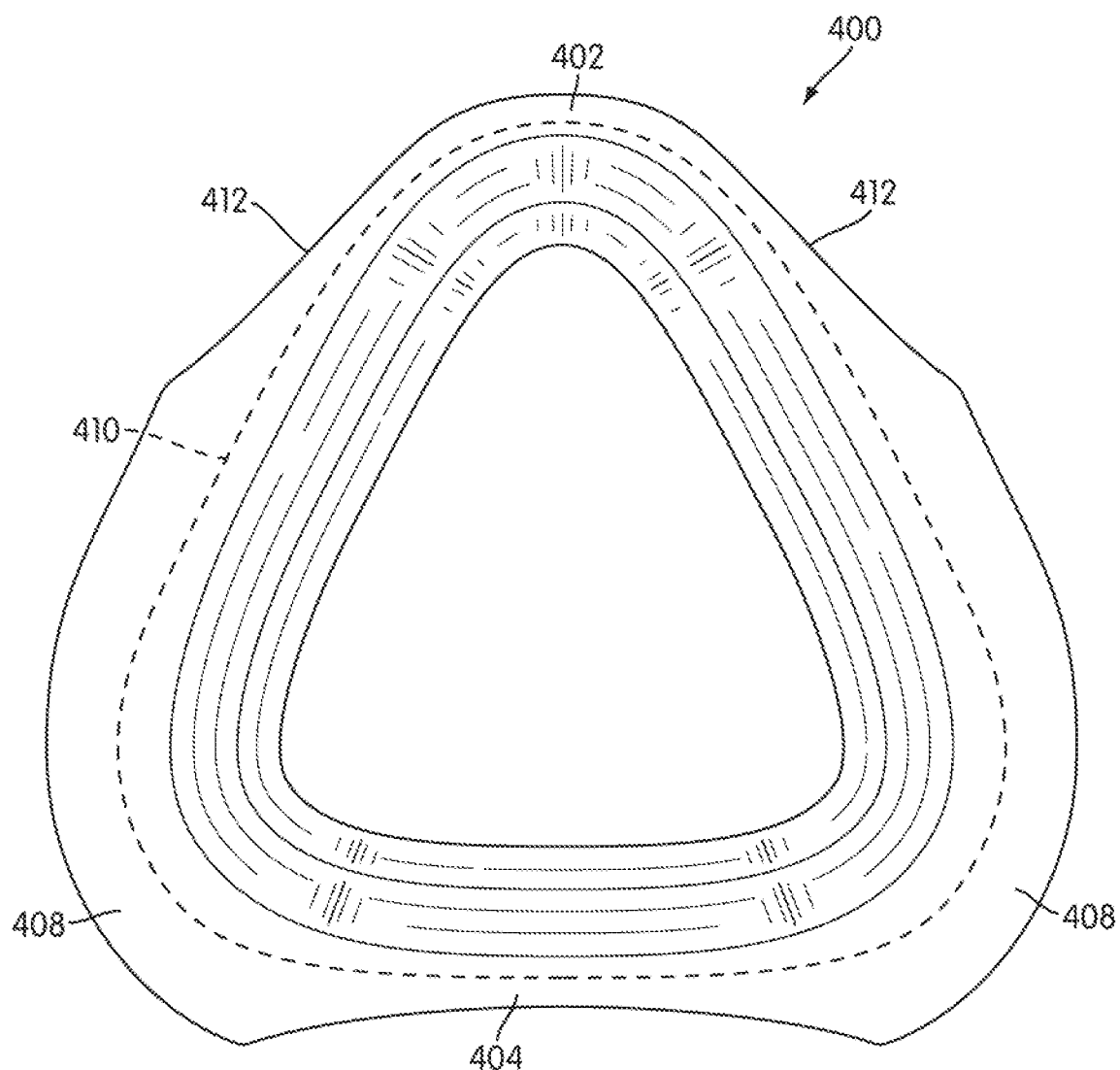
FIG. 33 is a front view thereof.
Figure 33A:
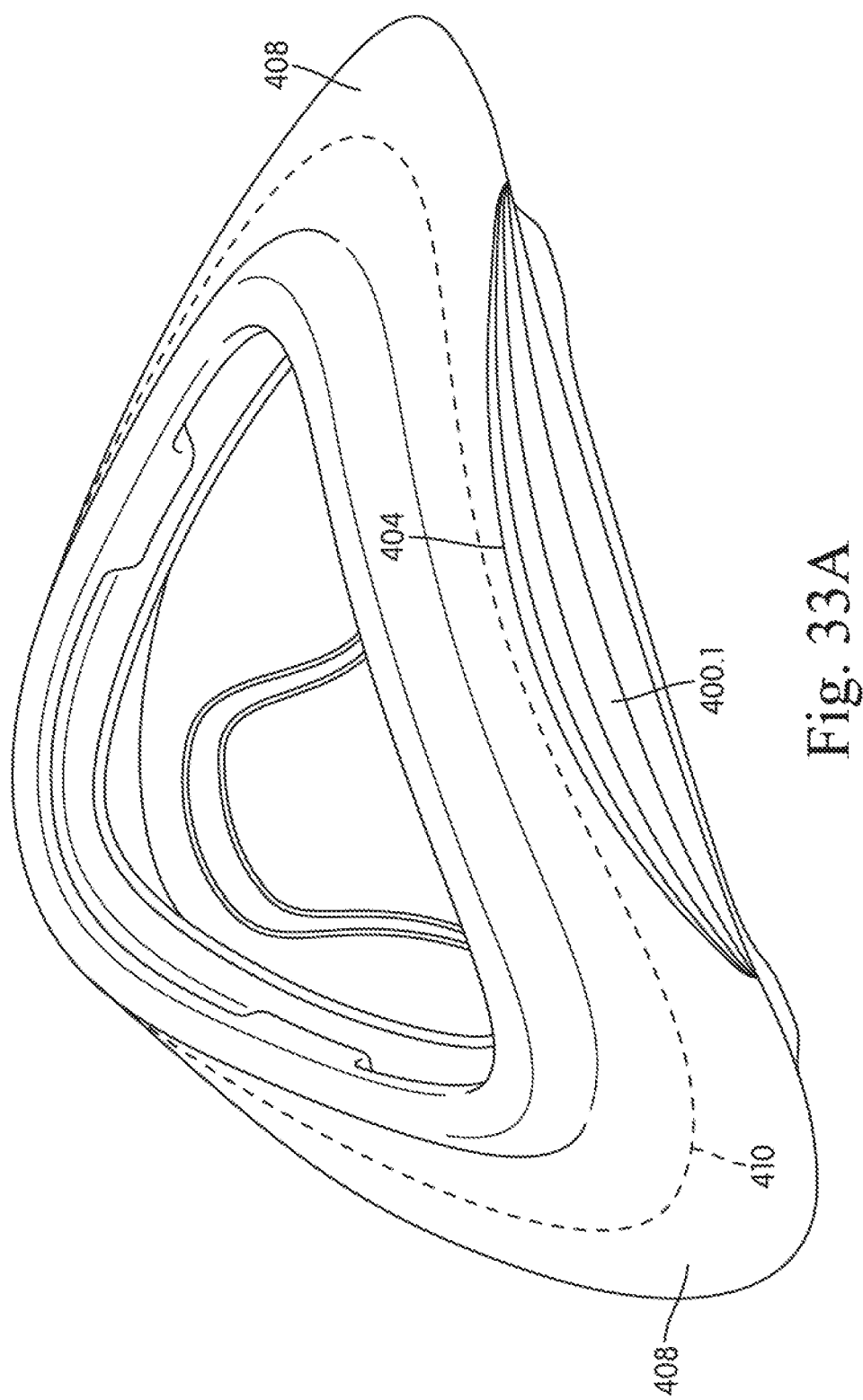
FIG. 33A is a perspective view of a cushion according to still another embodiment of the present invention.

The force is primarily applied to the cheek region and in particular the creases in the cheek. These areas are the least sensitive to pressure and are thus preferable for reasons of comfort. In addition the force is focused on areas where there may be leak (like creases in the cheek) rather than areas where typically little leak occurs (eg: upper lip region). The areas where there is little gusset area such as the upper lip region may contain concertina type folds 400.1 (see FIG. 33A). These allow the flexibility and travel that the gusset provides without applying force due to pressure. As an alternative embodiment, these folds may incorporate some element of spring force through any of the methods previously discussed.

Figure 29A:
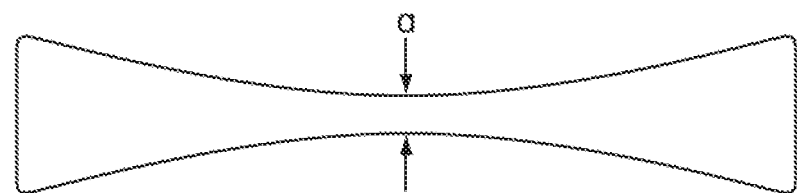
FIG. 29A is a schematic top view of the cushion in FIG. 29.
Figure 30:
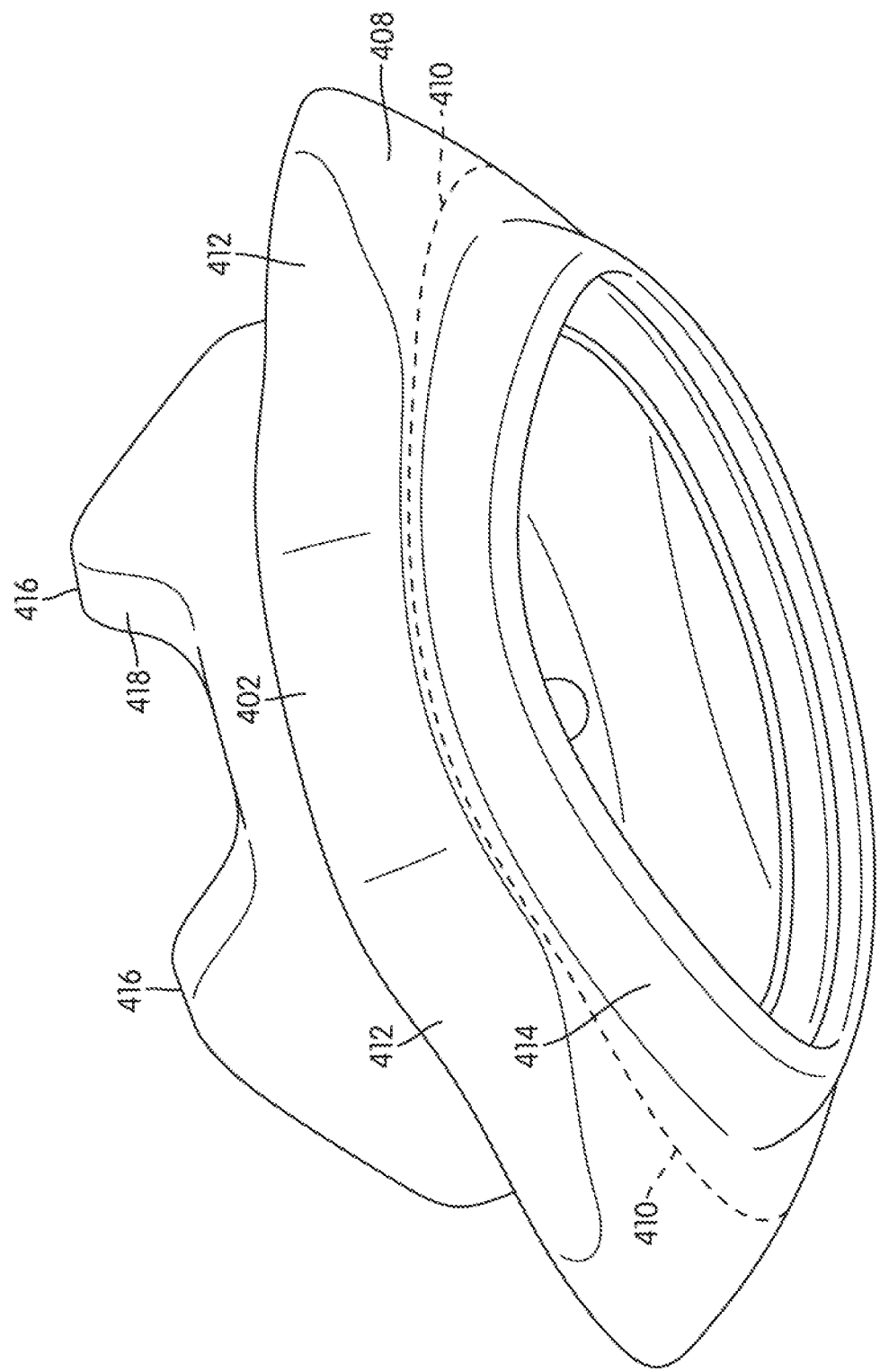
FIG. 30 is a top perspective view of a cushion with features described in relation to FIG. 29.
Figure 31:
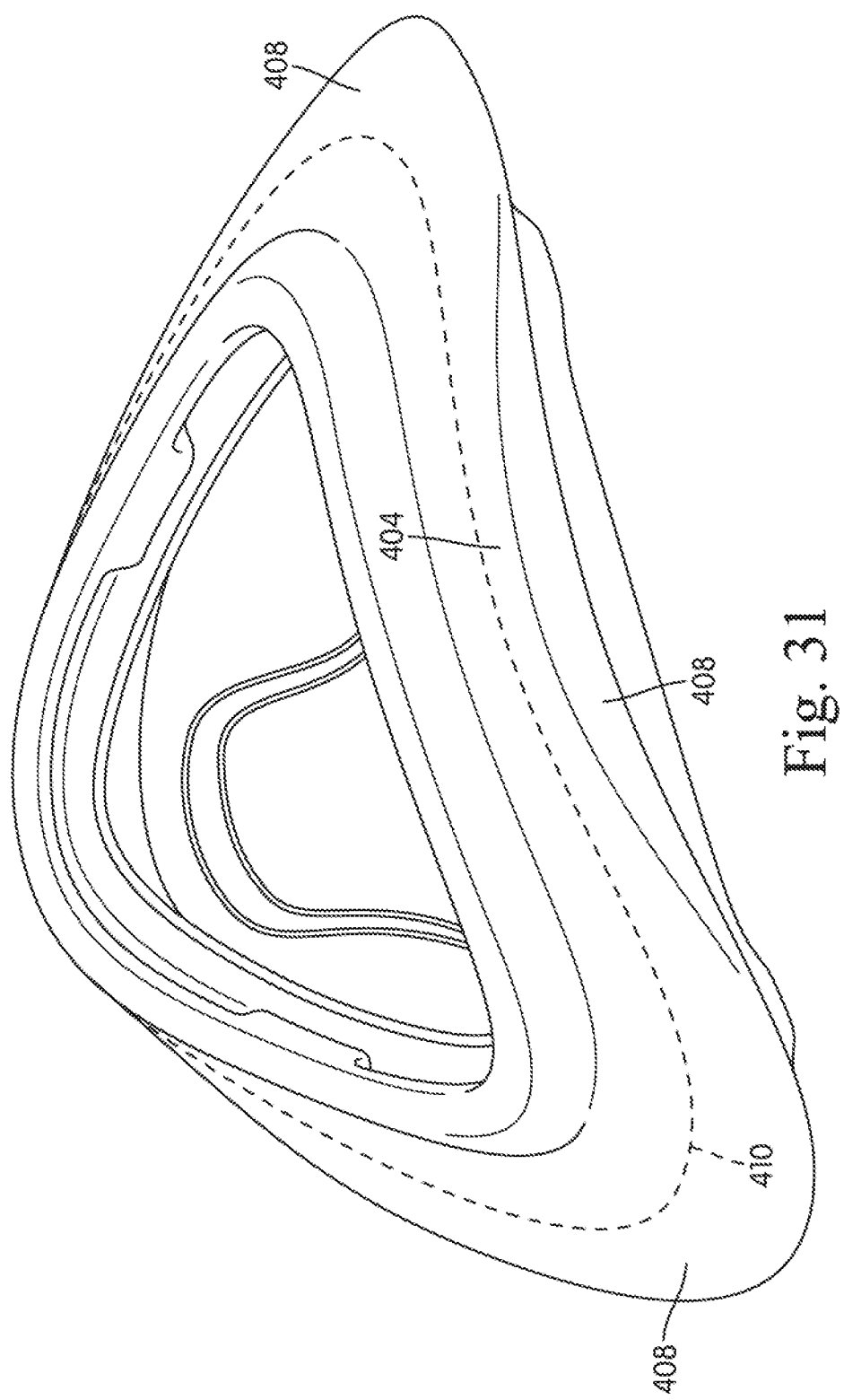
FIG. 31 is a bottom perspective view thereof.
Figure 32:
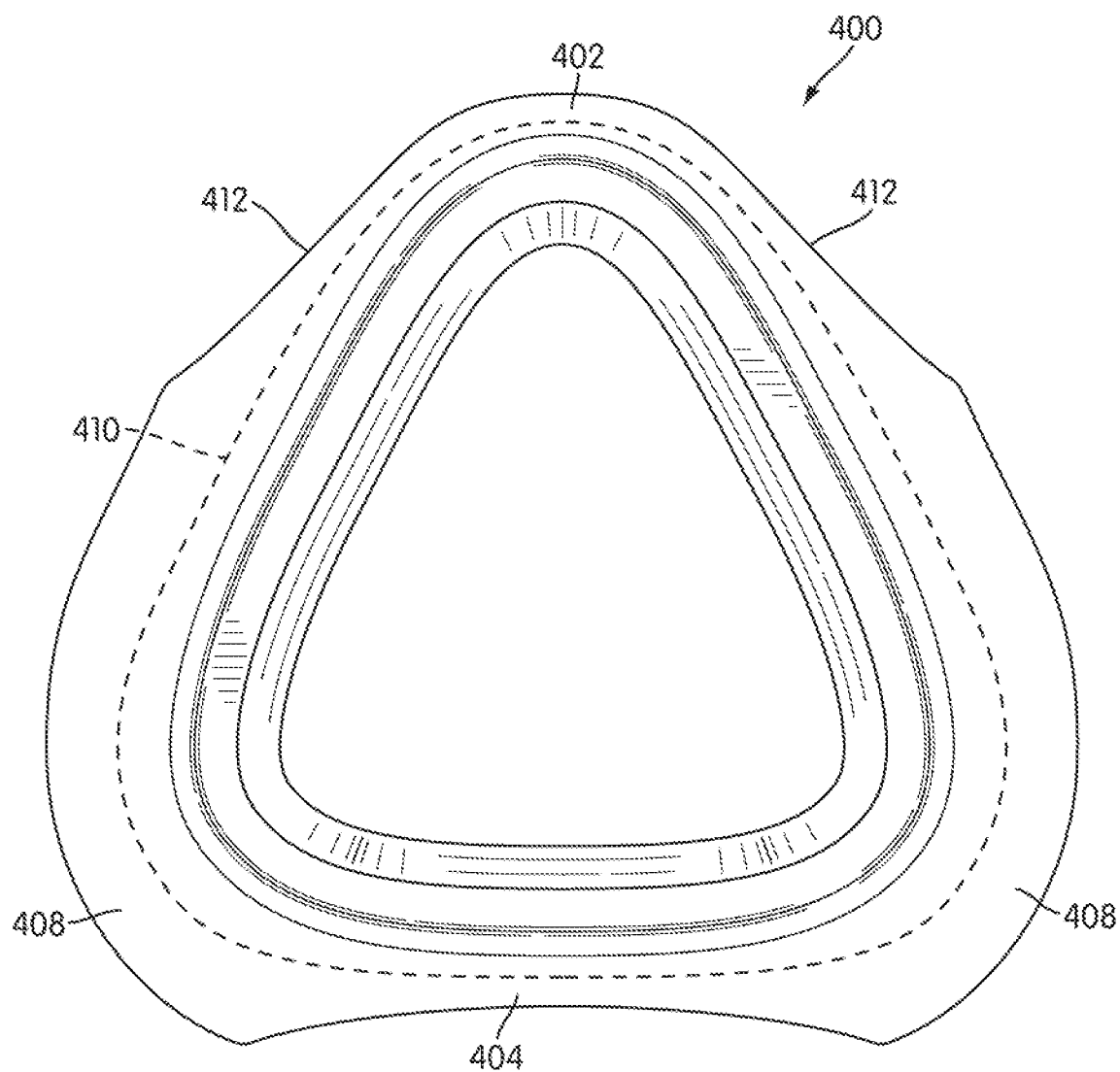
FIG. 32 is a rear view thereof.

Although gusset area is near zero in the region of the eyes and lips of the patient, the thin wall has a height (FIG. 29A) that allows the cushion to rotate sideways to maximize stability. The effect is similar to that described above in relation to FIG. 31 (described below), in which the vertical centerline acts as a hinge about which side portions (cheek regions) may pivot. Although displacement of cushion to frame is reduced, the cushion still decouples frame movement side-to-side.

Full Face Mask Embodiments

FIGS. 50-55 disclose two alternative embodiments of the present invention which are directed to full face masks.

Figure 50:
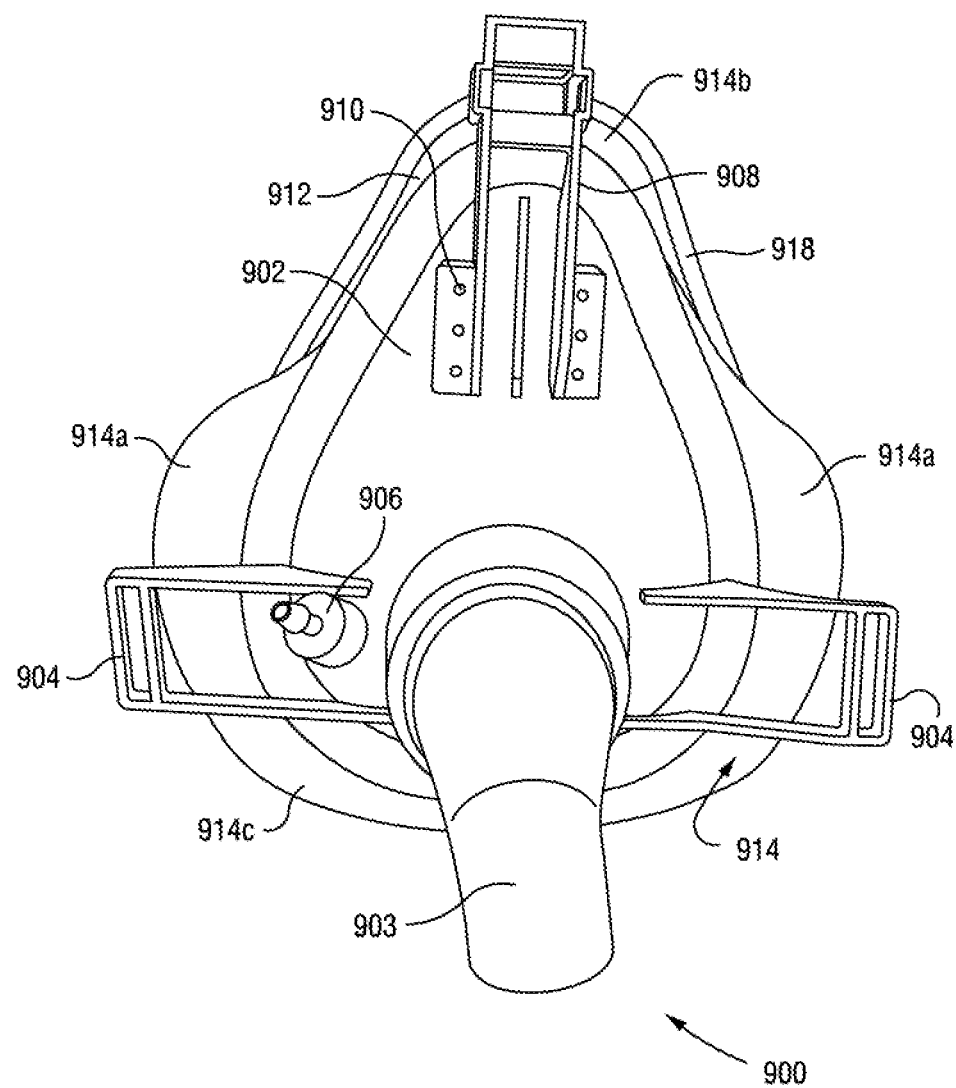
FIGS. 50-52 illustrate a full face mask assembly according to another embodiment of the present invention.
Figure 51:
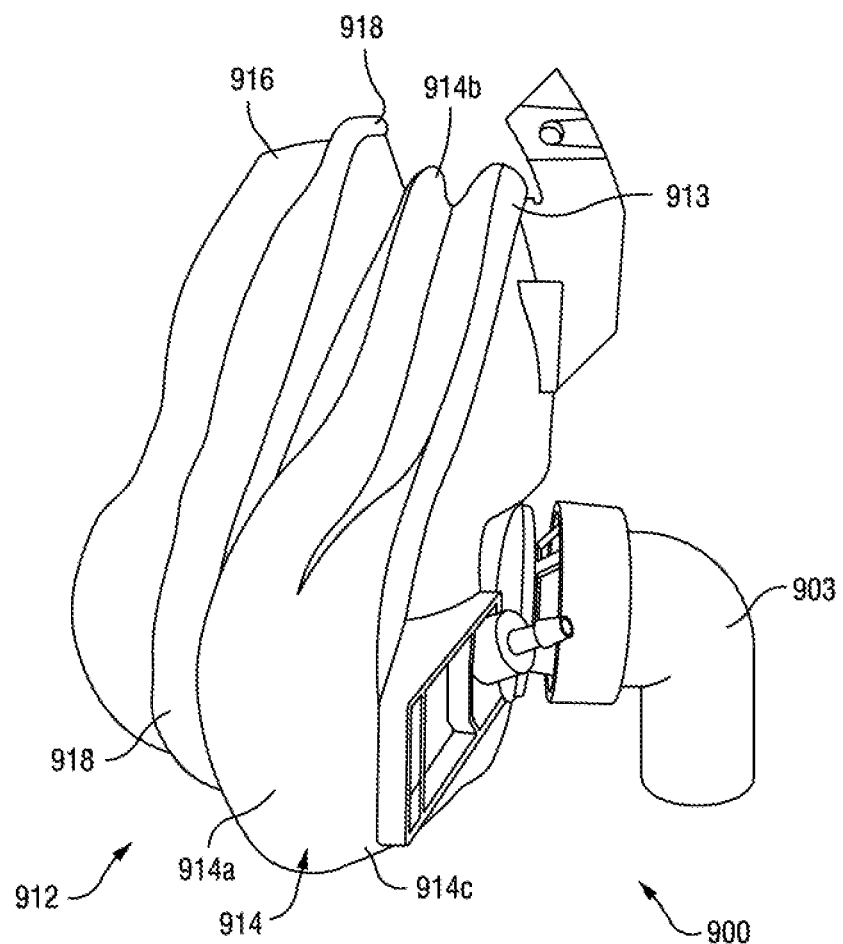
Figure 52:
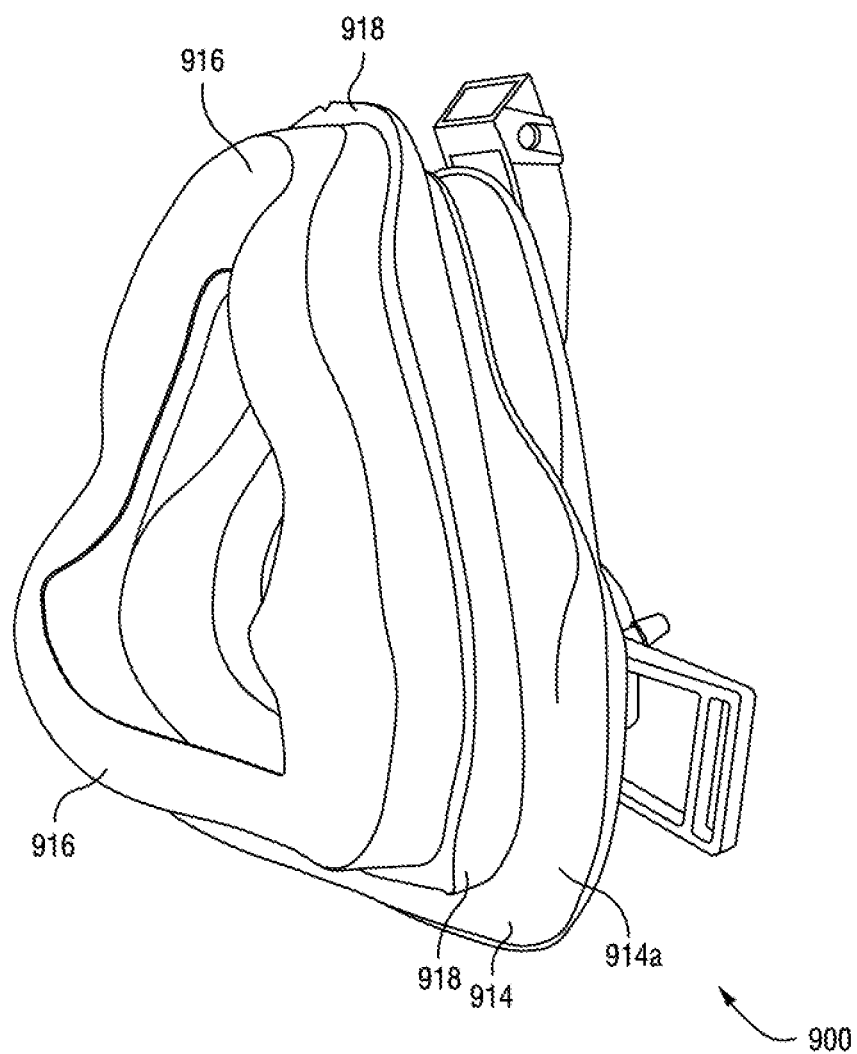

FIGS. 50-52 illustrate a mask assembly 900 including a shell 902 with integrally attached slots 904 for receiving straps of a headgear assembly, not shown. Shell 902 is provided with a source of pressurized air through central aperture, typically via an air supply conduit such as an elbow 903. Shell 902 also includes upstanding support structure 908 which may be provided for the support of the forehead pad assembly. Shell 902 may also be provided with one or more vents 910. In FIG. 50, a portion of a cushion 912 can be seen around the perimeter of shell 902. In particular, cushion 912 is provided with a gusset 914 having frontal and side profile views which are similar to that disclosed in FIGS. 29 and 30-33. For example, as shown in FIG. 50, gusset 914 includes cheek regions 914a, a nasal bridge region 914b, and a lower lip region 914c. As described above in relation to FIG. 29, for example, these portions of the gusset have various profiles in order to tailor the amount of force which is applied to the particular region of the patient's face, depending on the sensitivity of the patient's face as well as the required sealing forces thereof.

FIG. 51 is a side profile view of the mask assembly 900. Cushion includes a shell contacting portion 913 which may have a profile, for example, shown in FIG. 10. Gusset 914 is seen as having a relatively low profile in the nasal bridge region 914b. For example, the nasal bridge region 914b is provided generally adjacent the upper portion of the shell which is covered by the shell contacting portion 913 of cushion 912. A face contacting portion 916 may include a soft membrane as well as an underlying rim, as described in relation to FIG. 10.

Further, a ring shaped reinforcement 918 is provided between gusset 914 and face contacting portion 916. Further details of the reinforcement 918 are described in U.S. Provisional Application No. 60/643,121, filed Jan. 12, 2005, incorporated by reference in its entirety. The reinforcement 918 may be secured to the cushion 912 in any suitable manner. For example, the reinforcement 918 may be attached to an exterior surface of the cushion 912, e.g., by friction fit, adhesive, and/or mechanical fasteners. In an embodiment, the reinforcement 918 may be provided within a groove circumscribing a portion of cushion 912 which lies between gusset 914 and face contacting portion 916. The reinforcement 918 has a function of limiting distendability or expansion of the cushion 912 when subject to high pressures, for example. In one embodiment, the reinforcement 918 may be constructed of a substantially rigid material, e.g., plastic, composite. In another embodiment, the reinforcement 918 may take the form of an insert made of open or closed cell foam and function like insert 114.2 described above in FIGS. 9B and 9C.

Figure 53:
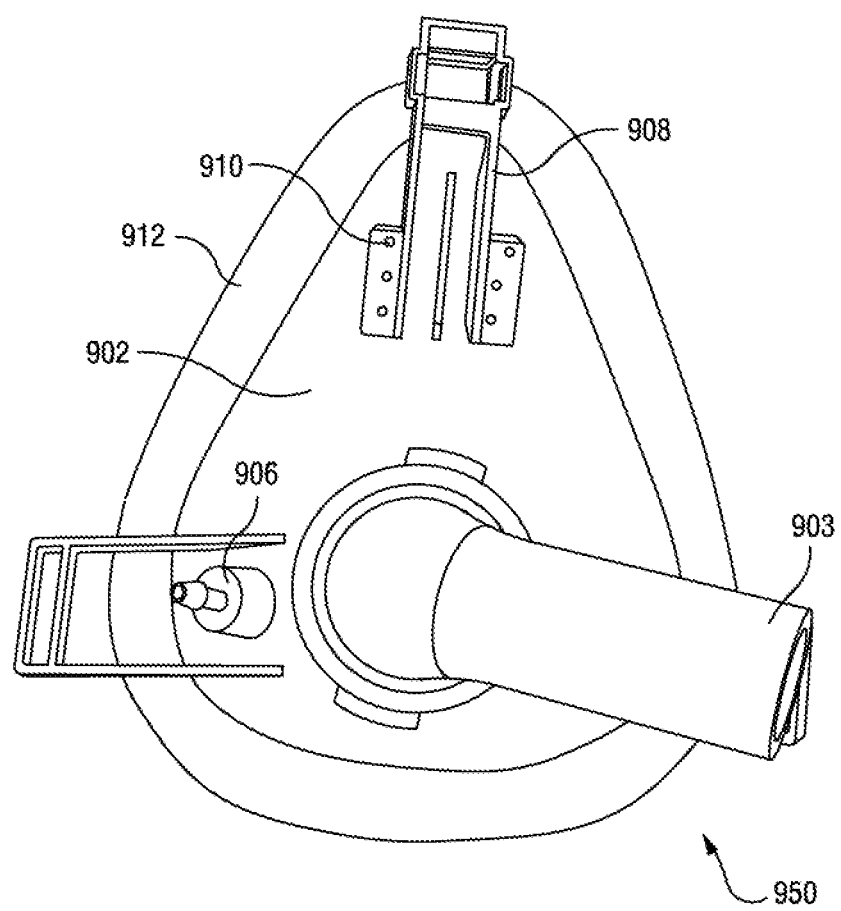
FIGS. 53-55 illustrate a full face mask assembly according to yet another embodiment of the present invention.
Figure 54:
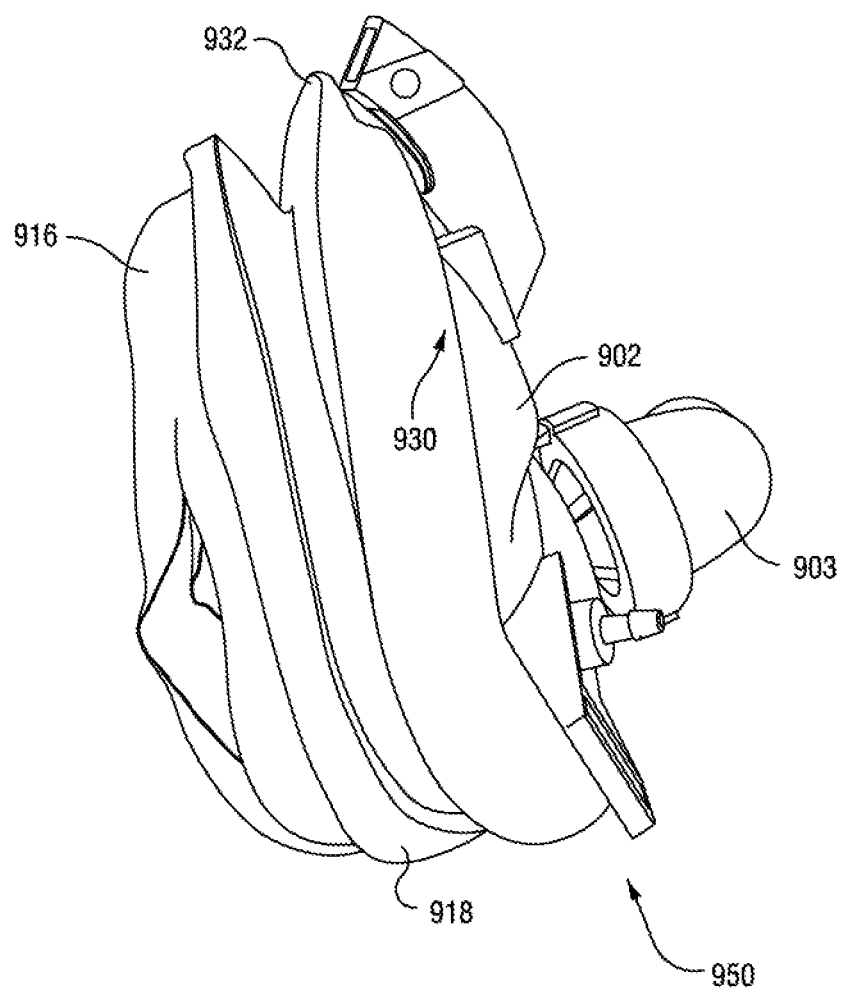
Figure 55:
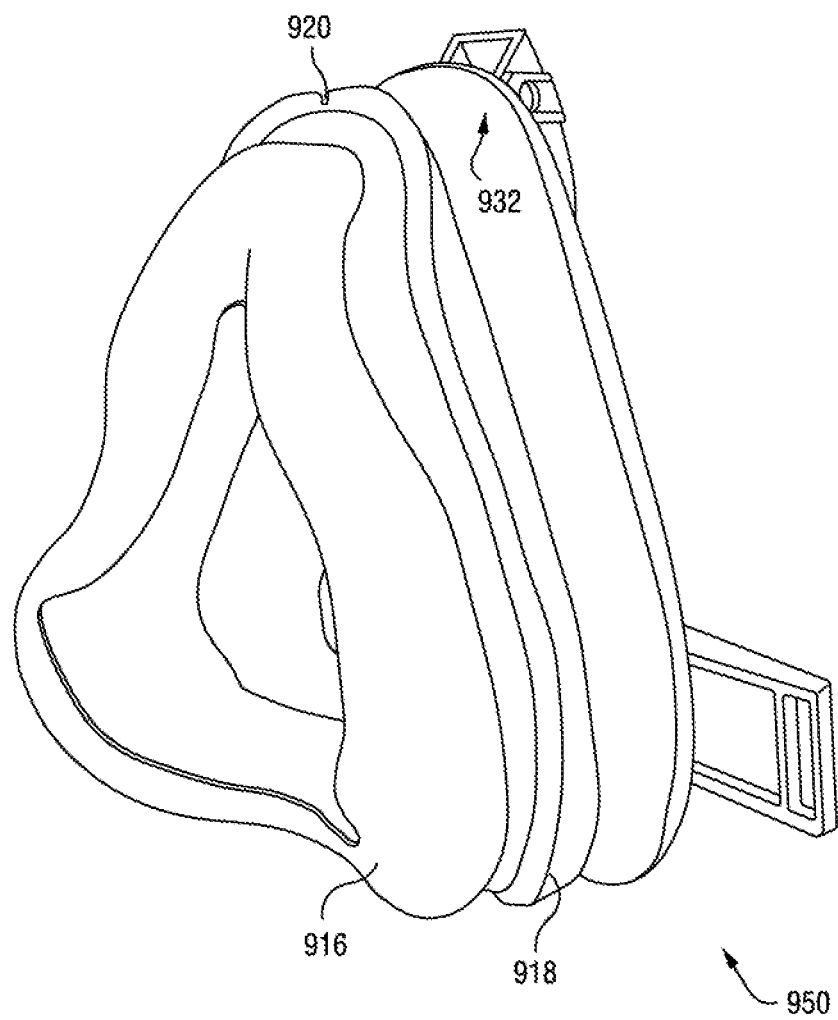

FIGS. 53-55 disclose a mask assembly 950 according to yet another embodiment of the present invention. Mask assembly 950 includes a shell substantially identical to that described in relation to FIGS. 50-52, and will not be described in more detail with respect to this embodiment. The main difference between this embodiment and the embodiment of FIGS. 50-52 resides in the structure and function of cushion 912. For example, cushion 912 in FIGS. 53-55 has a gusset 932 which is generally equal in the nasal bridge region, the cheek regions, and the lower lip region. For example, in comparing FIGS. 51 and 54, it can be seen that the gusset portion 932 in the nasal bridge region in FIG. 54 extends higher than the edge of the shell 902, as opposed to the arrangement shown in FIG. 51 in which the nasal bridge region 914B is substantially equal in height as compared to shell 902. In addition, cushion 912 shown in FIGS. 53-55 includes an insert 918 similar to that described in relation to FIGS. 50-52. Insert 918 may include a gap 920 (FIG. 55) which is provided in the nasal bridge region of insert 918.

Headstrap Plate Variation

Figure 56:
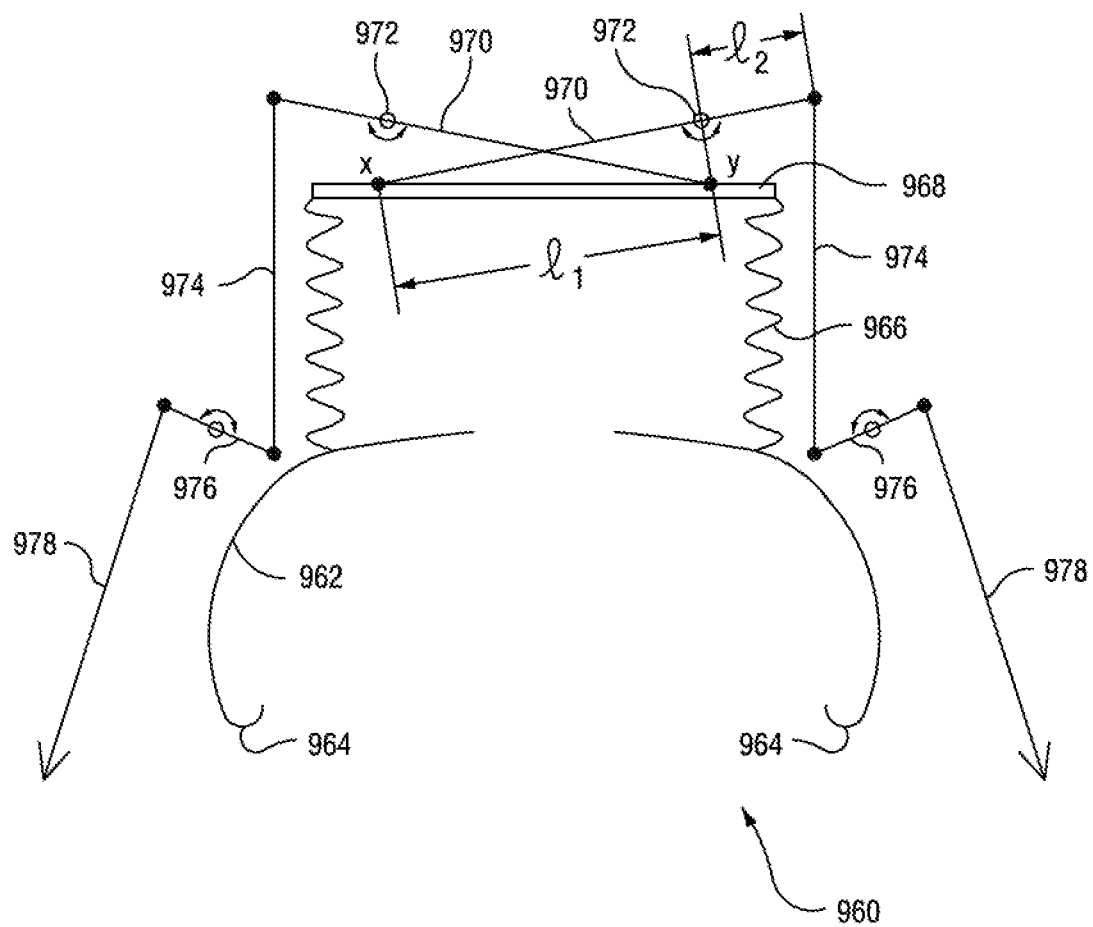
FIG. 56 is a schematic diagram illustrating a mask assembly according to another embodiment of the present invention.

FIG. 56 illustrates schematically a mask assembly 900 according to another embodiment of the present invention.

Mask assembly 960 includes a cushion 962 including a face contacting portion 964 which may be similar to that described above. Cushion 962 is supported by a bellows 966 which in this embodiment is further provided to a plate 968. The bellows 966 may expand under mask pressure. Plate 968 can have a total force defined by the area of the plate times the mask pressure to which the plate is subjected ($F=Area \times P$).

The force is applied to ends x and y of lever arms 970 and 970, respectively, so that each lever area experiences a force defined by the area times the pressure divided by two ($F=Area \times P/2$). Each lever 910 is mounted so as to pivot about an axis 972, which in this example is asymmetrically oriented such that it defines a distance $\ell_1$ and a second distance $\ell_2$. The force is multiplied by the ratio $\ell_2$ divided by $\ell_1$ ($\ell_2/\ell_1$) and transferred to a rod 974 provided to each lever 970. Each rod 974 is connected to a strap lever 976, which in this case is pivotably mounted at a point which is approximately in the center of lever 976. Lever 976 in turn is connected to a strap portion of 978 of a headgear assembly. Accordingly, each strap 978 is tensioned with the force defined by the relation:

$$F = \text{Area} \times P/2 \times {}^{t2}/{t1}$$

Accordingly, strap tension is proportional to mask pressure.

After-Market Clamp Accessory

Figure 34:
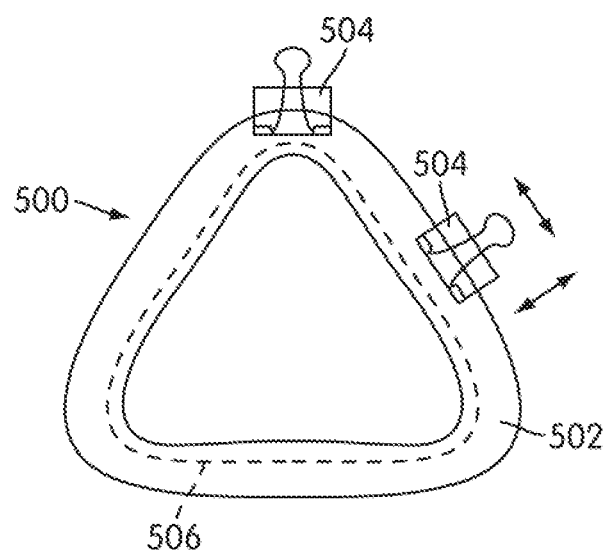
FIG. 34 is a schematic view illustrating a clamp according to an embodiment of the present invention.

FIG. 34 illustrates a cushion 500, generally like the cushion shown in FIG. 1. Cushion 500 includes a gusset portion 502. One or more clamps, schematically shown as paper clips 504 in this example, can be applied to gusset portion 502 in various positions. Clamps 504 can be positioned radially outward from the cushion to adjust the width of gusset portion 502, which may include a spring portion, to thereby adjust the projected area. Clamps 508 are positioned on the cushion where it is desirable or allowable to reduce the contact force. Further, the clamps may be positioned along any portion of the perimeter of cushion 500, to thereby fine tune balance between maximum comfort and sealing force.

As an alternative, gusset portion 502 may include a linear fastener such as a tongue and groove arrangement that is used in Zip-Loc™ plastic bags. The linear fastener may be provided along the entire perimeter, as shown in imaging dotted lines 506 in FIG. 34, or only a portion thereof, of the cushion 500. When tongue and groove of linear fastener are engaged, the gusset portion 502 would be generally inoperable, such that the cushion 500 would operate as though it did not include a gusset portion. Alternatively the tongue and groove of linear fastener are positioned mid-way or at some preferred distance from the edge of the gusset and when engaged, whilst the gusset portion exterior to the tongue and groove is inoperable, the gusset within the tongue and groove still operates. This may be used to apply a gusset to selected regions of the face for example. In another alternative, the cushion could include a plurality of concentric sets of tongues/grooves, such that the width of the gusset portion can be selectively adjusted.

Figure 35:
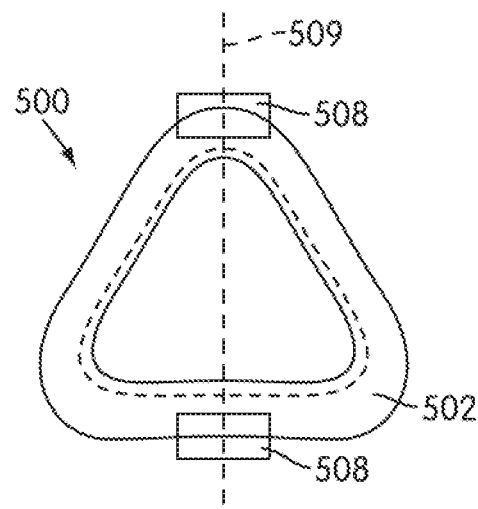
FIG. 35 is a schematic view illustrating another clamp according to the present invention.
Figure 36:
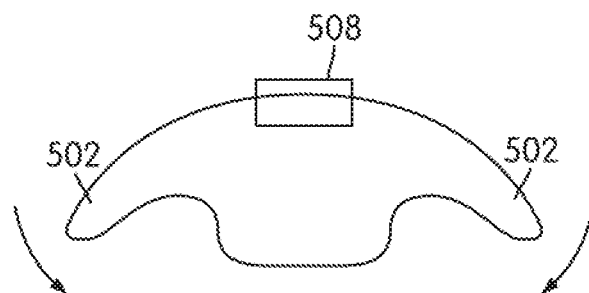
FIG. 36 is a partial schematic view illustrating still another clamp according to the present invention.

FIG. 35 illustrates cushion 500 with another example of a clamping arrangement. In this embodiment, clamps 508 may be made of plastic and/or metal. Clamps 508 are provided along a central axis 509 of cushion 500. As shown in FIG. 36, cushion 500, in particular the lateral sides of gusset portion 502, are encouraged to flex or bow about axis 509, thereby wrapping the gusset portion 502 and/or adjoining sections of the cushion 500 towards the patient's face in the cheek regions. This helps promote a good seal in a region of the patient's face which is best able to withstand prolonged sealing forces. Thus, wrapping or bowing of the gusset portion can be achieved without the use of clamps 508.

Clamps 504, 508 can be provided as an after-market accessory, to help patients tailor the cushion fit according to their special needs. Alternatively, a range of cushions with gusset portions having various profiles, sizes, and spring constants could be provided.

Over-the-Head Mask Systems

Figure 37:
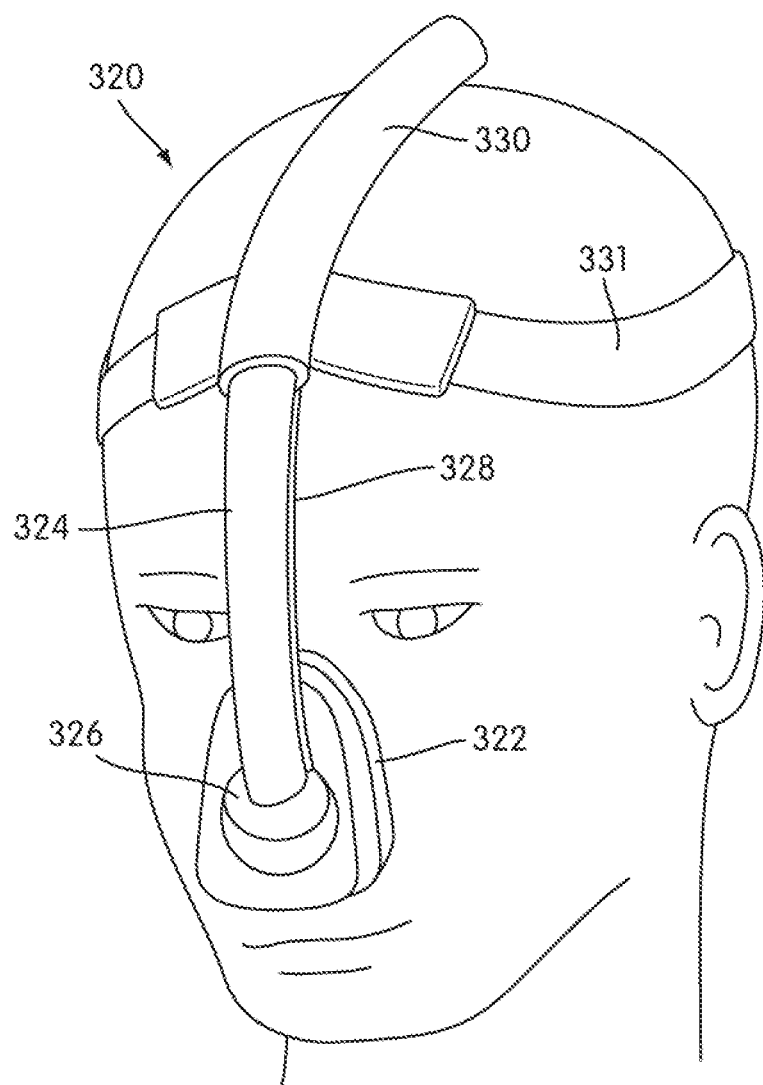
FIG. 37 illustrates a further embodiment according to the present invention.

FIG. 37 illustrates a mask assembly 320 including a patient interface 322, e.g., a cushion or a nozzle assembly, which is in communication with an over-the-head air inlet tube 324. A ball joint 326 or hinge, e.g., forms a connection between interface 322 and tube 324. Tube may optionally include a spring 328, e.g., a stainless steel leaf spring, to help bias the interface 322 towards the patient's face, to thereby help ensure support for mask and/or a good seal, while at the same time offering a higher degree of flexibility and/or comfort. Alternatively, the inlet tube 324 can be formed of a material having inherent resiliency, thereby avoiding the need for spring 328. Inlet tube 324 received pressurized gas from air delivery conduit 330. Headgear 331 is provided to support and/or hold the mask assembly and/or the air delivery conduit.

With this arrangement, ball joint 326 allows interface 322 to rotate about all axes of movement, at least to some degree. This helps to decouple for forces associated with supporting the headgear from the forces associated with a maintaining a seal. This is similar to the use of a gusset, which also helps decouple these forces. In yet another embodiment, the spring 328 and/or tube 324 could have a variable stiffness than changes with pressure, e.g., get stiffer with pressure increases.

Figure 38:
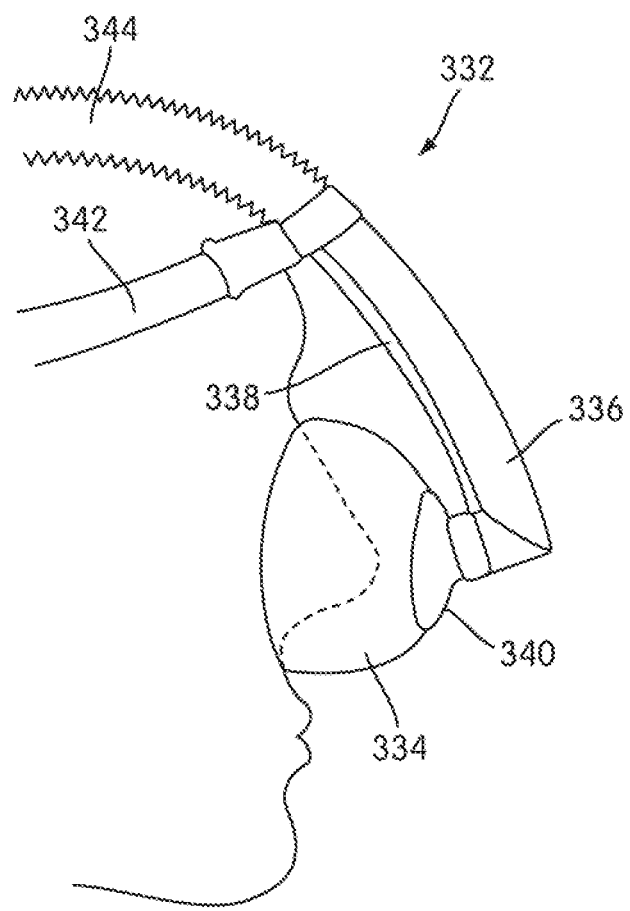
FIG. 38 illustrates an additional embodiment according to the present invention.

In an alternative embodiment shown in FIG. 38, mask assembly 332 includes a flexible wall joint 340 to replace the ball joint from FIG. 37. Wall joint 340 allows relative movement between interface 334 and inlet tube 336. Inlet tube 336 may include inherent springness, or it may include spring, e.g., a stainless steel leaf spring 338. Headgear 342 may be provided to support mask assembly and/or air delivery conduit 344. Tube 336 and/or spring 338 may change stiffness with pressure variations, as described above.

Changeable Extendability of Headgear

In another form of the invention, the extensibility of the headgear is selectively variable. For example, relatively low elasticity headgear might be used for low mask pressures, while relatively higher elasticity headgear may be used for high mask pressures, such as around 20 cm $H_2O$. In one form, this is achieved by having duplicate straps within the headgear, one extensible, the other, relatively inextensible. At low pressures, both straps are used, the net effect being that the headgear is relatively inextensible. At high pressures, the inextensible strap is disengaged, with the result that the headgear is relatively extensible overall.

Figure 39:
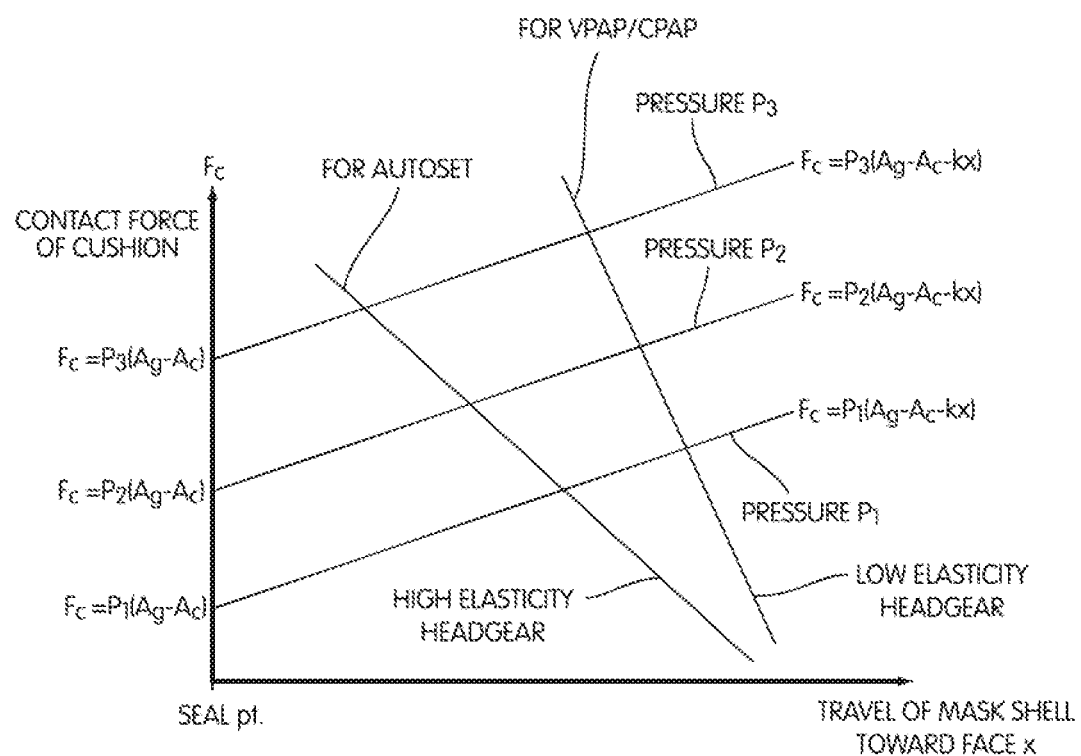
FIG. 39 is a graph which illustrates the relation between contact force applied to the patient's face and travel of the frame toward the face according to an aspect according to the present invention.

FIG. 39 illustrates the contact force of the cushion on the patient's face against travel of the mask shell towards the face. As can be seen from FIG. 39, the contact force of the cushion $F_c$ linearly increases with the travel of the mask shell towards the face, for three constant pressures P1, P2 and P3. For each pressure, the contact force $F_c$ is defined by the relation $F_c = P_t(A_g - A_c)$, where $A_g$ is the projected area of the gusset and $A_c$ is the contact area between the face and the cushion, e.g., the membrane of the cushion. If the gusset includes a spring, a spring constant k times its displacement distance x must be taken into account as well.

FIG. 39 shows a first curve which represents headgear with low elasticity, and a second curve which represents headgear with high elasticity. Low elasticity headgear may be used for VPAP and CPAP applications, while high elasticity headgear may be useful for auto set applications.

For CPAP, a constant position may be preferable, ie: the force is maintained constantly with the set pressure at the preferred sealing and comfort position. The gusset still provides flexibility to allow for movements in head position and skin position through the night. The use of low elasticity headgear means that this position is maintained. However some users may prefer high elasticity for comfort and a totally flexible system.

For VPAP, a low elasticity headgear may be preferred since this prevents the frame 'bouncing', ie: moving backwards and forwards with changes in pressure since both the gusset and headgear are elastic. This 'bouncing' may disrupt the flow generator control systems or may lead to discomfort. Similarly, some users may prefer high elasticity for comfort and a totally flexible system.

Figure 40:
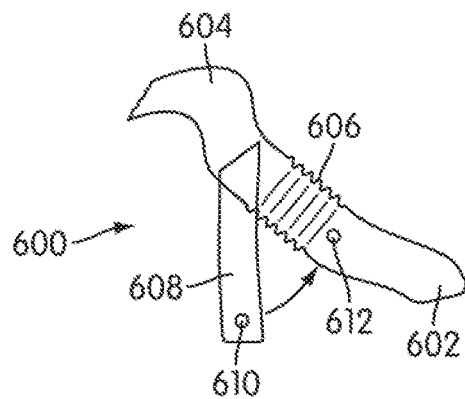
FIGS. 40 and 41 illustrate a portion of a headgear assembly according to an embodiment of the present invention.
Figure 41:
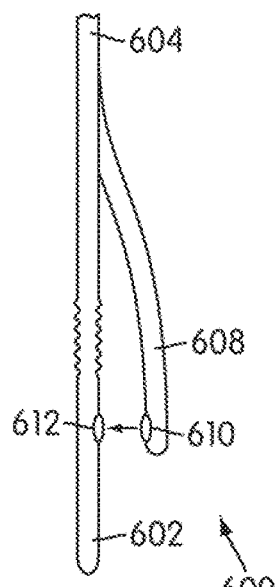

FIG. 40 illustrates an embodiment including headgear with selectively variable elasticity. For example, a portion 600 of a headgear strap is shown in FIGS. 40 and 41. Headgear strap portion 600 includes a first end 602 structured to connect with a slotted headgear connector formed on forehead support or mask frame, as shown in FIG. 1. Portion 600 includes a second end 604 which is configured for connection to a rear part of the headgear which is guided around the back of the patient's head. Headgear strap portion 600 includes an intermediate portion 606 which includes gathers. First and second portions 602 and 604 are made of relatively inextensible or relatively non-elastic materials such that there length does not substantially change upon application of tensile forces. In comparison, intermediate portion 606 is relatively elastic and can change in accordance with strap tension. Examples of the materials used for the relatively more elastic intermediate portion 606 include any suitable elastomeric material which is suitably covered with a cloth material that is comfortable to the patient. Therefore, if the patient or clinician selects relatively more extensible headgear for use with a particular patient's therapy, the relatively elastic intermediate portion will change in length as pressure is changed.

Headgear portion also includes a supplemental strap portion 608 which is made of a relatively less or substantially inextensible material. Supplemental strap portion 608 includes a fastener 610 which may be selectively coupled with a complimentary fastener portion 612 provided on first portion 602, which is substantially inelastic. Fasteners may take the form of buckles, snaps and VELCRO®, for example. If the fasteners 610 and 612 are engaged, headgear strap portion 600 is thereby rendered substantially inextensible, as the supplemental strap portion 608 forms a bridge over and renders inoperative the relatively elastic intermediate portion 606. FIG. 41 is a side view showing additional details of strap portion 600. Also, strap portion 608 allows a patient to stretch a mask system off the head without unclipping or detaching, thereby improving convenience of removing mask and donning same.

Figure 42:
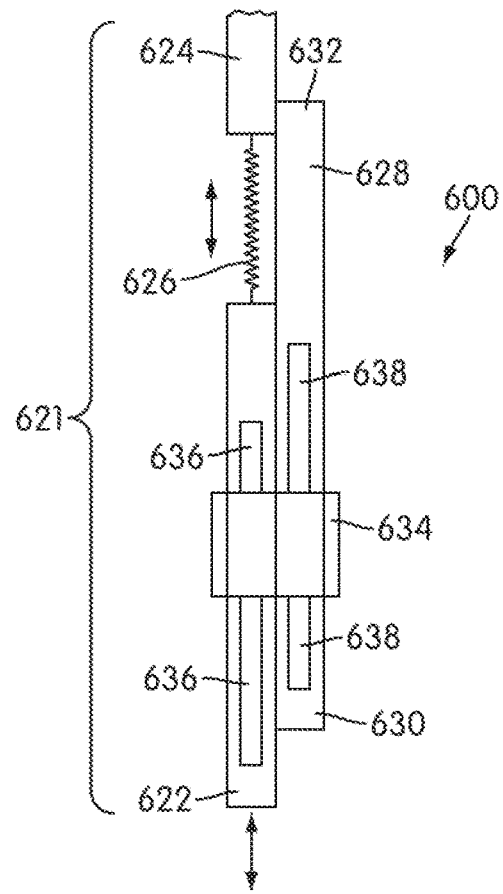
FIG. 42 illustrates a further alternative headgear strap embodiment according to the present invention.

In accordance with another embodiment, the selection of either the extensible or substantially inextensible modes can be performed automatically, in conjunction with the operating pressure of the system. For example, FIG. 42 shows a portion 620 of strap assembly including a first portion 622 adapted to be provided to a slotted connector or a slotted connector clip of the mask frame or forehead support. The second end 624 is provided to the remaining portion of headgear which leads to the rear portion of the patient's head. Headgear also includes a relatively elastic portion, schematically illustrated as element 626 in FIG. 42. As indicated, the elasticity of portion 626 allows the headgear to extend with increased pressure or tensile forces applied to the strap. First and second portions 622 and 624 are made of relatively inextensible or non-elastic material. A supplemental strap portion 628 includes a first end 630 provided adjacent first portion 622 of the strap assembly. Supplemental strap portion 628 includes a second end 630 fixedly attached to second end 624. A sleeve 634 may be provided to surround a portion of main strap portion 621 and supplemental strap portion 628. A portion of main strap portion 621 includes a first coupling member 636 while supplemental strap portion 628 includes a second coupling member 638. Coupling members 636 and 638 may be in the form of an electromagnetic assembly which is selectively operable in dependence on sensed operating pressure of the mask assembly. Accordingly, if the mask operating pressure is too high, coupling attraction between coupling members 636 and 638 can be discontinued, thereby allowing the headgear portion 620 to stretch via relatively elastic or extensible portion 626. At relatively lower pressures, the coupling members 636 and 638 can be engaged so that the headgear becomes relatively inelastic, which thereby improves sealing at lower operating pressures. Of course, the use of electromagnetic coupling members is exemplary only, as numerous other alternatives would be apparent to one of ordinary skill in the art.

Figure 42A:
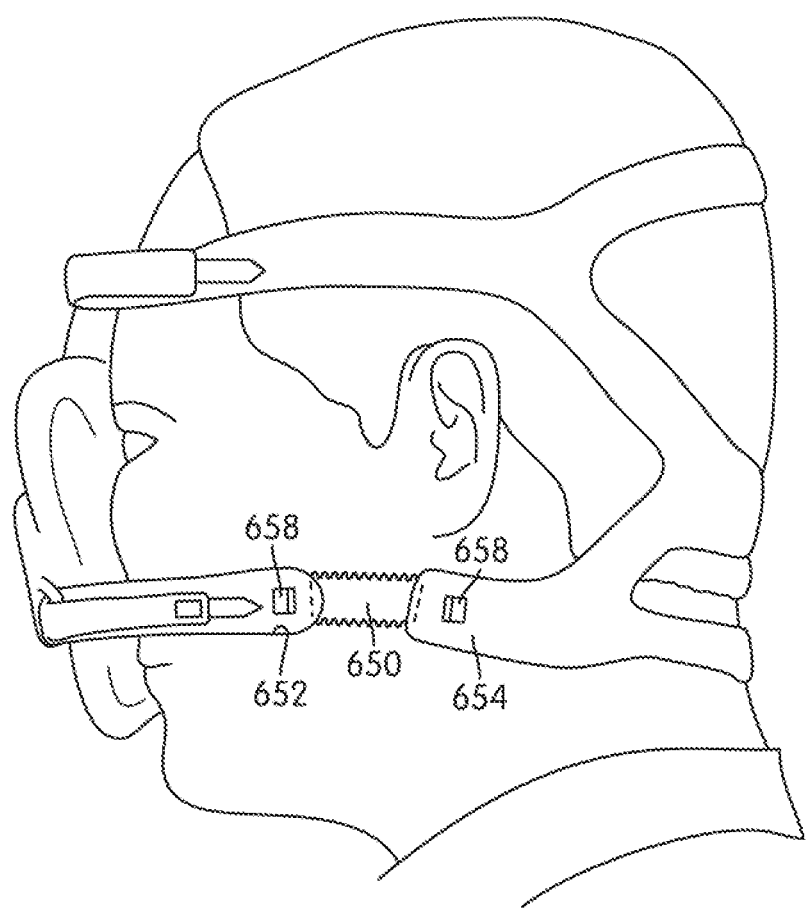
FIGS. 42A and 42B illustrate headgear according to an embodiment of the present invention.
Figure 42B:
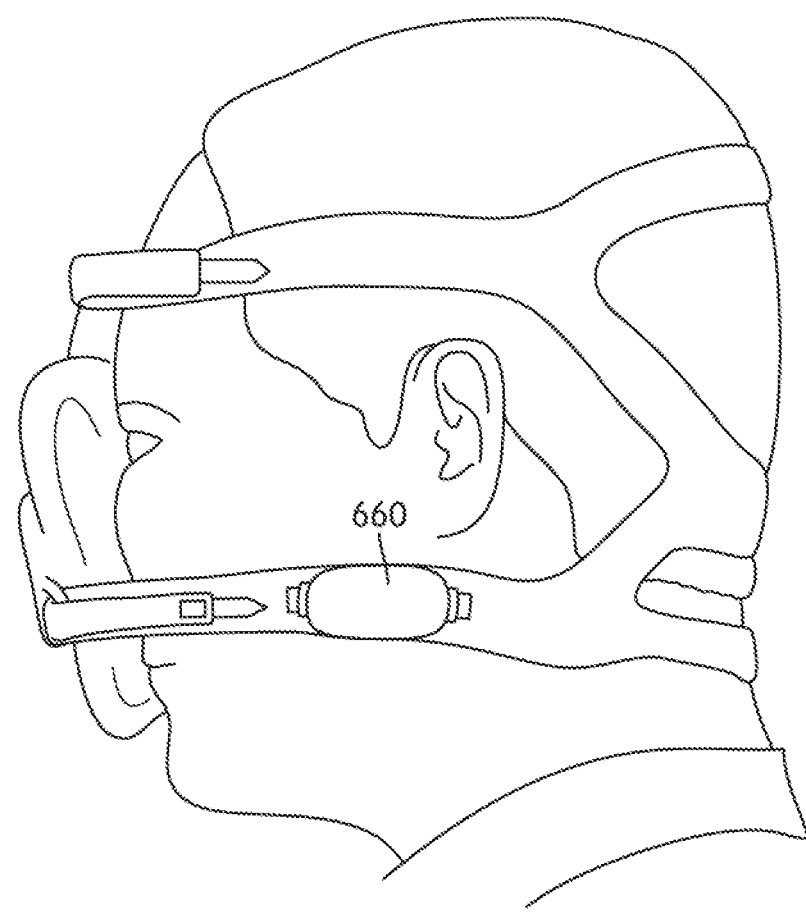

FIGS. 42A and 42B schematically illustrate mask systems on a patient that utilize selectively extensible headgear. In FIG. 42A, an elastic strap portion 650 forms a bridge between relatively non-extendible portions 652, 654 of headgear, thereby allowing the lower strap portion, as a whole, to stretch.

Portions 652, 654 include recesses 658 (FIG. 42A) that are adapted to receive a relatively inextensible strap portion or member 660, shown in position in FIG. 42B. Member 660 includes hooks or projections that are received in recesses 658.

In one example, the headgear may be used with a gusset portion or a improvised or simulated gusset portion described above. When used in conjunction with the autosetting device, an advantage over substantially inextensible headgear can be gained by employing headgear which incorporates a set amount of elasticity. This provides a system that allows the headgear length to be set at a low initial pressure for the autoset unit, e.g., about 4-6 cm H$_2$O. At these pressures, the gusset portion should normally be set in a substantially closed position, allowing the maximum force to be applied. See FIG. 39. This provides a seal even at low mask pressure. As the pressure is increased using the autoset system, the gusset may ideally extend away from the face, providing less force than if it was in the almost closed position and thus more comfort, although a seal is still maintained as the pressure is higher than it was at the low setting (4-6 cm H$_2$O). A similar behaviour to this could also be used for the ramping functionality of the flow generators (i.e., those machines that start at a low pressure and then ramp to the preferred setting). The extensibility preferred to allow the gusset to move away from the face can be achieved by modifying the material that is used for the headgear, e.g., silicone versus polypropylene. Alternatively, an elastic strip can be incorporated into the headgear, as described above in relation to FIGS. 40 and 41. As an additional feature this strip may incorporate a clip or hook or other fasteners so that it may be restrained when the elasticity is not required. This, therefore, provides a headgear than can be optimized for either CPAP or bi-level treatment where elasticity is not required or auto setting treatment where elasticity is preferred. See FIG. 39.

Further Embodiments

Figure 43:
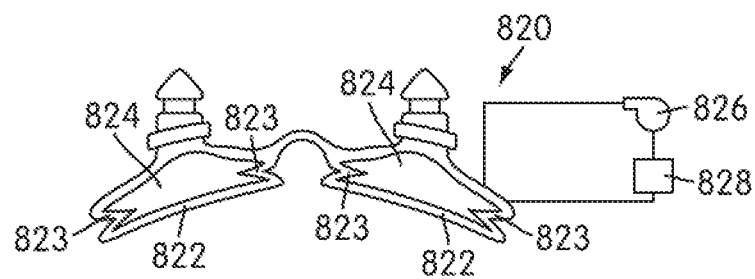
FIG. 43 is a schematic top view of a forehead pad assembly according to an embodiment of the present invention.

In another embodiment shown in FIG. 43, the force associated with use of forehead pad assembly 820 can be changed in dependence of treatment pressure. The forehead pad assembly 820 can be attached to a forehead support in the manner illustrated in FIGS. 25, 26, 27A and 27C. This may provide a way of optimizing position relative to the face and improve comfort by providing something that feels more like an air cushion. Such forehead pads could provide decoupling of the forces between the forehead support frame and the forehead pads in the patient's forehead region, which may improve patient comfort and compliance.

In an alternative, each forehead pad 822 may include a chamber 824 that may be filled with air, a gel, etc. The pressure within each chamber 824 may be fixed, meaning a closed system, or it can be linked to mask pressure, in which case the forehead support would be pushed away from the head when air pressure increases.

In another alternative, the pressure within each chamber 824 may be adjustable, e.g., via a pump 826. A servo control 828 could be used to set the pressure. In another alternative, the pressure could be controlling dynamically, independent from mask pressure, e.g., via servo control 828 that receives information from a position and/or pressure sensor. Such dynamic control can be pre-programmed and/or based on IPAP/EPAP, AutoSet changes in mask pressure at night, and/or the pressure ramp up stage as the patient falls asleep. Moreover, the feedback can be based on sensed leak measurement to adjust the forehead support to improve mask leaks in real time. Leak measurement can be used to dynamically adjust the forehead support when the patient falls asleep.

In still another embodiment, the pads 822 may be mounted on spring portions 823, which form a portion of or are inserted within a side walls of the pads. The embodiment can be used independently of or in conjunction with the other embodiments.

In another embodiment, the shape of the gusset portion may be maintained in an optimum position. For example, position sensors can be used to measure the displacement or change or shape of the gusset. The shape of the gusset portion can be changed, e.g., bent or straightened, depending on the sensed position of the gusset, or the sensed strap tension. In another example, the forehead pad(s) can be used to adjust the shape of the gusset portion. For example, a feedback loop may be used to monitor the position of the gusset portion, and the forehead pads can be mounted on a screw or other adjustable device which can be changed in dependence with the sensed shape and/or position of the gusset portion.

Figure 44:
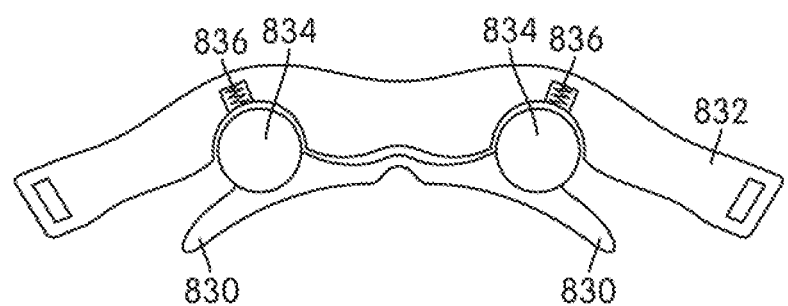
FIG. 44 is a schematic top view of a forehead pad and forehead support according to an embodiment of the present invention.
Figure 45:
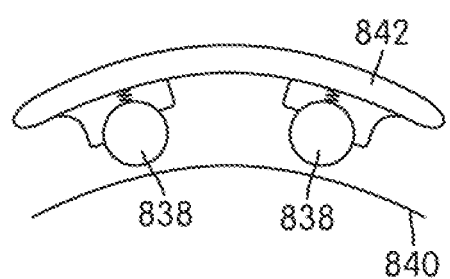
FIG. 45 is a schematic top view of a forehead support and pad assembly according to an embodiment of the present invention.

In yet another embodiment shown in FIG. 44, forehead pad(s) 830 can be adjustably mounted to forehead support 832. For example, the forehead pads 830 can be mounted to the frame using a ball joints 834 which pivot in two or more planes. This would effectively decouple the action of moving the forehead support or frame from the application of force to the patient. In addition, ball joints 834 can be mounted on springs 836 so they press against the forehead in a controlled fashion. Another embodiment is shown in FIG. 45, in which roller balls 838 contact the patient's forehead 840 and are spring mounted on a support 842. Therefore, the shape of the forehead pad is no longer compromised between comfort and load/deflection control. The springs control forces while the roller balls 838 are designed for comfort.

The forehead support provides vertical (relative to a vertical person) stability. The addition of a gusset, spring or gusset/spring combination to the forehead supports would provide an active support system that can adapt to changes in mask, user or strap position. In particular it would decrease the importance of the headgear strap position, allowing the forehead pads to accommodate a certain level of movement and thus preventing the requirement to over-tighten the headgear straps in order to ensure the mask is stable through the night.

In one embodiment, the forehead pads may be compressible in the axial direction towards the forehead support. This may be used in conjunction with a mask having a cushion with a gusset, and/or headgear with a main strap which has an elasticity that is selectively adjustable.

In other embodiment, the forehead support or the forehead pad may include an inflatable bladder or pillow. The pillow may inflate or deflate with changes in treatment pressure, which in turn may change the distance between the forehead support or pad and the patient's forehead. The forehead pad may be mounted on such a pillow via the use of any mechanical expedient, such as sliding pins with a spring, e.g., a silicone spring. Details of the pillow are described in ResMed Limited's currently pending PCT Application No. PCT/AU03/01471 filed Nov. 6, 2003, incorporated herein by reference in its entirety.

A pillow added to the forehead support or pad could effectively act as a shock absorber. In addition or as an alternative, the pillow may include a progressive spring constant which changes with pressure. This would help eliminate any adverse effects of using headgear having a limited range of extensibility.

In another example, the adjustable forehead support may include a cantilevered spring which extends from the mask to support the forehead support. As such, the forehead pads will be spring biased against the patient's forehead, but may resiliently flex in response to changes in strap tension and/or treatment pressure.

In each of these examples, it is desirable to maintain vertical stability through the pressure range. Such vertical stability may be created via friction between the forehead pads and the forehead or the cushion and the patient's nose region. Friction adequate to maintain the mask system in the vertical position can be achieved via the use of the expedients described above.

Figure 48:
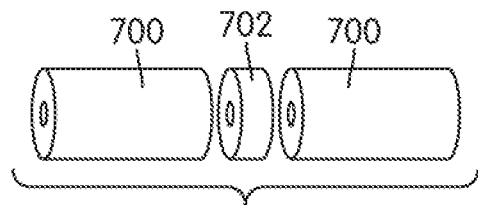
FIG. 48 is a schematic view of a pad position sensor according to an embodiment of the present invention.

In addition, it may be desirable to provide a system that can maintain the vertical position of the mask assembly. For example, as shown in FIG. 48, the forehead support may include at least one roller pad 700 which may rotate if it moves in relation to the patient's forehead. A sensor 702 may be provided on one of roller pads 700 to detect the amount, if any, of rotation of the roller pad 700, to thereby determine how much the mask assembly has moved in relation to the face.

Figure 46:
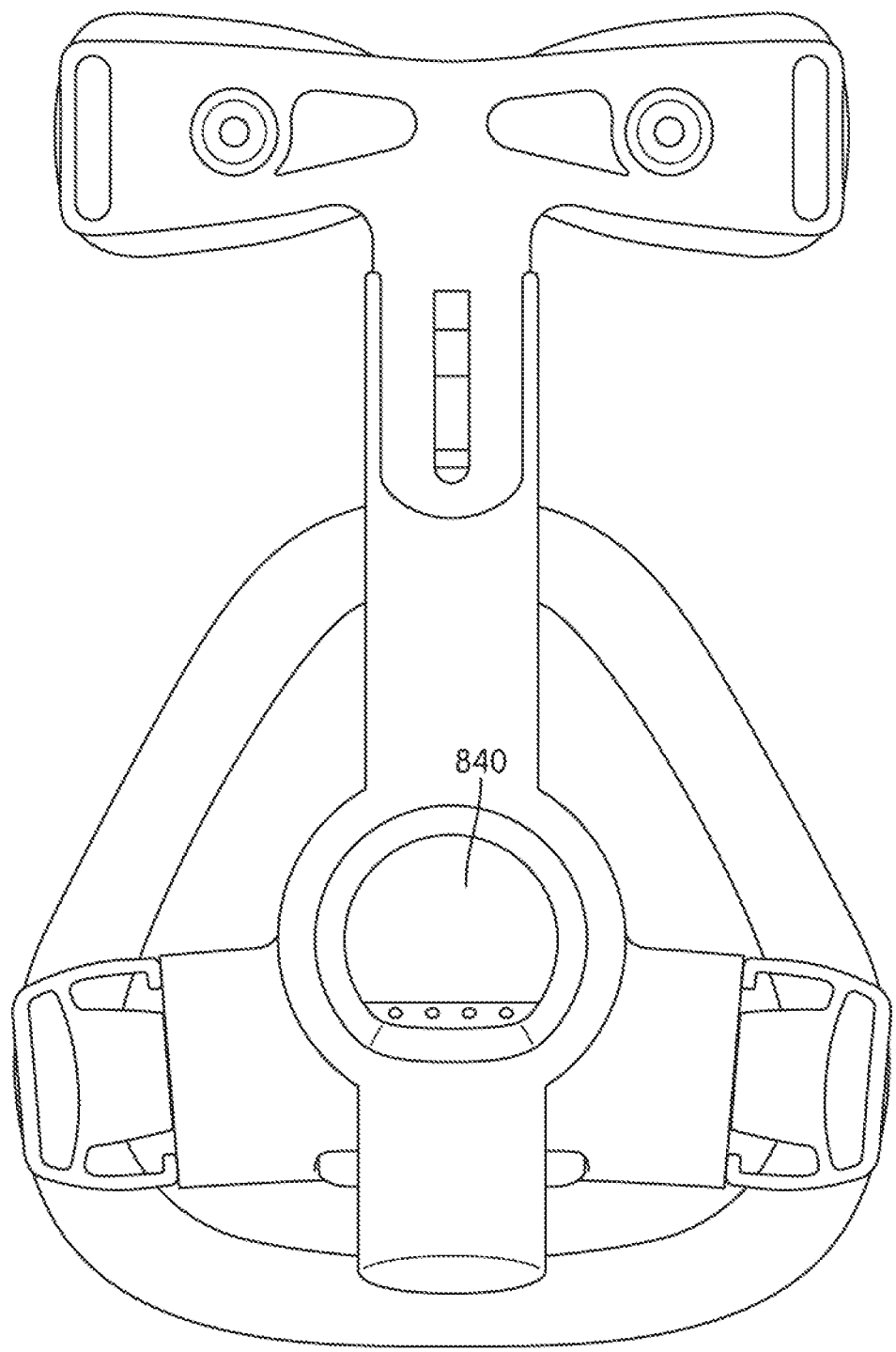
FIGS. 46 and 47 are schematic front views of a mask system with an adjustable vent cover according to an embodiment of the present invention.
Figure 47:
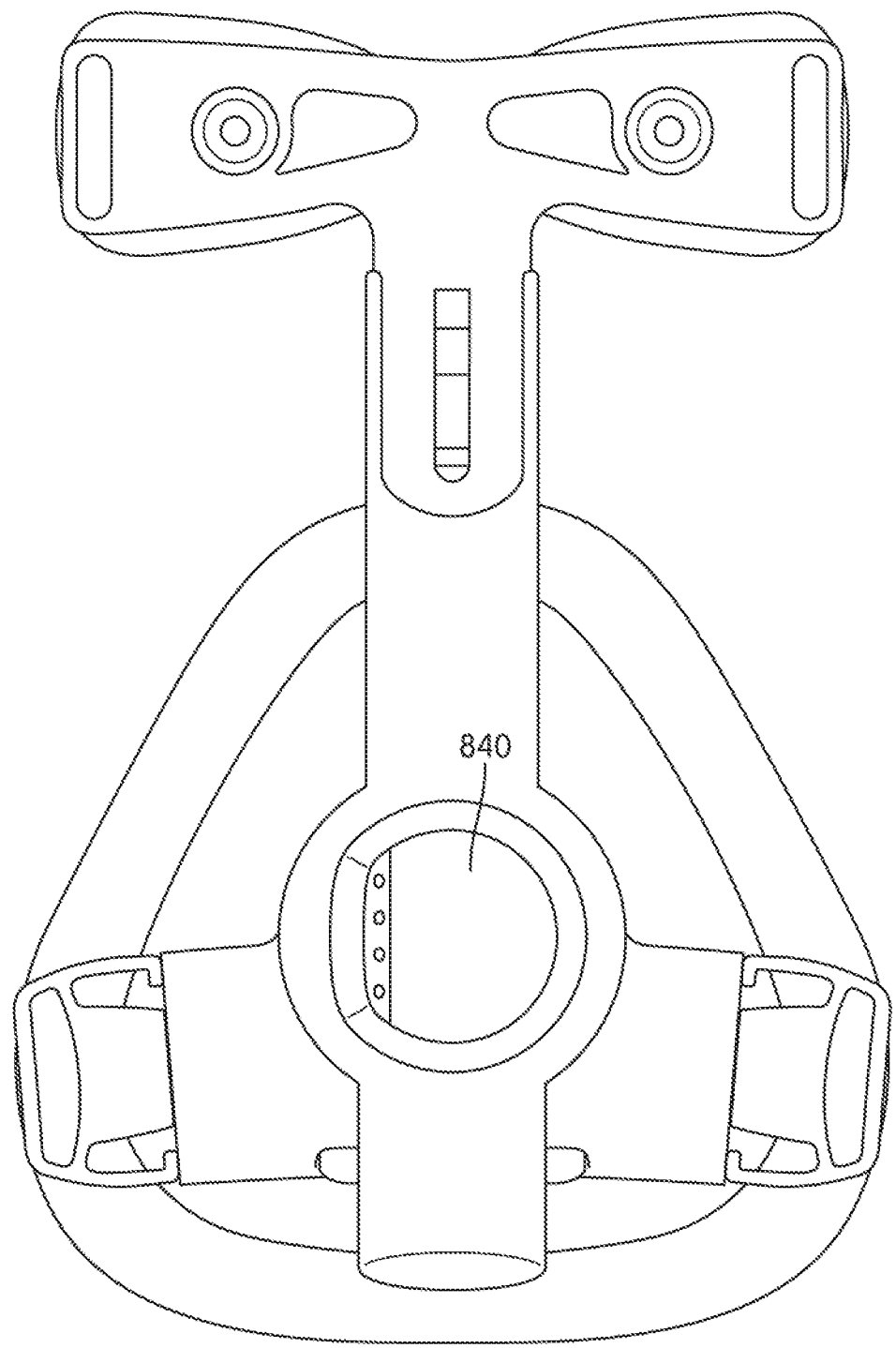

In another embodiment, the vent cover 840 as shown in FIGS. 46 and 47 can be designed such that it is rotatable with respect to the swivel elbow. For example, such rotation may include 0°-360° rotation. As such, the vented air can be diverted in any direction. As an alternative, the cover may be square-shaped and fit on a complimentary square-shaped portion of the swivel elbow. As such, the cover may be removed and placed in any one of four directions, thereby diverting the exhaled gas to the desired direction.

Figure 49:
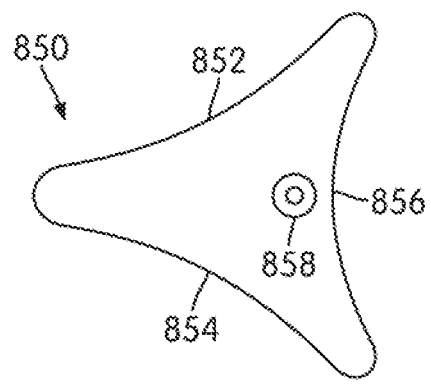
FIG. 49 is a schematic side view of a forehead pad according to an embodiment of the present invention.

FIG. 49 shows a schematic side view of a forehead pad 850 including three possible forehead engagement surfaces 852, 854, 856. Each surface includes a cupped, concave shape to resiliently contact the patient. Pad 850 includes a side lug 858 that is supported by a forehead support (not shown). Lug 858 is eccentrically mounted, or offset, so that the pad 850 spaces the forehead support away from the patient at three different distances depending on the surface 852, 854, 856 that contacts the patient's forehead.

The masks systems described herein can be modified, in accordance with the masks systems described in U.S. Non-Provisional application Ser. No. 09/885,455 filed Jun. 21, 2001, and U.S. Non-Provisional patent application Ser. No. 10/655,622 filed Sep. 5, 2003. Individual components of the embodiments can be combined, as would be understood, even though the exact combination of elements from different embodiments may not be explicitly shown in the drawings.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations and substitutions within the spirit and scope of the present disclosure.

What is claimed is:

1. A respiratory mask assembly for delivering breathable gas in a range of operating pressures to a patient for treatment of sleep disorder breathing, the respiratory mask assembly comprising:
    a patient interface forming at least a portion of a cavity that is pressurizable to an operating pressure; and
    headgear constructed and arranged to hold the patient interface in position on a patient's face, the headgear including:
        at least one main strap portion having first and second end portions that are substantially non-elastic and a central portion that is relatively more elastic, and
        a supplemental strap portion that is selectively coupleable to the first and second end portions of the at least one main strap portion in accordance with the operating pressure of the patient interface, the supplemental strap portion being substantially non-elastic,
        wherein the at least one main strap portion is overall substantially non-elastic if the supplemental strap portion is coupled to the first and second end portions, and the at least one main strap portion is at least relatively more elastic if the supplemental strap portion is decoupled from the first and second end portions.

2. The respiratory mask assembly according to claim 1, wherein the at least one main strap portion includes a main fastener that is selectively attachable to and detachable from a supplemental fastener of the supplemental strap portion.

3. The respiratory mask assembly according to claim 1, wherein the supplemental strap portion is automatically coupled to and decoupled from the at least one main strap portion in accordance with the operating pressure of the patient interface.

4. The respiratory mask assembly according to claim 1, wherein the supplemental strap portion, when coupled to the at least one main strap portion, is structured and arranged to substantially resist extension of the central portion at low operating pressures, and
    wherein the supplemental strap portion, when decoupled from the at least one main strap portion, is structured and arranged to allow extension of the central portion at high operating pressures that are higher than said low operating pressures.

5. The respiratory mask assembly according to claim 4, wherein the range of operating pressures is about 4-20 cm $H_2O$, and said low operating pressures is in a range of 4-6 cm $H_2O$.

6. The respiratory mask assembly according to claim 1, wherein the patient interface is structured and arranged to form a contact seal with the patient's face, and the supplemental strap portion is selectively coupleable to the at least one main strap portion in accordance with the operating pressure while maintaining the contact seal throughout the range of operating pressures.

7. The respiratory mask assembly according to claim 1, wherein the patient interface comprises a frame and a cushion, and the headgear is structured and arranged to connect to the frame.

8. The respiratory mask assembly according to claim 1, wherein the patient interface comprises a cushion with a gusset portion, the gusset portion configured to automatically adjust a component of force applied to the patient's face by the cushion in accordance with the operating pressure.

9. The respiratory mask assembly according to claim 1, wherein the patient interface comprises a nozzle assembly.

10. The respiratory mask assembly according to claim 1, wherein the range of operating pressures is about 4-20 cm $H_2O$.

11. Headgear for use with a respiratory mask, comprising:
    at least one main strap portion having first and second end portions that are substantially non-elastic and a central portion that is relatively more elastic; and
    a supplemental strap portion that is selectively coupleable to the first and second end portions of the at least one main strap portion, the supplemental strap portion being substantially non-elastic,
    wherein the at least one main strap portion is overall substantially non-elastic if the supplemental strap portion is coupled to the first and second end portions, and the at least one main strap portion is at least relatively more elastic if the supplemental strap portion is decoupled from the first and second end portions,
    wherein the supplemental strap portion is automatically coupled to and decoupled from the at least one main strap portion in accordance with pressure, and
    wherein the at least one main strap portion and the supplemental strap portion are electromagnetically coupled to and decoupled from one another.

12. The headgear according to claim 11, wherein the supplemental strap portion, when coupled to the at least one main strap portion, is structured and arranged to substantially resist extension of the central portion at low operating pressures of the respiratory mask, and
    wherein the supplemental strap portion, when decoupled from the at least one main strap portion, is structured and arranged to allow extension of the central portion at high operating pressures of the respiratory mask that are higher than said low operating pressures.

13. The headgear according to claim 12, wherein a range of operating pressures of the respiratory mask is about 4-20 cm $H_2O$, and said low operating pressures is in a range of 4-6 cm $H_2O$.

* * * * *